(12) United States Patent
Zhu et al.

(10) Patent No.: US 12,258,344 B2
(45) Date of Patent: Mar. 25, 2025

(54) AZAAROMATIC AMIDE DERIVATIVES FOR THE TREATMENT OF CANCER

(71) Applicant: SHENZHEN FORWARD PHARMACEUTICALS CO., LTD., Guangdong (CN)

(72) Inventors: Chenggang Zhu, Guangdong (CN); Xuan Yang, Guangdong (CN); Chaochun Zhang, Guangdong (CN); John J. Talley, Guangdong (CN); Chaole Chen, Guangdong (CN); Liming Bao, Guangdong (CN); Liangliang Xu, Guangdong (CN)

(73) Assignee: SHENZHEN FORWARD PHARMACEUTICALS CO., LTD., Guangdong (CN)

( * ) Notice: Subject to any disclaimer, the term of this patent is extended or adjusted under 35 U.S.C. 154(b) by 824 days.

(21) Appl. No.: 17/599,806

(22) PCT Filed: Mar. 30, 2020

(86) PCT No.: PCT/CN2020/082033
§ 371 (c)(1),
(2) Date: Oct. 15, 2021

(87) PCT Pub. No.: WO2020/200158
PCT Pub. Date: Oct. 8, 2020

(65) Prior Publication Data
US 2022/0177473 A1 Jun. 9, 2022

(30) Foreign Application Priority Data

Mar. 29, 2019 (CN) .......................... 201910252714.4
Jul. 9, 2019 (CN) .......................... 201910616031.2

(51) Int. Cl.
*C07D 471/04* (2006.01)
*A61K 45/06* (2006.01)
(Continued)

(52) U.S. Cl.
CPC ............ *C07D 471/04* (2013.01); *A61K 45/06* (2013.01); *C07D 251/16* (2013.01); *C07D 403/04* (2013.01)

(58) Field of Classification Search
CPC .. C07D 471/04; C07D 251/16; C07D 403/04; C07D 239/48; C07D 401/14;
(Continued)

(56) References Cited

U.S. PATENT DOCUMENTS

2019/0015413 A1 1/2019 Si et al.
2019/0100528 A1 4/2019 Wei et al.
(Continued)

FOREIGN PATENT DOCUMENTS

CA 2 803 056 12/2011
CA 2 843 109 1/2013
(Continued)

OTHER PUBLICATIONS

Examination Report issued Nov. 22, 2021 in Australian Patent Application No. 2020255100.
(Continued)

*Primary Examiner* — Matthew P Coughlin
*Assistant Examiner* — Meghan C Heasley
(74) *Attorney, Agent, or Firm* — WENDEROTH, LIND & PONACK, L.L.P.

(57) ABSTRACT

The present application relates to azaaromatic amide derivatives for the treatment of cancer. Specifically, the present application relates to a preparation method and use of azaaromatic amide derivatives. The present application relates to azaaromatic amide derivatives and anilino-pyrimidine compounds represented by formula (I), formula (II), formula (III), formula (IV), and formula (V), and pharmaceutically acceptable salts thereof; the compounds or salts thereof can be used to treat or prevent a disease or disorder by regulating certain mutant forms of epidermal growth factor receptors. The present application also relates to a pharmaceutical composition comprising the compounds or salts thereof, and a method for treating various diseases mediated by EGFR, or HER2, or HER4 by using the compounds and salts thereof.

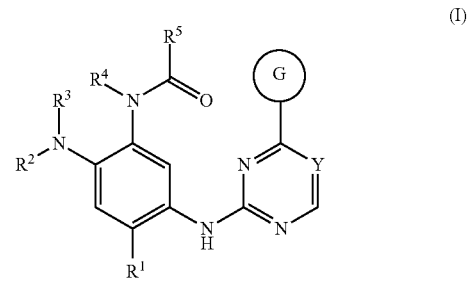

(I)

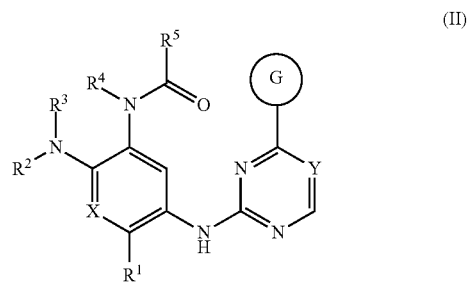

(II)

(Continued)

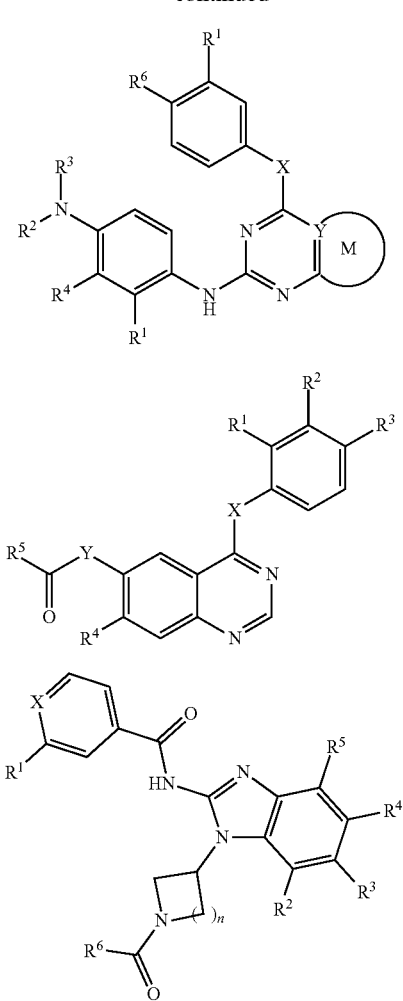

8 Claims, No Drawings

(51) Int. Cl.
  *C07D 251/16* (2006.01)
  *C07D 403/04* (2006.01)
(58) Field of Classification Search
  CPC .. C07D 403/12; C07D 487/04; C07D 495/04;
       A61K 45/06; A61K 31/506; A61K
       31/517; A61K 31/53; A61K 31/55; A61K
       31/519; A61P 35/00; A61P 35/02
  See application file for complete search history.

(56) References Cited

U.S. PATENT DOCUMENTS

| | | | |
|---|---|---|---|
| 2019/0152954 A1 | 5/2019 | Wang et al. | |
| 2019/0298687 A1 | 10/2019 | Gao | |
| 2020/0216444 A1 | 7/2020 | Duan | |

FOREIGN PATENT DOCUMENTS

| | | | |
|---|---|---|---|
| CA | 2 875 966 | 12/2013 | |
| CA | 2 881 275 | 2/2014 | |
| CA | 2 901 269 | 9/2014 | |
| CA | 2 940 488 | 9/2015 | |
| CA | 2 962 914 | 4/2016 | |
| CA | 3 016 092 | 9/2017 | |
| CA | 2 956 628 | 10/2018 | |
| CA | 2 997 039 | 9/2020 | |
| CA | 3 016 826 | 6/2022 | |
| CN | 102482277 | 5/2012 | |
| CN | 102947316 | 2/2013 | |
| CN | 103748096 | 4/2014 | |
| CN | 104379575 | 2/2015 | |
| CN | 105175349 | 12/2015 | |
| CN | 105209456 | 12/2015 | |
| CN | 105254615 | 1/2016 | |
| CN | 105315259 | 2/2016 | |
| CN | 105461695 | 4/2016 | |
| CN | 106279160 | 1/2017 | |
| CN | 106536506 | 3/2017 | |
| CN | 106795144 | 5/2017 | |
| CN | 106928200 | 7/2017 | |
| CN | 107163026 | 9/2017 | |
| CN | 107266437 | 10/2017 | |
| CN | 107935995 | 4/2018 | |
| CN | 108864079 | 11/2018 | |
| CN | 108864079 A * | 11/2018 | ............ A61P 35/00 |
| CN | 108884072 | 11/2018 | |
| CN | 108947974 | 12/2018 | |
| CN | 106749193 | 11/2020 | |
| EP | 3 112 364 | 1/2017 | |
| EP | 3 181 560 | 6/2017 | |
| EP | 3 216 786 | 9/2017 | |
| EP | 3 345 900 | 7/2018 | |
| EP | 3 345 906 | 7/2018 | |
| EP | 3 398 939 | 11/2018 | |
| EP | 3 653 622 | 5/2020 | |
| EP | 3 705 478 | 9/2020 | |
| EP | 3 434 673 | 2/2021 | |
| JP | 2017-506667 | 3/2017 | |
| JP | 2018-525431 | 9/2018 | |
| KR | 10-2014-0047741 | 4/2014 | |
| KR | 10-2016-0116033 | 10/2016 | |
| KR | 10-2017-0031778 | 3/2017 | |
| KR | 10-2018-0098361 | 9/2018 | |
| WO | 2010/129053 | 11/2010 | |
| WO | 2013/014448 | 1/2013 | |
| WO | 2014/135876 | 9/2014 | |
| WO | 2015/143148 | 9/2015 | |
| WO | 2015/188747 | 12/2015 | |
| WO | 2015/188777 | 12/2015 | |
| WO | 2015/195228 | 12/2015 | |
| WO | WO-2015188747 A1 * | 12/2015 | ............ A61K 31/53 |
| WO | 2016/054987 | 4/2016 | |
| WO | 2016/105525 | 6/2016 | |
| WO | 2017/036263 | 3/2017 | |
| WO | 2017/086830 | 5/2017 | |
| WO | 2017/114500 | 7/2017 | |
| WO | 2017/161937 | 9/2017 | |
| WO | 2018/019204 | 2/2018 | |
| WO | 2018/210246 | 11/2018 | |
| WO | 2019/010295 | 1/2019 | |
| WO | 2019/197605 | 10/2019 | |
| WO | 2020/043757 | 3/2020 | |

OTHER PUBLICATIONS

Examination Report issued Mar. 31, 2022 in Australian Patent Application No. 2020255100.
Examination Report issued Jun. 3, 2022 in Australian Patent Application No. 2020255100.
Zhou, Ping et al., "Design, synthesis and evaluation of the osimertinib analogue (C-005) as potent EGFR inhibitor against NSCLC", Bioorganic & Medicinal Chemistry, 2018, vol. 26, pp. 6135-6145.
CAS Registry No. 1807761-67-6; STN Entry Date Sep. 21, 2015.
CAS Registry No. 1903753-92-3; STN Entry Date May 4, 2016.
CAS Registry No. 2251703-24-7; STN Entry Date Dec. 5, 2018.
Japanese Search Report issued Jan. 19, 2023, in corresponding Japanese Patent Application No. 2021-560345, with machine trans-

(56) References Cited

OTHER PUBLICATIONS lation—see citation of CAS Registry No. 2227198-40-3 (last structure on pp. 24 and 48).
International Search Report issued Jul. 3, 2020, in International (PCT) Application No. PCT/CN2020/082033, with English translation.
Natasha B. Leighl et al., "Patient-reported outcomes from FLAURA: Osimertinib versus erlotinib or gefitinib in patients with EGFR-mutated advanced non-small-cell lung cancer", European Journal of Cancer, vol. 125, Dec. 12, 2019, pp. 49-57.

* cited by examiner

AZAAROMATIC AMIDE DERIVATIVES FOR THE TREATMENT OF CANCER

FIELD OF THE INVENTION

Provided herein is a pyrimidine derivative having the activity of regulating ErbB family kinases. Specifically, the present application relates to the preparation method and use of azaaromatic amide compounds. The present application relates to an azaaromatic amide compound and pharmaceutically acceptable salt thereof, the compound or salt thereof can be used to treat or prevent a disease or disorder by regulating certain mutant forms of epidermal growth factor receptors. The present application also relates to a pharmaceutical composition comprising the compound or salt thereof, and a method for treating various diseases mediated by EGFR, or HER2, or HER4 by using the compound and salt thereof, including non-small cell lung cancer.

BACKGROUND OF THE INVENTION

In the field of anticancer drugs, there is always a need for new anticancer compounds with better activity/selectivity. It is known that EGFR, HER2 and HER4 are members of the transmembrane protein tyrosine kinase of the erbB receptor family, homodimerization and/or heterodimerization of the erbB receptor leads to phosphorylation of certain tyrosine residues in the intracellular domain, and activates various intracellular signaling pathways involved in cell proliferation and survival, including PI3K-AKT-mTOR signaling pathway and RAS-RAF-MEK-ERK signaling pathway. Dysregulation of erbB family signaling can lead to cell proliferation, invasion, metastasis, and angiogenesis, and has been reported in cancers such as lung cancer, head and neck cancer, and breast cancer. For example, in the New England Journal of Medicine, 2008, No. 358, pages 1160-1174 in 2008 and Biochemical and Biophysical Research Communications, 2004, Vol. 319, pages 1-11, it gives a review of erbB receptor signaling and its involvement in tumorigenesis. Therefore, as the target of anti-cancer drug development, many drugs targeting EGFR or HER2 or HER4 are currently in clinical use.

It is reported that approximately 35% of patients with non-small cell lung cancer (NSCLC) in Asia have tumor-associated EGFR mutations (New England Journal of Medicine, 2004, issue 350, page 2129). The majority of EGFR mutations occur in exons 18-21 encoding the kinase domain, and these mutations are usually heterozygotes with mutant allele copy number amplification, of which 90% of EGFR mutations are due to exon 19 deletion or exon 21 L858R missense. These most common EGFR activating mutations (exon 21 L858R missense and exon 19 deletion delE746_A750) have increased affinity for small-molecule tyrosine kinase inhibitors (e.g., Gefitinib and Erlotinib) and decreased affinity for adenosine triphosphate (ATP) relative to wild-type (WT) EGFR. Finally, acquired resistance to Gefitinib and Erlotinib treatment is developed, such as mutations in EGFR exon 20 due to gatekeeper mutation T790M. EGFR mutations also include the co-occurrence of two or more of the above mutations, for example: DT mutation means T790M missense and exon 19 deletion (delE746_A750); LT mutation means T790M and L858R missense.

In non-small cell lung cancer, the frequency of EGFR exon 20 insertion mutations varies from 4-9.2% (Nature Reviews, 2017, No. 17, page 637), and the vast majority of EGFR exon 20 insertion occur in the coding region between amino acid 767-774, including A767, S768, D770, P772, and H773. These EGFR exon 20 insertion mutations have varying degrees of reduced affinity of is clinically approved reversible or irreversible EGFR kinase inhibitors such as Gefitinib, Erlotinib, Afatinib, Osimertinib, etc., as a result, this mutation produces resistance to existing EGFR targeted drugs. There is still a need in the art for new compounds that can effectively inhibit mutations including EGFR exon 20 insertion, and to conduct research and development of new drugs against this unmet clinical need. In other words, there is a need in the art for compounds that exhibit high inhibition of exon 20-inserted EGFR mutants while exhibiting relatively low inhibition of wild-type EGFR, so as to not only exert anticancer efficacy, but also reduce adverse reactions and toxicology associated with the inhibition of wild-type EGFR (e.g., rash and/or diarrhea).

Overexpression of HER2 often occurs in breast cancer, ovarian cancer, bladder cancer, and non-small cell lung cancer. In the current clinical treatment plan, although Herceptin can be used to target HER2 to treat HER2-amplified breast cancer, there are still some HER2-positive breast cancer patients who do not respond to Herceptin, which may be caused by HER2 resistance. In addition, in 2-4% of non-smokers with non-small cell lung cancer, HER2 Exon 20 inserts the amino acid sequence YVMA, making these patients resistant to known HER2 inhibitors. Therefore, there is also a lack of effective drugs that target the HER2 exon 20 insertion mutations.

HER4 has also been shown to have mutations or amplifications associated with cancer, especially small cell lung cancer. In addition, HER4 has a certain impact on the treatment and prognosis of breast cancer. According to statistics, HER4 mutations exist in 1-2% of East Asian cancer patients. However, at present, there is still a lack of effective drugs targeting HER4 in clinical practice.

In order to solve this problem, the inventors have surprisingly found a class of azaaromatic amide compounds, which have a high inhibitory activity against EGFR exon 20 insertion mutations, and some compounds have shown high inhibitory activity against exon 20 point mutations (e.g., S768I, L861Q), HER2 exon 20 insertion mutations and HER4.

SUMMARY OF THE INVENTION

In one aspect, provided herein is a compound of formula (I) or a pharmaceutically acceptable salt thereof.

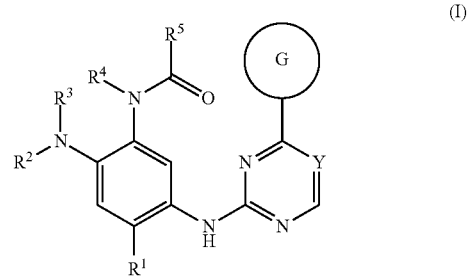

wherein
Y is selected from C, N, C—CF$_3$, and C—Cl;
G is selected from aryl, heteroaryl, or heterocyclyl, preferably C$_{6-10}$ aryl, C$_{5-10}$ heteroaryl, or C$_{4-10}$ heterocyclyl, and wherein the aryl, heteroaryl or heterocyclyl is optionally substituted by one or more substituents independently selected from C$_{1-6}$ alkyl, C$_{1-6}$ alkoxy, oxo, halogen, or C$_{1-6}$ haloalkyl;

R$^1$ is selected from hydrogen, C$_{1-6}$ alkyl, C$_{1-6}$ alkoxy, halogen, C$_{1-6}$ haloalkyl, or C$_{1-6}$ haloalkoxy;

R$^2$ is selected from C$_{1-6}$ alkyl, C$_{1-6}$ heteroalkyl, C$_{6-10}$ aryl, C$_{5-10}$ heteroaryl, C$_{4-10}$ heterocyclyl, C$_{6-10}$ aryl-C$_{1-6}$ alkylene, C$_{5-10}$ heteroaryl-C$_{1-6}$ alkylene, or C$_{4-10}$ heterocyclyl-C$_{1-6}$ alkylene, wherein the alkyl, aryl, heteroaryl, or heterocyclyl is optionally substituted by one or more substituents independently selected from C$_{1-6}$ alkyl, C$_{1-6}$ alkoxy, C$_{1-6}$ alkylamino, di-C$_{1-6}$ alkylamino, oxo, halogen, C$_{1-6}$ haloalkyl, aminoacyl, C$_{1-6}$ alkylaminoacyl, or di-C$_{1-6}$ alkylaminoacyl;

R$^3$ is selected from hydrogen or C$_{1-6}$ alkyl;

or R$^2$ and R$^3$ together with the nitrogen atom to which they are attached form a heteroaryl or heterocyclyl, preferably a C$_{3-10}$ heterocyclyl, wherein the heteroaryl or heterocyclyl is optionally substituted by one or more substituents independently selected from C$_{1-6}$ alkyl, C$_{1-6}$ alkoxy, C$_{1-6}$ alkylamino, di-C$_{1-6}$ alkylamino, oxo, halogen, C$_{1-6}$ haloalkyl, aminoacyl, C$_{1-6}$ alkylaminoacyl, or di-C$_{1-6}$ alkylaminoacyl;

R$^4$ is selected from hydrogen or C$_{1-6}$ alkyl;

R$^5$ is selected from the following groups:

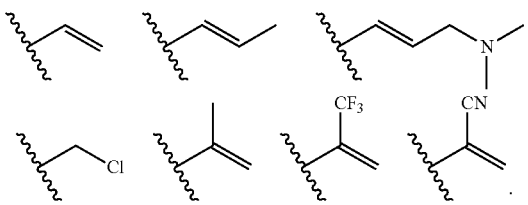

In another aspect, provided herein is also a method for preparing the compound of formula (I) as described above or a pharmaceutically acceptable salt thereof.

In another aspect, provided herein is a pharmaceutical composition comprising the compound of formula (I) as described above or a pharmaceutically acceptable salt thereof and a pharmaceutically acceptable diluent or carrier.

In another aspect, provided herein is the compound of formula (I) as described above or a pharmaceutically acceptable salt thereof for use as a medicament.

In another aspect, provided herein is also a method for producing an anticancer effect in a warm-blooded animal, such as a human, in need of such treatment, which comprises: administering to the animal an effective amount of the compound of formula (I) as described above or a pharmaceutically acceptable salt thereof.

In another aspect, provided herein is also use of the compound as described above or a pharmaceutically acceptable salt thereof in the preparation of a medicament for treating cancer.

In another aspect, provided herein is also use of the compound as described above or a pharmaceutically acceptable salt thereof in the preparation of a medicament for inhibiting the EGFR (also called HER1) or HER2 pathway.

In another aspect, the present invention provides a compound of formula (II) or a pharmaceutically acceptable salt thereof:

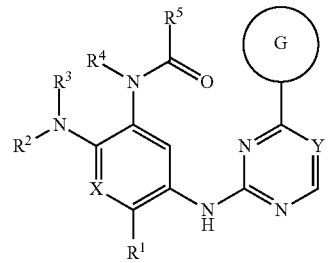

(II)

wherein

Y is selected from C, N, C—CF$_3$, and C—Cl;

X is selected from C and N;

G is selected from aryl, heteroaryl or heterocyclyl, preferably C$_{6-10}$ aryl, C$_{5-10}$ heteroaryl, or C$_{4-10}$ heterocyclyl, and wherein the aryl, heteroaryl, or heterocyclyl is optionally substituted by one or more substituents independently selected from C$_{1-6}$ alkyl, C$_{1-6}$ alkoxy, oxo, halogen, C$_{6}$-C$_{10}$ aryl, C$_{5-10}$ heteroaryl or C$_{4-10}$ heterocyclyl, C$_{1-6}$ haloalkyl or C$_{1}$-C$_{6}$ aminealkyl;

R$^1$ is selected from hydrogen, C$_{1-6}$ alkyl, C$_{1-6}$ alkoxy, halogen, C$_{1-6}$ haloalkyl, or C$_{1-6}$ haloalkoxy;

R$^2$ is selected from C$_{1-6}$ alkyl, C$_{1-6}$ heteroalkyl, C$_{6-10}$ aryl, C$_{5-10}$ heteroaryl, C$_{4-10}$ heterocyclyl, C$_{6-10}$ aryl-C$_{1-6}$ alkylene, C$_{5-10}$ heteroaryl-C$_{1-6}$ alkylene, or C$_{4-10}$ heterocyclyl-C$_{1-6}$ alkylene, wherein the alkyl, aryl, heteroaryl or heterocyclyl is optionally substituted by one or more substituents independently selected from C$_{1-6}$ alkyl, C$_{1-6}$ alkoxy, C$_{1-6}$ alkylamino, di-C$_{1-6}$ alkylamino, oxo, halogen, C$_{1-6}$ haloalkyl, aminoacyl, C$_{1-6}$ alkylaminoacyl, or di-C$_{1-6}$ alkylaminoacyl;

R$^3$ is selected from hydrogen or C$_{1-6}$ alkyl;

or R$^2$ and R$^3$ together with the nitrogen atom to which they are attached form a heteroaryl or heterocyclyl, preferably a C$_{3-10}$ heterocyclyl, wherein the heteroaryl or heterocyclyl is optionally substituted by one or more substituents independently selected from C$_{1-6}$ alkyl, C$_{1-6}$ alkoxy, C$_{1-6}$ alkylamino, di-C$_{1-6}$ alkylamino, oxo, halogen, C$_{1-6}$ haloalkyl, aminoacyl, C$_{1-6}$ alkylaminoacyl, or di-C$_{1-6}$ alkylaminoacyl;

R$^4$ is selected from hydrogen or C$_{1-6}$ alkyl;

R$^5$ is selected from the following groups:

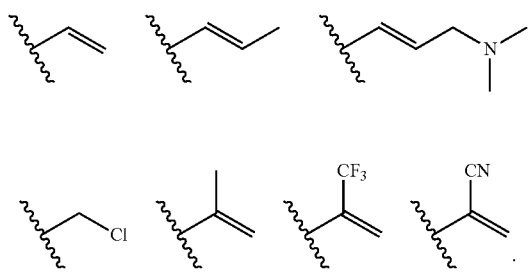

In another aspect, the present invention provides a compound of formula (III) or a pharmaceutically acceptable salt thereof:

(III)

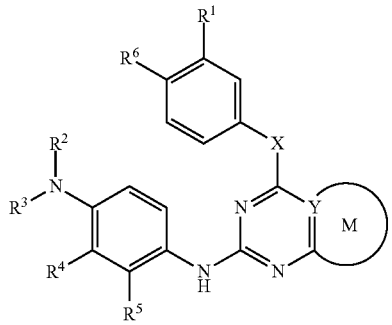

Y is selected from C;
X is selected from CH$_2$, NH, and O;
M and pyrimidine ring (Y=C) form a fused heteroaryl or heterocyclyl, wherein M is selected from a heteroaryl or heterocyclyl fused to a pyrimidine ring, preferably C$_5$-C$_{10}$ heteroaryl including pyrimidine ring, C4-C10 heterocyclyl; and the heteroaryl or heterocyclyl is optionally substituted by one or more substituents independently selected from C1-6 alkyl, C1-6 alkoxy, oxo, halogen, or C1-6 haloalkyl;
alternatively, when M does not form a fused heteroaryl or heterocyclyl with a pyrimidine ring (Y=C), then Y is selected from C—Cl and C—CF$_3$;
R$^1$ is selected from the following groups:

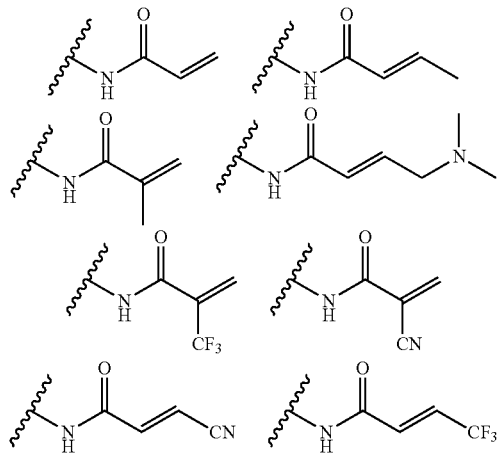

R$^3$ is selected from hydrogen or C$_{1-6}$ alkyl;
or R$^2$ and R$^3$ together with the nitrogen atom to which they are attached form a heteroaryl or heterocyclyl, preferably a C3-10 heterocyclyl; wherein the heteroaryl or heterocyclyl is optionally substituted by one or more substituents independently selected from C1-6 alkyl, C1-6 alkoxy, C1-6 alkylamino, di-C1-6 alkylamino, oxo, halogen, C1-6 haloalkyl, aminoacyl, C1-6 alkylaminoacyl, or di-C1-6 alkylaminoacyl;
R$^4$, R$^5$ and R$^6$ are selected from hydrogen, nitro, cyano, hydroxy, halogen, C1-6 alkyl, C1-6 alkoxy, C1-6 haloalkyl or C1-6 haloalkoxy, alkylacyl, C1-6 alkylacyl, alkoxyacyl, C1-C6 alkoxyacyl, aminoacyl, or C1-6 alkylaminoacyl.

In another aspect, the present invention provides a compound of formula (IV) or a pharmaceutically acceptable salt thereof:

(IV)

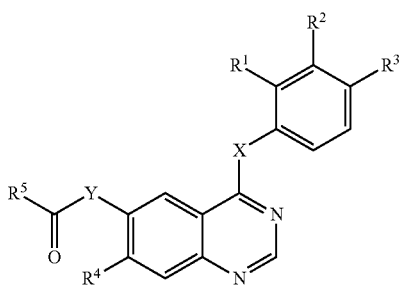

X and Y are selected from O and NH;
R$^1$, R$^2$, R$^3$ and R$^4$ are selected from hydrogen, nitro, cyano, hydroxy, halogen, C1-6 alkyl, C1-6 alkoxy, C1-6 haloalkyl or C1-6 haloalkoxy, alkylacyl, C1-6 alkylacyl, alkoxyacyl, C1-C6 alkoxyacyl, aminoacyl, or C1-6 alkylaminoacyl;
R$^5$ is selected from C3-10 heterocyclyl, wherein the heteroaryl or heterocyclyl is optionally substituted by one or more substituents independently selected from C1-6 alkyl, C1-6 alkoxy, C1-6 alkylamino, di-C1-6 alkylamino, oxo, halogen, C1-6 haloalkyl, aminoacyl, C1-6 alkylaminoacyl, or di-C1-6 alkylaminoacyl.

In another aspect, the present invention provides a compound of formula (V) or a pharmaceutically acceptable salt thereof:

(V)

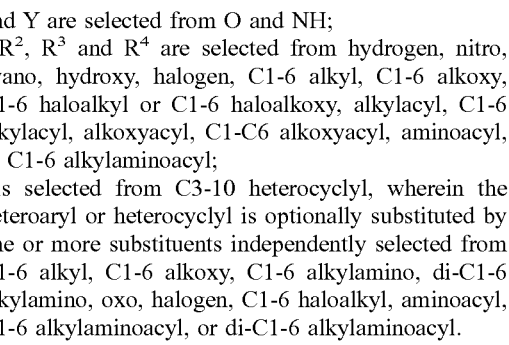

wherein
X is selected from C and N;
R$^1$, R$^2$, R$^3$, R$^4$, and R$^5$ are selected from hydrogen, nitro, cyano, hydroxy, halogen, C1-6 alkyl, C1-6 alkoxy, C1-6 haloalkyl or C1-6 haloalkoxy, alkylacyl, C1-6 alkylacyl, alkoxyacyl, C1-C6 alkoxyacyl, aminoacyl, or C1-6 alkylaminoacyl;
n is selected from 1, 2, 3, and 4;
R$^6$ is selected from the following groups:

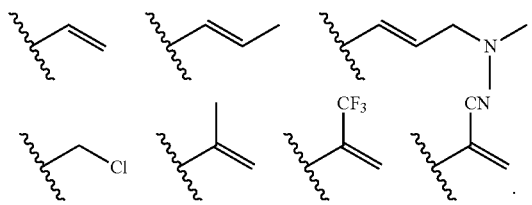

In another aspect, the present invention also provides a method for producing an anticancer effect in a warm-blooded animal such as a human in need of such treatment, which comprises: administering to the animal an effective amount of the compound of the formula (II), formula (III), formula (IV) and formula (V) as described above or pharmaceutically acceptable salts thereof.

In another aspect, the present invention also provides use of the compound of formula (II), formula (III), formula (IV) and formula (V) as described above or pharmaceutically acceptable salts thereof and an additional antitumor substance for the simultaneous, independent or sequential treatment of cancer.

In another aspect, provided herein is a pharmaceutical composition, which comprises the compound of formula (II), formula (III), formula (IV), and formula (V) as described above or pharmaceutically acceptable salts thereof and a pharmaceutically acceptable diluent or carrier.

In another aspect, provided herein is the compound of formula (II) as described above or a pharmaceutically acceptable salt thereof, for use as a medicament.

In another aspect, provided herein is also a method for producing an anticancer effect in a warm-blooded animal such as a human in need of such treatment, which comprises: administering to the animal an effective amount of the compounds of formula (II), formula (III) formula (IV) and formula (V) as described above or pharmaceutically acceptable salts thereof. In another aspect, provided herein is also an EGFR exon 20 insertion mutation inhibitor and/or HER2 exon 20 insertion mutation inhibitor and/or HER4 kinase inhibitor, which comprises the compounds of formula (II), formula (III), formula (IV) and formula (V) as described above, or pharmaceutically acceptable salts thereof.

In another aspect, provided herein is also use of the compounds of formula (II), formula (III) formula (IV) and formula (V) as described above or pharmaceutically acceptable salts thereof in the preparation of an EGFR exon 20 mutation inhibitor, and/or a HER2 exon 20 mutation inhibitor, and/or a HER4 kinase inhibitor.

In another aspect, provided herein is also the composition as described above for inhibiting the activity of EGFR kinase with EGFR exon 20 mutation, and/or the activity of HER2 kinase with exon 20 mutation, and/or the activity of HER4 kinase with exon 20 mutation.

In a preferred embodiment, provided herein is also a method for inhibiting the EGFR or HER2 or HER4 pathway, which comprises: administering the compound described herein to a subject in need thereof.

In a preferred embodiment, the cancer is selected from: ovarian cancer, non-small cell lung cancer, small cell lung cancer, cervical cancer, colorectal cancer, breast cancer, pancreatic cancer, glioma, glioblastoma, melanoma, prostate cancer, leukemia, lymphoma, non-Hodgkin's lymphoma, gastric cancer, lung cancer, hepatocellular carcinoma, gastric cancer, gastrointestinal stromal tumor, thyroid cancer, cholangiocarcinoma, endometrial cancer, kidney cancer, anaplastic large cell lymphoma, acute myeloid leukemia, multiple myeloma, melanoma, and mesothelioma.

In a preferred embodiment, the cancer is non-small cell lung cancer.

In a preferred embodiment, provided herein is also a method for treating cancer, which comprises: administering the compound described herein to a subject in need thereof.

In a preferred embodiment, provided herein is also a method of inhibiting the EGFR (also known as HER1) or HER2 or HER4 pathway, which comprises: administering the compound described herein to a subject in need thereof.

In the above embodiments, the subject may be a mammal or a human.

DETAIL DESCRIPTION OF THE INVENTION

Definitions

Herein, the following terms have the following meanings:

The term "alkyl" alone or in combination with other groups means a linear or branched chain monovalent saturated hydrocarbon group composed of carbon and hydrogen atoms. "$C_{1-6}$ alkyl" means a branched or linear chain alkyl having 1 to 6 carbon atoms, such as methyl, ethyl, n-propyl, isopropyl, n-butyl, sec-butyl, tert-butyl, n-hexyl.

The term "alkylene" alone or in combination with other groups means a linear or branched chain divalent saturated hydrocarbon group composed of carbon and hydrogen atoms. "$C_{1-6}$ alkylene" means a branched or linear chain alkyl having 1 to 6 carbon atoms, such as methylene, ethylene, propylene, and the like.

The term "alkoxy" alone or in combination with other groups means the group R'—O—, where R' is an alkyl group as described above. "$C_{1-6}$ alkoxy" means the group R'—O—, wherein R' is $C_{1-6}$ alkyl as described above.

"Halogen" means fluorine, chlorine, bromine or iodine.

"Haloalkyl" means an alkyl as defined above substituted with one or more halogens, for example $C_{1-6}$ haloalkyl. Non-limiting examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. Perhaloalkyl refers to an alkyl group in which all hydrogen atoms are replaced by halogen atoms, such as trifluoromethyl.

"Haloalkoxy" means one or more alkyl groups (R'—O—) as defined above substituted with halogen, wherein R' is an alkyl group as described above, for example, $C_{1-6}$ haloalkoxy. Non-limiting examples of haloalkoxy include fluoromethoxy, difluoromethoxy, chloromethoxy, dichloromethoxy, and the like.

The term "cycloalkyl" refers to a 4-7 membered monocyclic saturated hydrocarbon ring system. The cycloalkyl group can be optionally substituted with one or more substituents as defined herein. Cycloalkyl includes cyclobutyl, cyclopentyl, cyclohexyl and cycloheptyl.

The term "cycloalkenyl" refers to a 5-7 membered monocyclic unsaturated (but non-aromatic) hydrocarbon ring system. The cycloalkenyl group can be optionally substituted with one or more substituents as defined herein. Cycloalkenyl includes cyclopentenyl, cyclohexenyl and cycloheptenyl.

The term "aryl" refers to a monocyclic or fused bicyclic aromatic ring containing carbon atoms. "$C_{6-10}$ aryl" refers to an aryl group containing 6-10 carbon atoms. For example, $C_{6-10}$ aryl may be phenyl or naphthyl.

As used herein, the term "heteroatom" refers to nitrogen (N), oxygen (O), and sulfur (S) atoms. The terms "heteroalkyl" and "heteroalkylene" refer to alkyl and alkylene groups as described above, in which one or more carbon atoms are replaced by heteroatoms.

As used herein, unless otherwise indicated, the term "heteroaryl" refers to a 5-10 membered monocyclic aromatic ring system or a bicyclic fused aromatic ring system having 1-4 heteroatoms. Heteroaryl can also refer to an 8-10 membered ring system, wherein the heteroaryl ring is fused to a phenyl, cycloalkyl, cycloalkenyl or heterocyclyl ring, wherein the linking group or point of attachment is on the heteroaryl ring. Non-limiting examples of heteroaryl groups comprise: 2- or 3-thienyl; 2- or 3-furyl; 2- or 3-pyrrolyl; 2-, 4- or 5-imidazolyl; 3-, 4- or 5-pyrazolyl; 2-, 4- or 5-thiazolyl; 3-, 4- or 5-isothiazolyl; 2-, 4- or 5-oxazolyl; 3-, 4- or 5-isoxazolyl; 3- or 5-1,2,4-triazolyl; 4- or 5-1,2,3-triazolyl; furazyl; thiadiazolyl; tetrazolyl; 2-, 3- or 4-pyridinyl; 3- or 4-pyridazinyl; 3-, 4- or 5-pyrazinyl; 2-pyrazinyl and 2-, 4- or 5-pyrimidinyl; 1-, 2-, 3-, 5-, 6-, 7- or 8-indazinyl; 1-, 3-, 4-, 5-, 6- or 7-isoindolyl; 2-, 3-, 4-, 5-, 6- or 7-indolyl; 2-, 3-, 4-, 5-, 6- or 7-indazolyl; 2-, 4-, 5-, 6-, 7- or 8-purinyl; 1-, 2-, 3-, 4-, 6-, 7-, 8- or 9-quinazinyl; 2-, 3-, 4-, 5-, 6-, 7- or 8-quinolinyl; 1-, 3-, 4-, 5-, 6-, 7- or 8-isoquinolinyl; 1-, 4-, 5-, 6-, 7- or 8-phthalazinyl; 2-, 3-, 4-, 5- or 6-naphthyridinyl; 2-, 3-, 5-, 6-, 7- or 8-quinazolinyl; 3-, 4-, 5-, 6-, 7- or 8-cinnolinyl; 2-, 4-, 6- or 7-pteridinyl; 1-, 2-, 3-, 4-, 5-, 6-, 7- or 8-4aH carbazolyl; 1-, 2-, 3-, 4-, 5-, 6-, 7- or 8-carbazolyl; 1-, 3-, 4-, 5-, 6-, 7-, 8- or 9-carboline; 1-, 2-, 3-, 4-, 6-, 7-, 8-, 9- or 10-phenanthridinyl; 1-, 2-, 3-, 4-, 5-, 6-, 7-, 8- or 9-acridinyl; 1-, 2-, 4-, 5-, 6-, 7-, 8- or 9-naphthalene diazaphenyl; 2-, 3-, 4-, 5-, 6-, 8-, 9- or 10-phenanthroline; 1-, 2-, 3-, 4-, 6-, 7-, 8- or 9-phenazinyl; 1-, 2-, 3-, 4-, 6-, 7-, 8-, 9- or -phenothiazine; 1-, 2-, 3-, 4-, 6-, 7-, 8-, 9- or 10-phenoxazinyl; 2-, 3-, 4-, 5-, 6- or 1-, 3-, 4-, 5-, 6-, 7-, 8-, 9- or 10-benzisoquinolinyl; 2-, 3-, 4- or thieno[2,3-b]furanyl; 2-, 3-, 5-, 6-, 7-, 8-, 9-, 10- or 11-7H-pyrazino[2,3-c]carbazolyl; 2-, 3-, 5-, 6- or 7-2H-furano[3,2-b]-pyranyl; 2-, 3-, 4-, 5-, 7- or 8-5H-pyrido[2,3-d]-o-oxazinyl; 1-, 3- or 5-1H-pyrazolo[4,3-d]-oxazolyl; 2-, 4- or 54H-imidazo [4,5-d]thiazolyl; 3-, 5- or 8-pyrazino[2,3-d]pyridazinyl; 2-, 3-, 5- or 6-imidazo[2,1-b]thiazolyl; 1-, 3-, 6-, 7-, 8- or 9-furano[3,4-c]cinnoyl; 1-, 2-, 3-, 4-, 5-, 6-, 8-, 9-, 10 or 11-4H-pyrido[2,3-c] carbazolyl; 2-, 3-, 6- or 7-imidazo[1,2-b] [1,2,4]triazinyl; 7-benzo[b]thienyl; 2-, 4-, 5-, 6- or 7-benzooxazolyl; 2-, 4-, 5-, 6- or 7-benzimidazolyl; 2-, 4-, 4-, 5-, 6- or 7-benzithiazolyl; 2-, 4-, 5-, 6-, 7- or 8-benzoxazinyl. Generally fused heteroaryl groups also include, but are not limited to, 2-, 3-, 4-, 5-, 6-, 7- or 8-quinolinyl; 1-, 3-, 4-, 5-, 6-, 7- or 8-isoquinolinyl; 2-, 3-, 4-, 5-, 6- or 7-indolyl; 2-, 3-, 4-, 5-, 6- or 7-benzo[b]thienyl; 2-, 4-, 5-, 6- or 7-benzoxazolyl; 2-, 4-, 5-, 6- or 7-benzimidazolyl; 2-, 4-, 5-, 6- or 7-benzothiazolyl; cycloheptadio[d]imidazolyl; 7,8-dihydro-5H-pyrano[4,3-d]pyrimidinyl; 1H-pyrazolo[3,4-d]pyrimidinyl; thieno[3,2-d]pyrimidinyl; 6,7-dihydro-5H-cyclopentadiopyrimidinyl; 5,6-dihydro-thiazolo[2,3-c][1,2,4]triazolyl; [1,2,4]triazolo[4,3-a]pyridinyl; 7,8-dihydro-5H-pyrano[3,4-d]pyridazinyl; and isoxazolo[5,4-b]pyridinyl.

Unless otherwise indicated, heteroaryl groups containing more than one heteroatom may contain different heteroatoms. Heteroaryl groups can be optionally substituted with one or more substituents as defined herein.

The term "heterocyclyl" as used herein refers to a 4-10 membered monocyclic or bicyclic saturated or unsaturated ring containing 1-4 heteroatoms, including a bridged heterocyclic ring or spiro ring.

The heterocyclyl is not aromatic. The heterocyclyl containing more than one heteroatom may contain different heteroatoms. The heterocyclyl group can be optionally substituted with one or more substituents as defined herein. Examples of the heterocyclyl include tetrahydrofuran, dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, azetidine, oxathiolane, dithiolane, 1,3-dioxane, 1,3-dithiane, oxathiolane, thiomorpholine, etc. The heterocyclyl may be directly connected to other parts of the molecule, or may be connected through a $C_{1-6}$ alkylene or a $C_{1-6}$ heteroalkylene chain.

When any group or moiety (e.g., alkyl, aryl, heteroaryl, or heterocyclyl) is defined herein as "being optionally substituted with one or more substituents independently selected from", it should be understood that the groups or moieties are unsubstituted or substituted with one, one or two, or one to three substituents, wherein each substituent is independently selected from the group of the substituents.

Herein, examples of the optionally substituted heteroaryl or heterocyclyl include, but are not limited to, 4,5,6,7-tetrahydropyrazolo[1,5-a]pyridin-3-yl, 1H-indol-3-yl, 1-methyl-1H-indol-3-yl and pyrazolo[1,5-a]pyridin-3-yl, (3R)-3-(dimethylamino)pyrrolidin-1-yl, (3S)-3-(dimethylamino)pyrrolidin-1-yl, 3-(dimethylamino)azetidine-1-yl, 5-methyl-2,5-diazaspiro[3.4]octan-2-yl, (3aR,6aR)-5-methylhexahydro-pyrrolo[3,4-b]pyrrole-1(2H)-yl, 1-methyl-1,2,3,6-tetrahydropyridin-4-yl, 4-methylpiperazin-1-yl, 4-[2-(dimethylamino)-2-oxoethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl, or 4-[(2S)-2-aminopropionyl] piperazin-1-yl.

The term "acyl" refers to the group —CO—R, wherein R is alkyl, aryl, heteroaryl or heterocyclyl as described above.

The term "oxo" refers to a group (=O).

In the context of this specification, unless indicated to the contrary, the term "treatment" also includes "prevention". The term "treatment" as used herein is intended to have its ordinary meaning as follows: treating a disease to completely or partially relieve one, some, or all of its symptoms, or correcting or compensating for underlying pathology. The term "prevention" as used herein is intended to have its normal daily meaning and includes primary prevention to prevent the development of the disease and secondary prevention to prevent the occurrence of the disease, temporary or continuous prevention of the exacerbation or deterioration of the patient's disease or the occurrence of disease-related new symptoms.

The Compounds of the Present Application

In one aspect, provided herein is a compound of formula (I) or a pharmaceutically acceptable salt thereof:

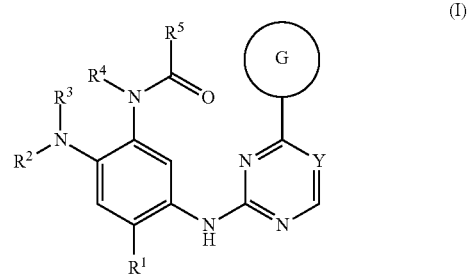

wherein
Y is selected from C, N, C—CF$_3$, and C—Cl;
G is selected from aryl, heteroaryl, or heterocyclyl, preferably $C_{6-10}$ aryl, $C_{5-10}$ heteroaryl, or $C_{4-10}$ heterocyclyl, and wherein the aryl, heteroaryl or heterocyclyl is optionally substituted by one or more substituents independently selected from $C_{1-6}$ alkyl, $C_{1-6}$ alkoxy, oxo, halogen, or $C_{1-6}$ haloalkyl;

$R^1$ is selected from hydrogen, $C_{1-6}$ alkyl, $C_{1-6}$ alkoxy, halogen, $C_{1-6}$ haloalkyl, or $C_{1-6}$ haloalkoxy;

$R^2$ is selected from $C_{1-6}$ alkyl, $C_{1-6}$ heteroalkyl, $C_{6-10}$ aryl, $C_{5-10}$ heteroaryl, $C_{4-10}$ heterocyclyl, $C_{6-10}$ aryl-$C_{1-6}$ alkylene, $C_{5-10}$ heteroaryl-$C_{1-6}$ alkylene, or $C_{4-10}$ heterocyclyl-$C_{1-6}$ alkylene, wherein the alkyl, aryl, heteroaryl, or heterocyclyl is optionally substituted by one or more substituents independently selected from $C_{1-6}$ alkyl, $C_{1-6}$ alkoxy, $C_{1-6}$ alkylamino, di-$C_{1-6}$ alkylamino, oxo, halogen, $C_{1-6}$ haloalkyl, aminoacyl, $C_{1-6}$ alkylaminoacyl, or di-$C_{1-6}$ alkylaminoacyl; $R^3$ is selected from hydrogen or $C_{1-6}$ alkyl;

or $R^2$ and $R^3$ together with the nitrogen atom to which they are attached form a heteroaryl or heterocyclyl, preferably a $C_{3-10}$ heterocyclyl, wherein the heteroaryl or heterocyclyl is optionally substituted by one or more substituents independently selected from $C_{1-6}$ alkyl, $C_{1-6}$ alkoxy, $C_{1-6}$ alkylamino, di-$C_{1-6}$ alkylamino, oxo, halogen, $C_{1-6}$ haloalkyl, aminoacyl, $C_{1-6}$ alkylaminoacyl, or di-$C_{1-6}$ alkylaminoacyl;

$R^4$ is selected from hydrogen or $C_{1-6}$ alkyl;

$R^5$ is selected from the following groups:

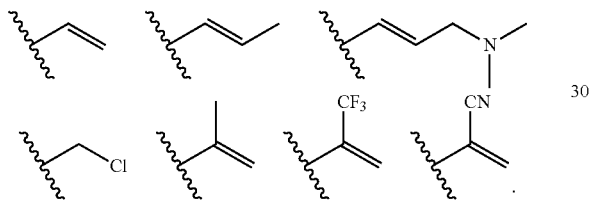

In a preferred embodiment, $R^2$ and $R^3$ together with the nitrogen atom to which they are attached form a group selected from: (3R)-3-(dimethylamino)pyrrolidin-1-yl, (3S)-3-(dimethylamino)pyrrolidin-1-yl, 3-(dimethylamino)azetidine-1-yl, [2-(dimethylamino)ethyl]-(methyl)amino, [2-(methylamino)ethyl](methyl)amino, 5-methyl-2,5-diazaspiro[3.4]oct-2-yl, (3aR,6aR)-5-methylhexahydro-pyrrolo[3,4-b]pyrrol-1(2H)-yl, 1-methyl-1,2,3,6-tetrahydropyridin-4-yl, 4-methylpiperazin-1-yl, 4-[2-(di-methylamino)-2-oxoethyl]piperazin-1-yl, methyl[2-(4-methylpiperazin-1-yl)ethyl]amino, methyl[2-(morpholine-4-yl)ethyl]amino, 1-amino-1,2,3,6-tetrahydropyridin-4-yl, or 4-[(2S)-2-aminopropionyl]piperazin-1-yl.

In a more preferred embodiment, provided herein is a compound of formula (I) or a pharmaceutically acceptable salt thereof:

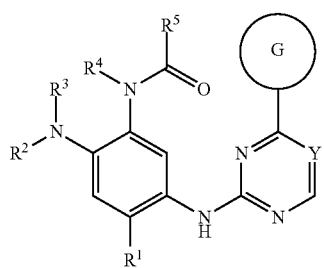

(I)

wherein
Y is selected from C, N, C—$CF_3$, and C—Cl;

G is selected from 4,5,6,7-tetrahydropyrazolo[1,5-a]pyridin-3-yl, 3,3-dimethyl-2,3-dihydro-1H-pyrrolo[3,2-b]pyridin-1-yl, 1H-pyrrolo[3,2-b]pyridin-1-yl, 1H-indol-3-yl, 3-methyl-1H-indol-1-yl, 1H-benzo[d]imidazol-1-yl, 1H-indazol-1-yl, 1H-pyrrolo[3,2-c]pyridin-1-yl, 3-methyl-1H-indazol-1-yl, 5-fluoro-3-methyl-1H-indazol-1-yl, 3-methyl-1H-pyrrolo[3,2-c]pyridin-1-yl, 1H-pyrrolo[3,2-c]pyridin-1-yl, 1H-benzo[d][1,2,3]triazol-1-yl, 6-fluoro-3-methyl-1H-indazol-1-yl, 8-methyl-imidazo[1,2-a]pyridin-3-yl, 8-fluoro-imidazo[1,2-a]pyridin-3-yl, 8-trifluoromethyl-imidazo[1,2-a]pyridin-3-yl, 1H-pyrrolo[3,2-c]pyridin-1-yl, 3-fluoro-1H-indazol-1-yl, 1-methyl-1H-indol-3-yl, pyrazolo[1,5-a]pyridin-3-yl and 8-iodo-imidazo[1,2-a]pyridin-3-yl, 4-chloro-3-methoxyphenoxy, 5-methoxy-1-methyl-1H-indol-3-yl, 5-chloro-1-methyl-1H-indol-3-yl, 6-chloro-5-methoxy-1-methyl-1H-indol-3-yl, 5-fluoro-1-methyl-TH-indol-3-yl;

$R^1$ is selected from methoxy, methyl, chlorine, fluorine, difluoromethoxy, trifluoroethoxy, trifluoromethyl;

$R^4$ is hydrogen;

$R^5$ is the following groups:

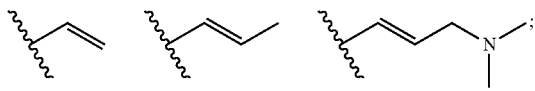

In a more preferred embodiment, Y is selected from C, N.
In a more preferred embodiment, $R^5$ is the following groups:

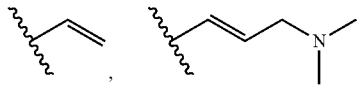

$R^2$ and $R^3$ together with the nitrogen atom to which they are attached form a group selected from: (3R)-3-(dimethylamino)pyrrolidin-1-yl, (3S)-3-(dimethylamino)pyrrolidin-1-yl, 3-(dimethylamino)azetidine-1-yl, [2-(dimethylamino)ethyl]-(methyl)amino, [2-(methylamino)ethyl](methyl)amino, 5-methyl-2,5-diazaspiro[3.4]octan-2-yl, (3aR,6aR)-5-methylhexahydro-pyrrolo[3,4-b]pyrrole-1(2H)-yl, 1-methyl-1,2,3,6-tetrahydropyridin-4-yl, 4-methylpiperazin-1-yl, 4-[2-(dimethylamino)-2-oxoethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl, or 4-[(2S)-2-aminopropionyl]piperazin-1-yl.

In a more preferred embodiment, Y is selected from C, N; $R^5$ is the following groups:

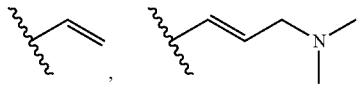

G is selected from 1H-pyrrolo[3,2-c]pyridin-1-yl, 3-fluoro-1H-indazol-1-yl, 8-fluoro-imidazo[1,2-a]pyridin-3-yl, 8-iodo-imidazo[1,2-a]pyridin-3-yl, 8-trifluoromethyl-imidazo[1,2-a]pyridin-3-yl, 4-chloro-3-methoxyphenoxy, 5-methoxy-1-methyl-1H-indol-3-yl, 5-chloro-1-methyl-1H-indol-3-yl, 6-chloro-5-methoxy-1-methyl-TH-indol-3-yl, 5-fluoro-1-methyl-1H-indol-3-yl.

R² and R³ together with the nitrogen atom to which they are attached form a group selected from: (3R)-3-(dimethylamino)pyrrolidin-1-yl, (3S)-3-(dimethylamino)pyrrolidin-1-yl, 3-(dimethylamino)azetidine-1-yl, [2-(dimethylamino)ethyl]-(methyl)amino, [2-(methylamino)ethyl](methyl)amino, 5-methyl-2,5-diazaspiro[3.4]octan-2-yl, (3aR,6aR)-5-methylhexahydro-pyrrolo[3,4-b]pyrrole-1(2H)-yl, 1-methyl-1,2,3,6-tetrahydropyridin-4-yl, 4-methylpiperazin-1-yl, 4-[2-(dimethylamino)-2-oxoethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl, or 4-[(2S)-2-aminopropionyl]piperazin-1-yl.

In a more preferred embodiment, Y is selected from N; R5 is the following groups:

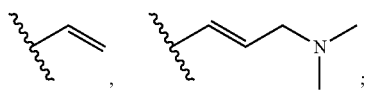

G is selected from 1H-pyrrolo[3,2-c]pyridin-1-yl, 3-fluoro-1H-indazol-1-yl, 8-fluoro-imidazo[1,2-a]pyridin-3-yl, 8-iodo-imidazo[1,2-a]pyridin-3-yl, 8-trifluoromethyl-imidazo[1,2-a]pyridin-3-yl, 4-chloro-3-methoxyphenoxy, 5-methoxy-1-methyl-1H-indol-3-yl, 5-chloro-1-methyl-1H-indol-3-yl, 6-chloro-5-methoxy-1-methyl-1H-indol-3-yl, 5-fluoro-1-methyl-1H-indol-3-yl;

R¹ is selected from methoxy, difluoromethoxy, trifluoroethoxy, trifluoromethyl;

R² and R³ together with the nitrogen atom to which they are attached form a group selected from: (3R)-3-(dimethylamino)pyrrolidin-1-yl, (3S)-3-(dimethylamino)pyrrolidin-1-yl, 3-(dimethylamino)azetidine-1-yl, [2-(dimethylamino)ethyl]-(methyl)amino, [2-(methylamino)ethyl](methyl)amino, 5-methyl-2,5-diazaspiro[3.4]octan-2-yl, (3aR,6aR)-5-methylhexahydro-pyrrolo[3,4-b)pyrrol-1(2H)-yl, 1-methyl-1,2,3,6-tetrahydropyridin-4-yl, 4-methylpiperazin-1-yl, 4-[2-(dimethylamino)-2-oxoethyl]piperazin-1-yl, methyl[2-(4-methylpiperazin-1-yl)ethyl]amino, methyl[2-(morpholine-4-yl)ethyl]amino, 1-amino-1,2,3,6-tetrahydropyridin-4-yl, or 4-[(2S)-2-aminopropionyl]piperazin-1-yl.

According to the compound of formula (I) described in the first aspect herein, it is selected from the following compounds:

(R)—N-(5-((4-(1H-pyrrole[3,2-c]pyridin-1-yl)-1,3,5-triazin-2-yl)amino)-2-(2-((dimethylamino)methyl)azetidin-1-yl)-4-methoxyphenyl) acrylamide (Compound 1);

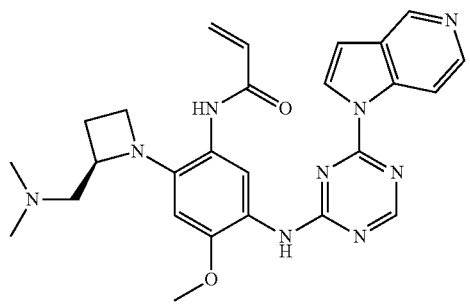 [SMILES: C=CC(=O)Nc1cc(Nc2ncnc(-n3ccc4cnccc43)n2)c(OC)cc1N1CC[C@@H]1CN(C)C]

(R,E)-N-(5-((4-(1H-pyrrole[3,2-c]pyridin-1-yl)-1,3,5-triazin-2-yl)amino)-2-(2-((dimethylamino)methyl)azetidin-1-yl)-4-methoxyphenyl)-4-(dimethylamino)butene-2-amide (Compound 2);

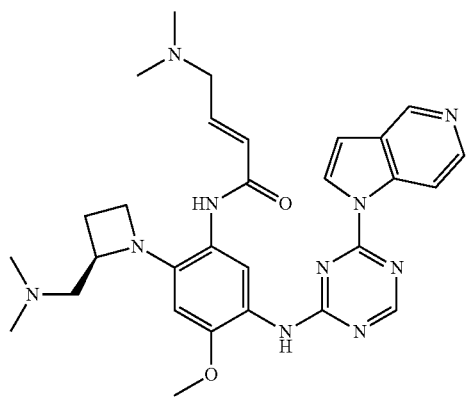 [SMILES: COc1cc(N2CC[C@@H]2CN(C)C)c(NC(=O)/C=C/CN(C)C)cc1Nc1ncnc(-n2ccc3cnccc32)n1]

N-(2-((2-(dimethylamino)ethyl)(methyl)amino)-5-((4-(3-fluoro-TH-indazol-1-yl)-1,3,5-triazin-2-yl)amino)-4-methoxyphenyl) acrylamide (Compound 3);

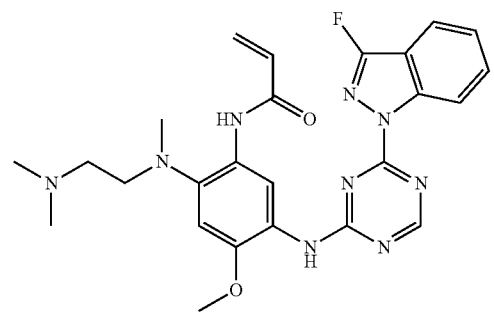 [SMILES: C=CC(=O)Nc1cc(Nc2ncnc(-n3nc(F)c4ccccc43)n2)c(OC)cc1N(C)CCN(C)C]

N-(2-((2-(dimethylamino)ethyl)(methyl)amino)-4-methoxy-5-((4-(8-iodoimidazo[1,2-a]pyridin-3-yl)pyrimidin-2-yl) amino)phenyl) acrylamide (Compound 4);

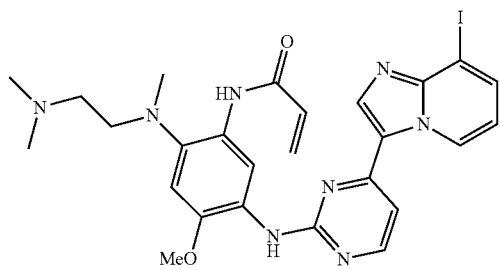 [SMILES: C=CC(=O)Nc1cc(Nc2nccc(-c3cnc4c(I)cccn34)n2)c(OC)cc1N(C)CCN(C)C]

N-(2-((2-(dimethylamino)ethyl)(methyl)amino)-5-((4-(8-fluoroimidazo[1,2-a]pyridin-3-yl)pyrimidin-2-yl)amino)-4-methoxyphenyl)acrylamide (Compound 5);

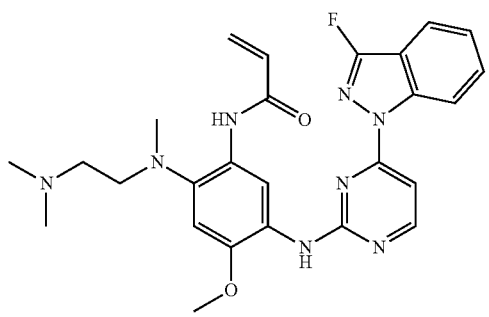

N-(2-((2-(dimethylamino)ethyl)(methyl)amino)-4-methoxy-5-((4-(5-methoxy-1-methyl-1H-indol-3-yl)-1,3,5-triazin-2-yl)amino)phenyl)acrylamide (Compound 8);

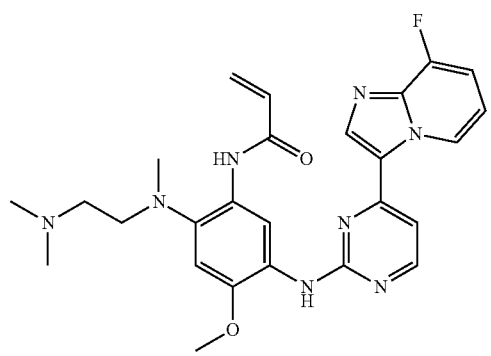

N-(2-((2-(dimethylamino)ethyl)(methyl)amino)-4-methoxy-5-((4-(8-trifluoromethylimidazo[1,2-a]pyridin-3-yl)pyrimidin-2-yl)amino)phenyl)acrylamide (Compound 6);

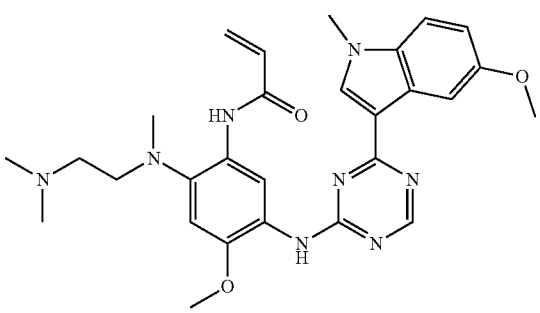

N-(5-((4-(5-chloro-1-methyl-1H-indol-3-yl)-1,3,5-triazin-2-yl)amino)-2-((2-(dimethylamino)ethyl(m ethyl)amino)-4-methoxyphenyl)acrylamide (Compound 9);

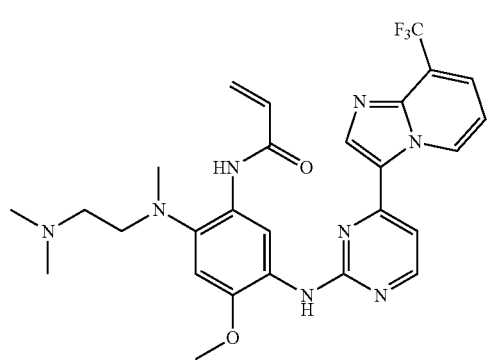 [SMILES: C=CC(=O)Nc1cc(Nc2nccc(-c3cnc4c(C(F)(F)F)cccn34)n2)c(OC)cc1N(C)CCN(C)C]

N-(2-((2-(dimethylamino)ethyl(methyl)amino)-5-((4-(3-fluoro-1H-indazol-1-yl)pyrimidin-2-yl)amino)-4-methoxyphenyl)acrylamide (Compound 7);

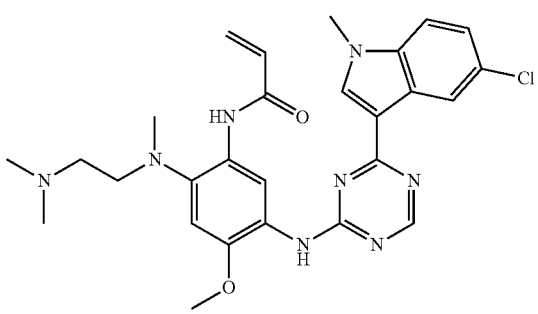 [SMILES: C=CC(=O)Nc1cc(Nc2ncnc(-c3cn(C)c4ccc(Cl)cc34)n2)c(OC)cc1N(C)CCN(C)C]

N-(5-((4-(6-chloro-5-methoxy-1-methyl-1H-indol-3-yl)-1,3,5-triazin-2-yl)amino)-2-((2-(dimethylamino)ethyl(methyl)amino)-4-methoxyphenyl)acrylamide (Compound 10);

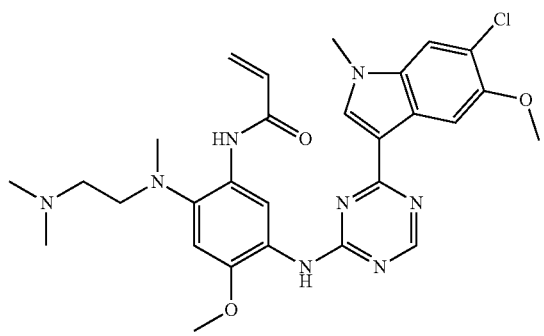

N-(2-((2-(dimethylamino)ethyl(methyl)amino)-5-((4-(5-fluoro-1-methyl-1H-indol-3-yl)-1,3,5-triazin-2-yl)amino)-4-methoxyphenyl)acrylamide (Compound 11);

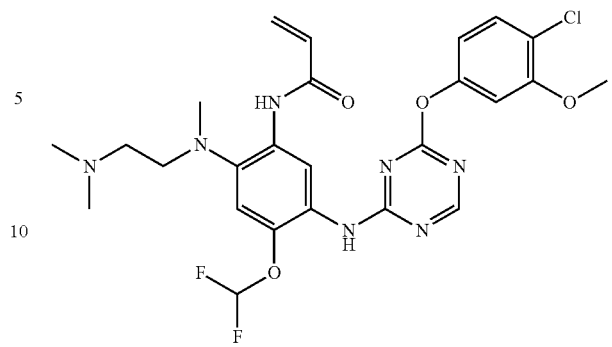

N-(4-(difluoromethoxy)-2-((2-(dimethylamino)ethyl)(methyl)amino)-5-((4-(5-fluoro-1-methyl-1H-indol-3-yl)-1,3,5-triazin-2-yl)amino)phenyl)acrylamide (Compound 14);

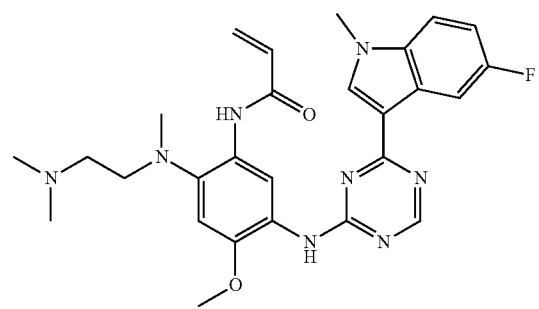 [SMILES: C=CC(=O)Nc1cc(Nc2ncnc(-c3cn(C)c4ccc(F)cc34)n2)c(OC)cc1N(C)CCN(C)C]

N-(5-((4-(4-chloro-3-methoxyphenoxy)-1,3,5-triazin-2-yl)amino)-2-((2-(dimethylamino)ethyl(methyl)amino)-4-methoxyphenyl)acrylamide (Compound 12);

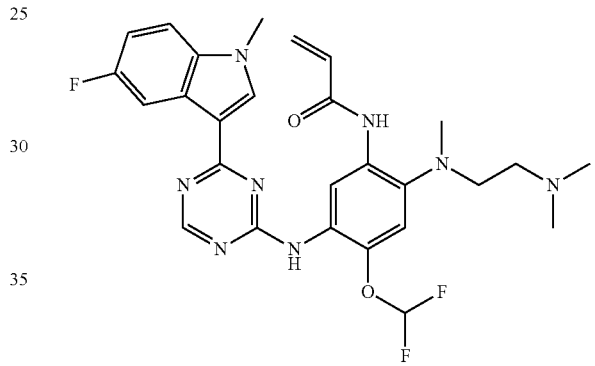

N-(2-((2-(dimethylamino)ethyl)(methyl)amino)-5-((4-(5-fluoro-1-methyl-1H-indol-3-yl)-1,3,5-triazin-2-yl)amino)-4-(2,2,2-trifluoroethoxy)phenyl)acrylamide (Compound 15);

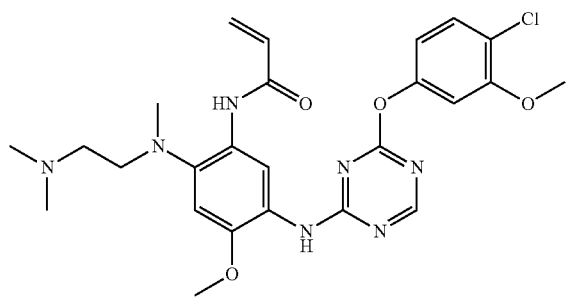

N-(5-((4-(4-chloro-3-methoxyphenoxy)-1,3,5-triazin-2-yl)amino)-4-(difluoromethoxy)-2-((2-(dimethylamino)ethyl(methyl)amino)phenyl)acrylamide (Compound 13);

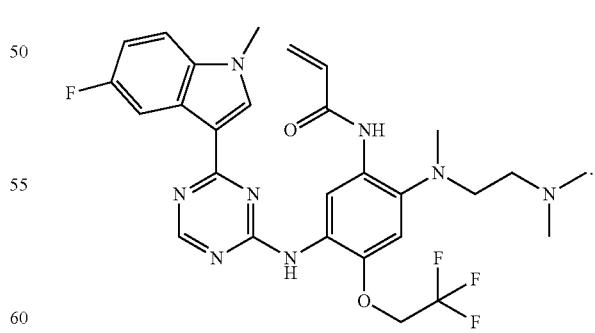

In another aspect, the present invention provides a compound of formula (II) or a pharmaceutically acceptable salt thereof:

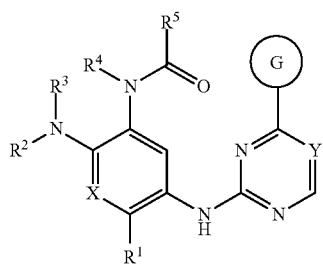

(II)

wherein

Y is selected from C, N, C—CF3, and C—Cl;

X is selected from C and N;

G is selected from aryl, heteroaryl or heterocyclyl, preferably C6-10 aryl, C5-10 heteroaryl or C4-10 heterocyclyl, the aryl, heteroaryl or heterocyclyl is optionally substituted by one or more substituents independently selected from C1-6 alkyl, C1-6 alkoxy, oxo, halogen, C6-C10 aryl, C5-10 heteroaryl or C4-10 heterocyclyl, C1-6 haloalkyl or C1-C6 aminealkyl;

$R^1$ is selected from hydrogen, C1-6 alkyl, C1-6 alkoxy, halogen, C1-6 haloalkyl or C1-6 haloalkoxy;

$R^2$ is selected from C1-6 alkyl, C1-6 heteroalkyl, C6-10 aryl, C5-10 heteroaryl, C4-10 heterocyclyl, C6-10 aryl-C1-6 alkylene, C5-10 heteroaryl-C1-6 alkylene, or C4-10 heterocyclyl-C1-6 alkylene, wherein the alkyl, aryl, heteroaryl or heterocyclyl is optionally substituted by one or more substituents independently selected from C1-6 alkyl, C1-6 alkoxy, C1-6 alkylamino, di-C1-6 alkylamino, oxo, halogen, C1-6 haloalkyl, aminoacyl, C1-6 alkylaminoacyl or di-C1-6 alkylaminoacyl;

$R^3$ is selected from hydrogen or $C_{1-6}$ alkyl;

alternatively, $R^2$ and $R^3$ together with the nitrogen atom to which they are attached form a heteroaryl or heterocyclyl, preferably a C3-10 heterocyclyl, wherein the heteroaryl or heterocyclyl is optionally substituted by one or more substituents independently selected from C1-6 alkyl, C1-6 alkoxy, C1-6 alkylamino, di-C1-6 alkylamino, oxo, halogen, C1-6 haloalkyl, aminoacyl, C1-6 alkylaminoacyl or di-C1-6 alkylaminoacyl;

$R^4$ is selected from hydrogen or $C_{1-6}$ alkyl;

$R^5$ is selected from the following groups:

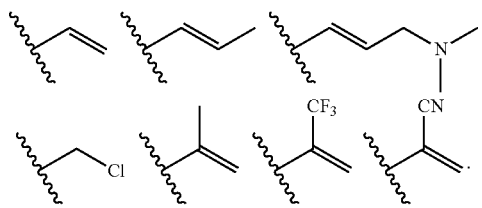

In a preferred embodiment, $R^2$ and $R^3$ together with the nitrogen atom to which they are attached form a group selected from: (3R)-3-(dimethylamino)pyrrolidin-1-yl, (3S)-3-(dimethylamino)pyrrolidin-1-yl, 3-(dimethylamino) azetidine-1-yl, [2-(dimethylamino)ethyl]-(methyl)amino, [2-(methylamino)ethyl](methyl)amino, 5-methyl-2,5-diazaspiro[3.4]octan-2-yl, (3aR,6aR)-5-methylhexahydro-pyrrolo[3,4-b]pyrrole-1(2H)-yl, 1-methyl-1,2,3,6-tetrahydropyridin-4-yl, 4-methylpiperazin-1-yl, 4-acetyl-piperazin-1-yl, morpholin-1-yl, 4-[2-(dimethylamino)-2-oxoethyl] piperazin-1-yl, methyl[2-(4-methylpiperazin-1-yl)ethyl] amino, methyl[2-(morpholine-4-yl)ethyl]amino, 1-amino-1,2,3,6-tetrahydropyridin-4-yl, or 4-[(2S)-2-aminopropionyl] piperazin-1-yl. G is selected from 4,5,6,7-tetrahydropyrazolo[1,5-a]pyridin-3-yl, 3,3-dimethyl-2,3-dihydro-1H-pyrrolo[3,2-b]pyridin-1-yl, 1H-pyrrolo[3,2-b] pyridin-1-yl, 1H-indol-3-yl, 3-methyl-1H-indol-1-yl, 1H-benzo[d]imidazol-1-yl, 1H-indazol-1-yl, 1H-pyrrolo[3,2-c]pyridin-1-yl, 3-methyl-1H-indazole-1-yl, 5-fluoro-3-methyl-1H-indazol-1-yl, 3-methyl-1H-pyrrolo[3,2-c]pyridin-1-yl, 1H-pyrrolo[3,2-c]pyridin-1-yl, 1H-benzo[d][1,2,3] triazol-1-yl, 6-fluoro-3-methyl-1H-indazol-1-yl, 8-methyl-imidazo[1,2-a]pyridin-3-yl, 8-fluoro-imidazo[1,2-a]pyridin-3-yl, 8-trifluoromethyl-imidazo[1,2-a]pyridin-3-yl, 1H-pyrrolo[3,2-c]pyridin-1-yl, 3-fluoro-TH-indazol-1-yl, 1-cyclopropyl-1H-indol-3-yl, 1-methyl-TH-indol-3-yl and pyrazolo[1,5-a]pyridin-3-yl, 8-trifluoromethylimidazo[1,2-a]pyridin-3-yl, 8-iodoimidazo[1,2-a]pyridin-3-yl, 5-fluoro-1-methyl-1H-indol-3-yl, 4-((dimethylamine)methyl)-3-phenyl-1H-pyrazole-1-yl, 5-chloro-1-methyl-1H-indol-3-yl, 5-methoxy-1-methyl-TH-indol-3-yl, 6-chloro-5-methoxy-1-methyl-1H-indol-3-yl, 4-chloro-3-methoxyphenoxy;

In a more preferred embodiment, the present invention provides a compound of formula (II) or a pharmaceutically acceptable salt thereof:

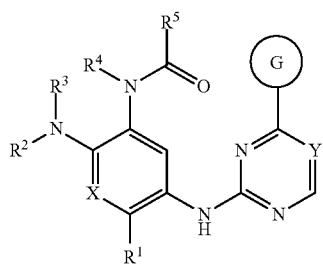

(II)

wherein

Y is selected from C, N, C—CF$_3$, and C—Cl;

X is selected from C and N;

G is selected from 1-methyl-1H-indol-3-yl, 1-cyclopropyl-1H-indol-3-yl, 3,3-dimethyl-2,3-dihydro-TH-pyrrole[3,2-b]pyridin-1-yl, 3-methyl-TH-pyrrolo[3,2-c] pyridin-1-yl, 4-(1H-pyrrole[3,2-c]pyridine-1-yl, 8-methylimidazo[1,2-a]pyridin-3-yl, 8-iodoimidazo[1,2-a]pyridin-3-yl, 8-trifluoromethylimidazo[1,2-a]pyridin-3-yl, 5-fluoro-1-methyl-1H-indol-3-yl, 4-((dimethylamine)methyl)-3-phenyl-1H-pyrazol-1-yl, 5-chloro-1-methyl-TH-indol-3-yl, 5-methoxy-1-methyl-1H-indol-3-yl, 6-chloro-5-methoxy-1-methyl-TH-indol-3-yl, 4-(4-chloro-3-methoxyphenoxy).

$R^1$ is selected from methoxy, ethoxy, difluoromethoxy and 2,2,2-trifluoroethoxy;

$R^4$ is hydrogen;

$R^5$ is the following group:

$R^2$ and $R^3$ together with the nitrogen atom to which they are attached form a group selected from: 3-(dimethylamino)azetidine-1-yl, [2-(dimethylamino)ethyl]-(methyl)amino, [2-(methylamino)ethyl](methyl)amino, 4-acetyl-piperazin-1-yl, morpholin-1-yl, 4-methylpiperazin-1-yl, 4-[2-(dimethylamino)-2-oxoethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl, or 4-[(2S)-2-aminopropionyl]piperazin-1-yl.

The compound of formula (II) according to the first aspect of the present invention, for its chemical synthesis and preparation, reference can be made to the article published in Journal of Medicinal Chemistry, 2015, 58, 8200-8215 by Zeng, Q B, et al., and patents WO2018/210246(A1), CN105461695A, CN201410365911A, CN201610126987A, CN109761960 and CN106928200A, and the compound is selected from the following compounds:

N-(2-((2-(dimethylamino)ethyl(methyl)amino)-4-methoxy-5-((4-(1-methyl-H-indol-3-yl)-1,3,5-triazin-2-yl)amino)phenyl)acrylamide (Compound 16);

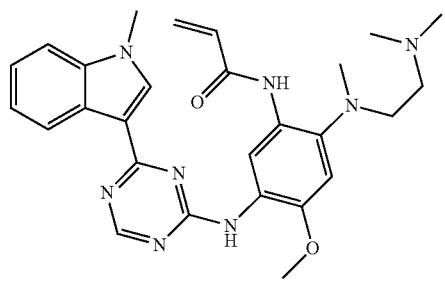 [SMILES: C=CC(=O)Nc1cc(Nc2ncnc(-c3cn(C)c4ccccc34)n2)c(OC)cc1N(C)CCN(C)C]

N-(5-((4-(3,3-dimethyl-2,3-dihydro-1H-pyrrolo[3,2-b]pyridin-1-yl)-1,3,5-triazin-2-yl)amino)-2-((2-(dimethylamino)ethyl)(methyl)amino)-4-methoxyphenyl)acrylamide (Compound 17);

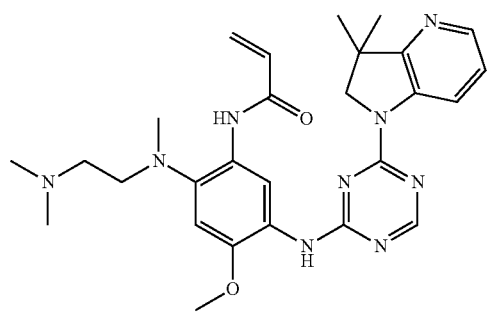 [SMILES: C=CC(=O)Nc1cc(Nc2ncnc(N3CC(C)(C)c4ncccc43)n2)c(OC)cc1N(C)CCN(C)C]

N-(2-((2-(dimethylamino)ethyl)(methyl)amino)-4-methoxy-5-((4-(3-methyl-1H-pyrrolo[3,2-c]pyridin-1-yl)-1,3,5-triazin-2-yl)amino)phenyl)acrylamide (Compound 18);

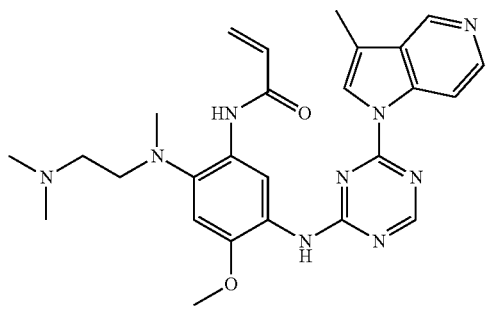 [SMILES: C=CC(=O)Nc1cc(Nc2ncnc(-n3cc(C)c4cnccc43)n2)c(OC)cc1N(C)CCN(C)C]

N-(2-((2-(dimethylamino)ethyl)(methyl)amino)-4-methoxy-5-((4-(8-methylimidazole[1,2-a]pyridin-3-yl)-1,3,5-triazin-2-yl)amino)phenyl)acrylamide (Compound 19);

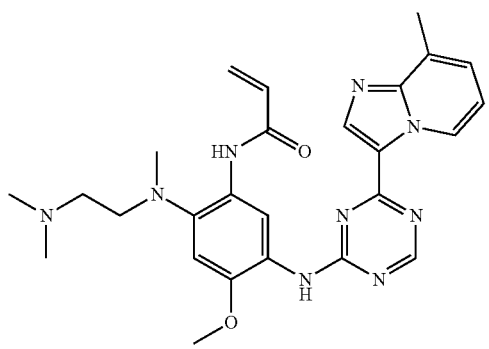 [SMILES: C=CC(=O)Nc1cc(Nc2ncnc(-c3cnc4c(C)cccn34)n2)c(OC)cc1N(C)CCN(C)C]

N-(4-(difluoromethoxy)-5-((4-(5-fluoro-1-methyl-1H-indol-3-yl)pyrimidin-2-yl)amino)-2-(methyl(2-(methylamino)ethyl)amino)phenyl)acrylamide (Compound 20);

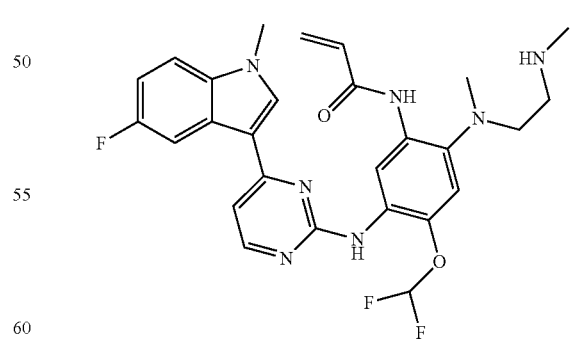

N-(2-((2-(dimethylamino)ethyl)(methyl)amino)-5-((4-(5-fluoro-1-methyl-1H-indol-3-yl)pyrimidin-2-yl)amino)-4-methoxyphenyl)acrylamide (Compound 21);

23

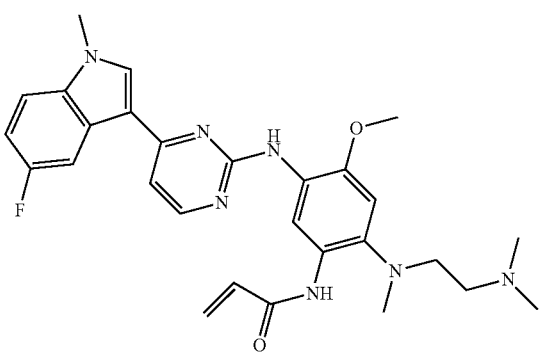 [SMILES: C=CC(=O)Nc1cc(Nc2nccc(-c3cn(C)c4ccc(F)cc34)n2)c(OC)cc1N(C)CCN(C)C]

N-(2-((2-(dimethylamino)ethyl)(methyl)amino)-4-ethoxy-5-((4-(5-fluoro-1-methyl-1H-indol-3-yl)pyrimidin-2-yl)amino)phenyl)acrylamide (Compound 22);

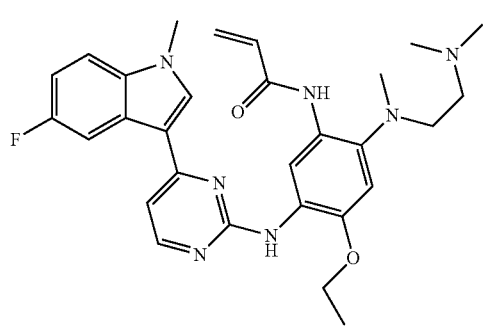 [SMILES: C=CC(=O)Nc1cc(Nc2nccc(-c3cn(C)c4ccc(F)cc34)n2)c(OCC)cc1N(C)CCN(C)C]

N-(2-((2-(dimethylamino)ethyl)(methyl)amino)-4-ethoxy-5-((4-(1-methyl-1H-indol-3-yl)pyrimidin-2-yl)amino)phenyl)acrylamide (Compound 23);

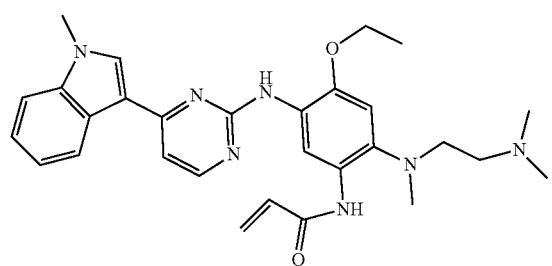 [SMILES: C=CC(=O)Nc1cc(Nc2nccc(-c3cn(C)c4ccccc34)n2)c(OCC)cc1N(C)CCN(C)C]

N-(4-ethoxy-2-(methyl(2-(methylamino)ethyl)amino)-5-((4-(1-methyl-1H-indol-3-yl)pyrimidine-2-yl)amino)phenyl)acrylamide (Compound 24);

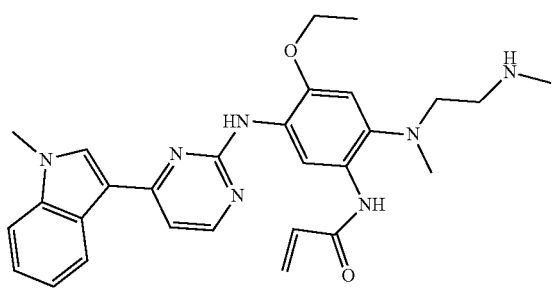 [SMILES: C=CC(=O)Nc1cc(Nc2nccc(-c3cn(C)c4ccccc34)n2)c(OCC)cc1N(C)CCNC]

24

N-(5-((4-(5-fluoro-1-methyl-1H-indol-3-yl)pyrimidin-2-yl)amino)-4-methoxy-2-(methyl(2-(methylamino)ethyl)amino)phenyl)acrylamide (Compound 25);

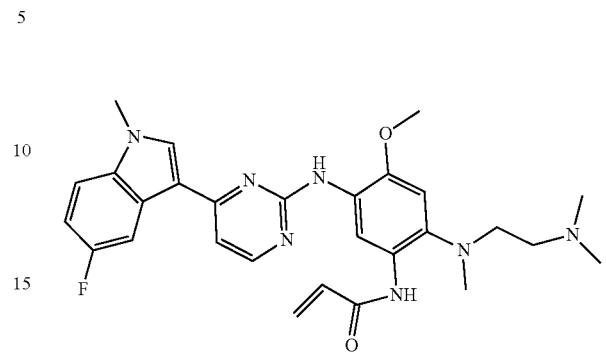

N-(4-(difluoromethoxy)-2-(methyl(2-(methylamino)ethyl)amino)-5-((4-(1-methyl-1H-indole-3-yl)pyrimidin-2-yl)amino)phenyl)acrylamide (Compound 26);

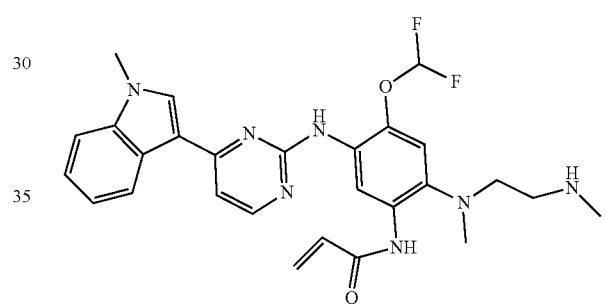

N-(4-ethoxy-5-((4-(5-fluoro-1-methyl-1H-indol-3-yl)pyrimidin-2-yl)amino)-2-(methyl(2-(methylamino)ethyl)amino)phenyl)acrylamide (Compound 27);

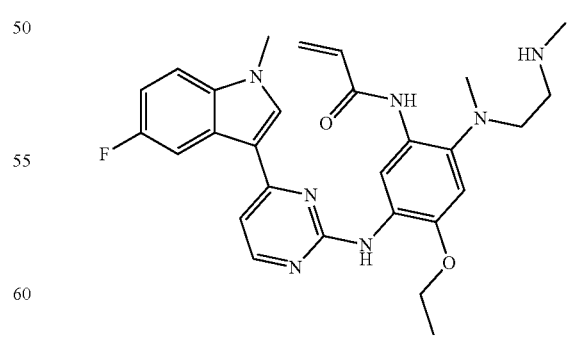

N-(5-((4-(1-cyclopropyl-1H-indole)pyrimidin-2-yl)-2-((2-(dimethylamine)ethyl(methyl)amine)-4-methoxyphenyl)acrylamide hydrochloride (Compound 28);

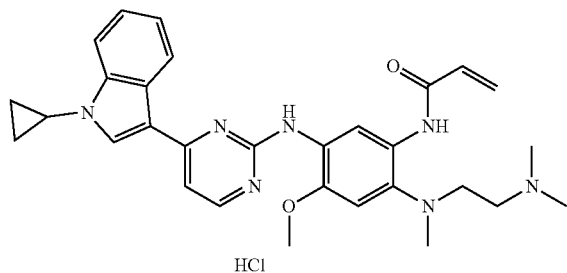 [SMILES: C=CC(=O)Nc1cc(Nc2nccc(-c3cn(C4CC4)c4ccccc34)n2)c(OC)cc1N(C)CCN(C)C ; Cl]

N-(5-((4-(1-cyclopropyl-1H-indole)pyrimidin-2-yl)-2-((2-(dimethylamine)ethyl(methyl)amine)-4-methoxyphenyl) acrylamide methanesulfonate (Compound 29);

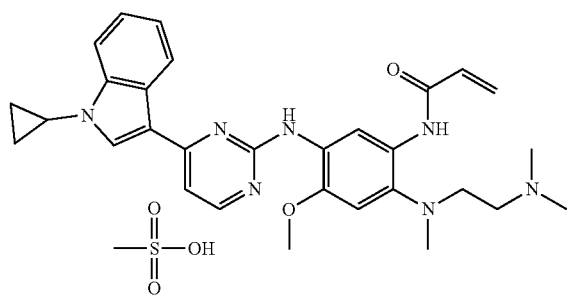

N-(5-((4-(1-cyclopropyl-1H-indole)pyrimidin-2-yl)-2-((2-(dimethylamine)ethyl(methyl)amine)-4-methoxyphenyl) acrylamide (Compound 30);

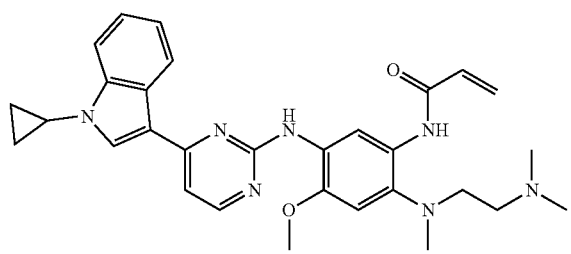 [SMILES: C=CC(=O)Nc1cc(Nc2nccc(-c3cn(C4CC4)c4ccccc34)n2)c(OC)cc1N(C)CCN(C)C]

N-(2-((2-(dimethylamine)ethyl(methyl)amine)-5-((4-(1-methyl-1H-indol-3-yl)pyrimidine-2-yl)amine)-6-(2,2,2-trifluoroethoxy)pyridin-3-yl)acrylamide methanesulfonate (Compound 31);

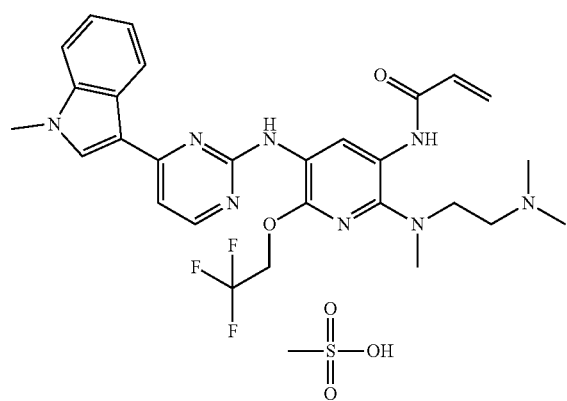

N-(2-((2-(dimethylamine)ethyl(methyl)amine)-5-((4-(1-methyl-1H-indol-3-yl)pyrimidine-2-yl)amine)-6-(2,2,2-trifluoroethoxy)pyridin-3-yl)acrylamide hydrochloride (Compound 32);

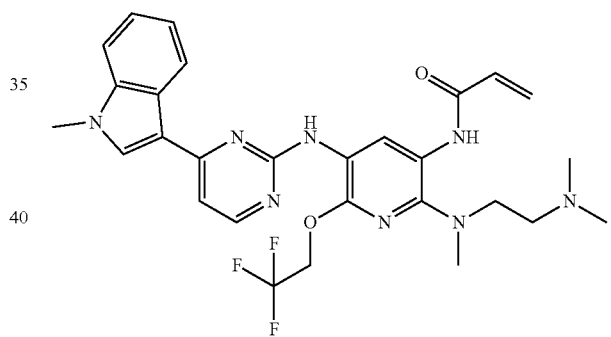

N-(2-((2-(dimethylamine)ethyl(methyl)amine)-5-((4-(1-methyl-1H-indol-3-yl)pyrimidine-2-yl)amine)-6-(2,2,2-trifluoroethoxy)pyridin-3-yl)acrylamide (Compound 33)

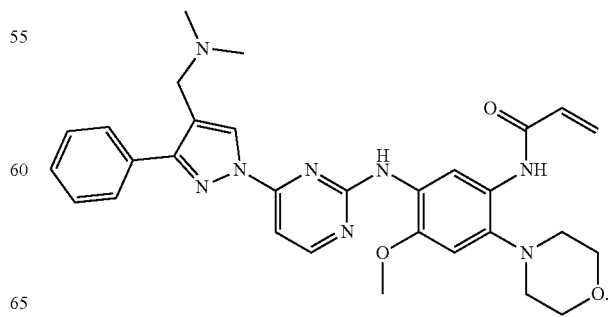

N-(5-((4-(4-((dimethylamine)methyl)-3-phenyl-1H-pyrazol-1-yl)pyrimidin-2-yl)amine)-4-methoxy-2-morpholinylphenyl) acrylamide (Compound 34);

In another aspect, the present invention provides a compound of formula (III) or a pharmaceutically acceptable salt thereof:

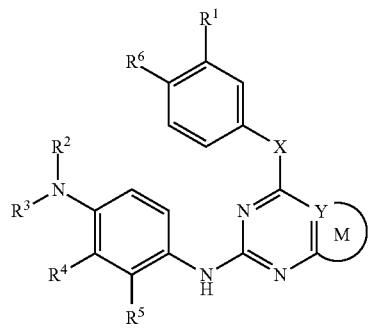

(III)

Y is selected from C;
X is selected from CH$_2$, NH, and O; M and pyrimidine ring (Y=C) form a fused heteroaryl or heterocyclyl, M is selected from a heteroaryl or heterocyclyl fused to a pyrimidine ring, preferably C5-C10 heteroaryl including pyrimidine ring, C4-C10 heterocyclyl, the heteroaryl or heterocyclyl is optionally substituted by one or more substituents independently selected from C1-6 alkyl, C1-6 alkoxy, oxo, halogen or C1-6 halogenated alkyl;
alternatively, when M does not form a fused heteroaryl or heterocyclyl with a pyrimidine ring (Y=C), then Y is selected from C—Cl and C—CF$_3$;
R$^1$ is selected from the following groups:

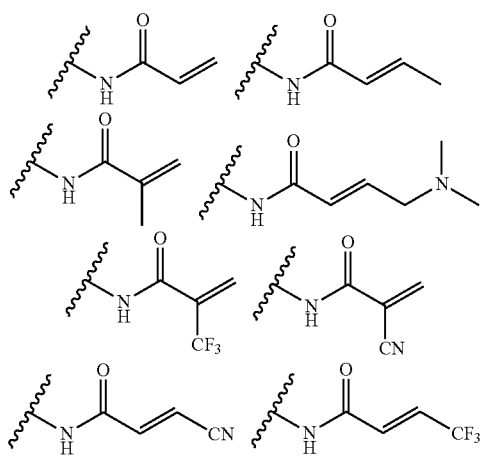

R$^3$ is selected from hydrogen or C$_{1-6}$ alkyl;
Alternatively, R$^2$ and R$^3$ together with the nitrogen atom to which they are attached form a heteroaryl or heterocyclyl, preferably a C3-10 heterocyclyl, wherein the heteroaryl or heterocyclyl is optionally substituted by one or more substituents independently selected from C1-6 alkyl, C1-6 alkoxy, C1-6 alkylamino, di-C1-6 alkylamino, oxo, halogen, C1-6 haloalkyl, aminoacyl, C1-6 alkylaminoacyl or di-C1-6 alkylaminoacyl;
R$^4$, R$^5$ and R$^6$ are selected from hydrogen, nitro, cyano, hydroxy, halogen, C1-6 alkyl, C1-6 alkoxy, C1-6 haloalkyl or C1-6 haloalkoxy, alkylacyl, C1-6 alkylacyl, alkoxyacyl, C1-C6 alkoxyacyl, aminoacyl or C1-6 alkylaminoacyl;

In a preferred embodiment, when Y is selected from C, the fused heteroaromatic ring composed of M and pyrimidine ring is selected from 7H-pyrazolo[2,3-d]pyrimidinyl, thieno[3,2-d]pyrimidinyl;
X is selected from O;
R1 is selected from the following group:

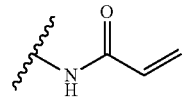

R$^2$ and R$^3$ together with the nitrogen atom to which they are attached to form a heteroaryl or heterocyclyl, 4-methylpiperazin-1-yl, 4-acetyl-piperazin-1-yl;
R$^4$, R$^5$ and R$^6$ are selected from hydrogen, fluorine, chlorine, methoxy; In another preferred embodiment, Y is selected from C—CF$_3$, M does not form a fused heteroaryl ring with a pyrimidine ring;
X is selected from NH, O;
R1 is selected from the following group:

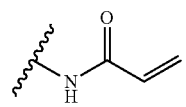

R$^2$ and R$^3$ together with the nitrogen atom to which they are attached to form a heteroaryl or heterocyclyl, 4-methylpiperazin-1-yl, 4-acetyl-piperazin-1-yl;
R$^4$ and R$^5$ are selected from hydrogen, fluorine, chlorine, methoxy.

The compound of formula (III) according to the second aspect of the present invention, for its chemical synthesis and preparation, reference can be made to the article published in Journal of Medicinal Chemistry, 2018, 61, 4290-4300 by Chen, L F, et al. and its references, which is selected from the following compounds:
N-(3-((2-((3-fluoro-4-(4-methylpiperazin-1-yl)phenyl)amine)-7H-pyrazole[2,3-d]pyrimidine-4-yl) oxo)phenyl) acrylamide (Compound 35);

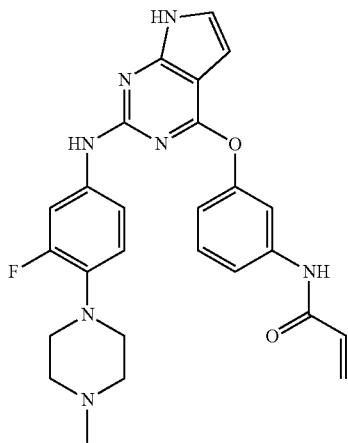 [SMILES: C=CC(=O)Nc1cccc(Oc2nc(Nc3ccc(N4CCN(C)CC4)c(F)c3)nc3[nH]ccc23)c1]

N-(3-((2-((4-(4-methylpiperazin-1-yl)phenyl)amine)thieno[3,2-d]pyrimidin-4-yl)oxo)phenyl)acrylamide (Compound 36);

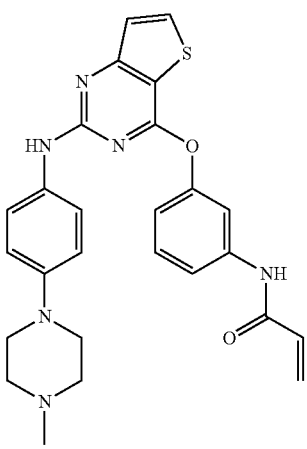 [SMILES: C=CC(=O)Nc1cccc(Oc2nc(Nc3ccc(N4CCN(C)CC4)cc3)nc3ccsc23)c1]

N-(3-((2-((4-(4-acetylpiperazin-1-yl)-2-methoxyphenyl)amine)-6-(trifluoromethoxy)pyrimidine-4-yl) amine)phenyl)acrylamide (Compound 37);

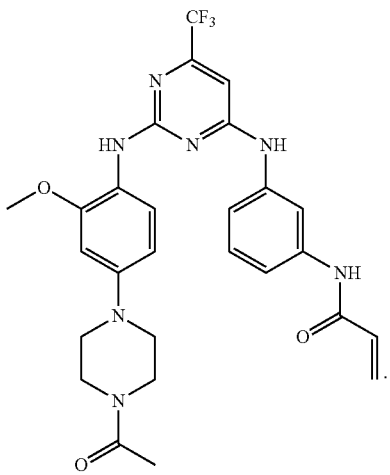 [SMILES: C=CC(=O)Nc1cccc(Nc2cc(C(F)(F)F)nc(Nc3ccc(N4CCN(C(C)=O)CC4)cc3OC)n2)c1]

In another aspect, the present invention provides a compound of formula (IV) or a pharmaceutically acceptable salt thereof.

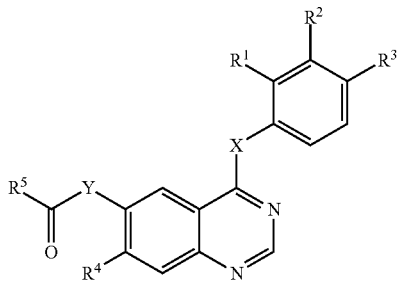

(IV)

X and Y are selected from O, NH;

R$^1$, R$^2$, R$^3$ and R$^4$ are selected from hydrogen, nitro, cyano, hydroxy, halogen, C1-6 alkyl, C1-6 alkoxy, C1-6 haloalkyl or C1-6 haloalkoxy, alkylacyl, C1-6 alkylacyl, alkoxyacyl, C1-C6 alkoxyacyl, aminoacyl or C1-6 alkylaminoacyl;

R$^5$ is selected from C3-10 heterocyclyl, wherein the heteroaryl or heterocyclyl is optionally substituted by one or more substituents independently selected from C1-6 alkyl, C1-6 alkoxy, C1-6 alkylamino, di-C1-6 alkylamino, oxo, halogen, C1-6 haloalkyl, aminoacyl, C1-6 alkylaminoacyl or di-C1-6 alkylaminoacyl;

In a preferred embodiment, X is selected from NH and Y is selected from O;

R$^1$, R$^2$, R$^3$ and R$^4$ are selected from hydrogen, halogen, C1-6 alkoxy;

R$^5$ is selected from 3-(dimethylamino)azetidine-1-yl, [2-(dimethylamino)ethyl]-(methyl)amino, [2-(methylamino)ethyl](methyl)amino, 4-acetyl-piperazin-1-yl, morpholin-1-yl, 4-methylpiperazin-1-yl, 4-[2-(dimethylamino)-2-oxoethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl, or 4-[(2S)-2-aminopropionyl]piperazin-1-yl, (2R)-2,4-dimethylpiperazin-1-yl; In another more preferred embodiment, X is selected from NH, and Y is selected from O;

R$^1$ is selected from F;
R$^2$ is selected from Cl;
R$^3$ is selected from H;
R$^4$ is selected from methoxy;
R$^5$ is selected from (2R)-2,4-dimethylpiperazin-1-yl;

The compound of formula (IV) according to another aspect of the present invention, for its chemical synthesis, reference can be made to the article published in Journal of Medicinal Chemistry, 2015, 58, 8200-8215 by Zeng, Q B, et al., which is selected from the following compounds: (R)-4-((3-chloro-2-fluorophenyl)amine)amine)-7-methoxyquinazolin-6-yl-2,4-dimethylpiperazinyl-1-carboxylic acid ester (Compound 38);

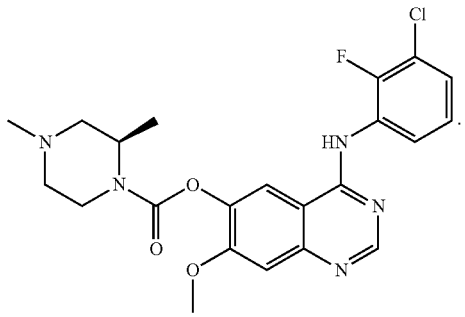 [SMILES: COc1cc2ncnc(Nc3cccc(Cl)c3F)c2cc1OC(=O)N1CCN(C)C[C@H]1C]

In another aspect, the present invention provides a compound of formula (V) or a pharmaceutically acceptable salt thereof:

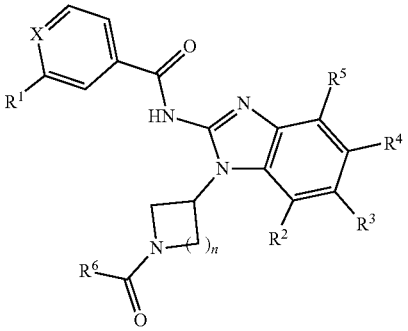

(V)

wherein

X is selected from C and N;

$R^1$, $R^2$, $R^3$, $R^4$ and $R^5$ are selected from hydrogen, nitro, cyano, hydroxy, halogen, C1-6 alkyl, C1-6 alkoxy, C1-6 haloalkyl or C1-6 haloalkoxy, alkylacyl, C1-6 alkylacyl, alkoxyacyl, C1-C6 alkoxyacyl, aminoacyl or C1-6 alkylaminoacyl;

n is selected from 1, 2, 3 and 4;

$R^6$ is selected from the following groups:

In a preferred embodiment, X is selected from N;

$R^1$ is selected from $C_{1-6}$ alkyl;

$R^2$, $R^3$, $R^4$ and $R^5$ are selected from hydrogen, halogen, C1-6 alkoxy;

In another more preferred embodiment, $R^1$ is selected from methoxy;

$R^2$ is selected from F or Cl;

$R^3$, $R^4$ and $R^5$ are selected from hydrogen;

n is selected from 4;

$R^6$ is selected from

The compound of formula (V) according to the present invention, for its chemical synthesis, reference can be made to the article published in Journal of Medicinal Chemistry, 2016, 59, 6671-6689 by Lelais, Q et al., which is selected from the following compounds:

(R,E)-N-(7-chloro-1-(1-(4-(dimethylamine)-2-butenoyl) azepane-3-yl)-1H-benzo[d]imidazol-2-yl)-2-methylisonicotinamide (Compound 39);

In another aspect, the present invention also provides a method for producing an anticancer effect in a warm-blooded animal such as a human in need of such treatment, which comprises: administering an effective amount of the compounds of formula (II), formula (III), formula (IV) and formula (V) or pharmaceutically acceptable salts thereof to the animal.

In another aspect, the present invention also provides use of the compounds of formula (II), formula (III), formula (IV) and formula (V) as described above or pharmaceutically acceptable salts thereof and additional antitumor substances for the simultaneous, independent or sequential treatment of cancer.

Those skilled in the art should understand that salts of compounds of formula (I), formula (II), formula (III), and formula (IV) and formula (V), including pharmaceutically acceptable salts, can be prepared. These salts can be prepared in situ during the final isolation and purification of the compound, or by separately reacting the purified compound in its free acid or free base form with a suitable base or acid, respectively.

It can form pharmaceutically acceptable acid addition salts with inorganic and organic acids, for example, acetate, aspartate, benzoate, benzenesulfonate, bromide/hydrobromide, bicarbonate/carbonate, bisulfate/sulfate, camphorsulfonate, chloride/hydrochloride, citrate, ethanedisulfonate, fumarate, glucoheptonate, gluconate, glucuronate, hippurate, hydroiodide/iodide, hydroxylethyl sulfonate, lactate, lactobionate, lauryl sulfate, malate, maleate, malonate, mandelate, mesylate, methyl sulfate, naphthoate, naphthalenesulfonate, nicotinate, nitrate, stearate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate.

Inorganic acids that can form salts include, for example, hydrochloric acid, hydrobromic acid, sulfuric acid, nitric acid, phosphoric acid, and the like.

Organic acids that can form salts include, for example, ethanoic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, etc. Pharmaceutically acceptable base addition salts can be formed with inorganic or organic bases.

Inorganic bases that can form salts include, for example, ammonium salts and metals of groups I to XII of the periodic table of elements. In certain embodiments, the salts are derived from sodium, potassium, ammonium, calcium, magnesium, iron, silver, zinc, and copper; particularly suitable salts include ammonium, potassium, sodium, calcium, and magnesium salts.

Organic bases that can form salts include, for example, primary amines, secondary amines, and tertiary amines. Substituted amines include naturally occurring substituted amines, cyclic amines, alkali ion exchange resins, and the like. Some organic amines include isopropylamine, diethanolamine, diethylamine, lysine, meglumine, piperazine, and tromethamine.

The pharmaceutically acceptable salts herein can be synthesized from basic or acidic moieties by conventional chemical methods. Generally, these salts can be prepared by reacting the free acid form of these compounds with a stoichiometric amount of a suitable base (hydroxide, carbonate, bicarbonate, etc. of Na, Ca, Mg, or K), or by reacting the free base form of these compounds with a stoichiometric amount of an appropriate acid. These reactions are usually carried out in water or in an organic solvent, or in a mixture of both. Generally, when appropriate, a non-aqueous medium such as diethyl ether, acetic ether, ethanol, isopropanol, or acetonitrile is used. A list of other suitable salts can be found in "Remington's Pharmaceutical Sciences", 20th edition, Mack Publishing Company, Easton, Pa., (1985); and "Handbook of Pharmaceutical Salts: Properties, Selection, and Use" by Stahl and Wermuth (Wiley-VCH, Weinheim, Germany, 2002).

Solvates of compounds of formula (I), formula (II), formula (III), and formula (IV) and formula (V), including pharmaceutically acceptable solvates, can also be prepared. "Solvate" refers to a complex of variable stoichiometry formed by a solute and a solvent. Such solvents for the purposes herein do not affect the biological activity of the solute. Examples of suitable solvents include, but are not limited to water, MeOH, EtOH, and AcOH. The solvate in which water is a solvent molecule usually refers to a hydrate. Hydrates include components that contain stoichiometric amounts of water, as well as components that contain variable amounts of water.

As used herein, the term "pharmaceutically acceptable" means a compound suitable for pharmaceutical use. Salts and solvates (e.g., hydrates and salt hydrates) of the compounds herein that are suitable for use in medicine are those in which the counter ion or binding solvent is pharmaceutically acceptable. However, salts and solvates with non-pharmaceutically acceptable counter ions or bound solvents are also included within the scope of the present application, for example, as intermediates for the preparation of other compounds herein and their pharmaceutically acceptable salts and solvates.

Compounds of formula (I), formula (II), formula (III), and formula (IV) and formula (V) (including salts and solvates thereof) may exist in crystalline form, non-crystalline form, or mixtures thereof. The compound or salt or solvate thereof may also exhibit polymorphism, i.e., the ability to appear in different crystalline forms. These different crystalline forms are generally known as "polymorphs". Polymorphs have the same chemical composition, but the packing, geometric arrangement, and other description characteristics of the crystalline solid state are different. Therefore, polymorphs can have different physical properties, such as shape, density, hardness, deformability, stability, and solubility properties. Polymorphs usually exhibit different melting points, IR spectra, and X-ray powder diffraction patterns, all of which can be used for identification. Those skilled in the art can understand, for example, by changing or adjusting the conditions used in the crystallization/recrystallization of the compounds of formula (I), formula (II), formula (III), and formula (IV) and formula (V), it may produce different polymorphs.

Different isomers of compounds of formula (I), formula (II), formula (III), and formula (IV) and formula (V) are also included herein. "Isomer" refers to compounds that have the same composition and molecular weight, but differ in physical and/or chemical properties. The difference in structure can be in the structure (geometric isomers) or in the ability to rotate plane polarized light (stereoisomers). Regarding stereoisomers, compounds of formula (I), formula (II), formula (III), and formula (IV) and formula (V) may have one or more asymmetric carbon atoms, and may appear as racemates, racemic mixtures and as individual enantiomers or diastereomers. All such isomeric forms are included within the scope of the present application, including mixtures thereof. If the compound contains a double bond, the substituent may be in E or Z configuration. If the compound contains a disubstituted cycloalkyl, the substituent of the cycloalkyl may have a cis- or trans-configuration. It is also desirable to include all tautomeric forms.

Any asymmetric atoms (such as carbon, etc.) of the compounds of formula (I), formula (II), formula (III), and formula (IV) and formula (V) can be present in racemic or enantiomerically enriched, for example (R)-, (S)-, or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess. If possible, the substituents on the atoms with unsaturated double bonds exist in the form of cis-(Z)- or trans-(E)-.

Thus, as used herein, compounds of formula (I), formula (II), formula (III), formula (IV) and formula (V) can be one of possible isomers, rotamers, atropisomers, tautomers or mixtures thereof, for example as substantially pure geometric isomers (cis or trans), diastereomers, optical isomers (enantiomers), racemates or mixtures thereof.

Any resulting mixture of isomers can be separated into pure or substantially pure geometric or optical isomers, diastereomers, racemates, for example by chromatography and/or stepwise crystallization, based on the physicochemical differences of the components.

Any resulting racemate of the final product or intermediate can be resolved into optically enantiomers by known methods (e.g., by the separation of its diastereomeric salts), which is obtained by using optically active acids or bases, and optically active acidic or basic compounds are released.

In particular, the basic moiety can therefore be used to resolve the compounds herein into their optical enantiomers, for example by stepwise crystallization of salts formed with optically active acids (e.g., tartaric acid, dibenzoyltartaric acid, diacetyltartaric acid, di-O,O'-p-toluoyltartaric acid, mandelic acid, malic acid or camphor-10-sulfonic acid). Racemic products can also be resolved by chiral chromatography, such as high-pressure liquid chromatography (HPLC) using chiral adsorbents.

Included herein are unlabeled forms and isotope-labeled forms of compounds of formula (I), formula (II), formula (III), formula (IV) and formula (V). Isotope-labeled compounds have the structure described by the chemical formula given herein, except that one or more atoms are replaced with atoms having a selected atomic weight or mass number. Examples of isotopes that can be incorporated into compounds herein include isotopes of hydrogen, carbon, nitrogen, oxygen, phosphorus, fluorine and chlorine, such as $^2$H, $^3$H, $^{11}$C, $^{13}$C, $^{14}$C, $^{15}$N, $^{18}$F, $^{31}$P, $^{32}$P, $^{35}$S, $^{36}$Cl, $^{125}$I Included herein are various isotope-labeled compounds as defined herein, such as those in which radioactive isotopes (e.g., $^3$H and $^{14}$C) or those in which non-radioactive isotopes (e.g., $^2$H and $^{13}$C) occur. These isotope-labeled compounds can be used in metabolic studies (e.g., using $^{14}$C), reaction kinetics studies (e.g., using $^2$H or $^3$H), detection or imaging techniques, such as positron emission tomography (PET) or single photon emission computed tomography (SPECT), including tissue distribution analysis of drug substrates, or for radiation therapy of patients. In particular, $^{18}$F or labeled compounds may be particularly needed for PET or SPECT studies. Isotope-labeled compounds of formula (I), formula (II), formula (III), formula (IV) and formula (V) can generally be prepared by conventional techniques known to those skilled in the art or by the preparation method similar to the method described in the attached examples and preparation examples, using a suitable isotope-labeled reagent instead of the unlabeled reagent used previously.

In addition, substitution with heavier isotopes, especially deuterium (i.e., $^2$H or D) may bring certain therapeutic advantages due to greater metabolic stability, such as increased half-life in the body or reduced dose requirements or therapeutic index improvement. It is understood that deuterium is considered herein as a substituent of compounds of formula (I), formula (II), formula (III), formula (IV) and formula (V). The concentration of this heavier isotope, especially deuterium, may be determined by the isotope enrichment factor. The term "isotope enrichment factor" as used herein refers to the ratio between the isotopic abundance and the natural abundance of a specific isotope. If the substituent in the compound herein is labeled as deuterium, then for each labeled deuterium atom, the compound has at least 3500 (52.5% deuterium incorporation at each labeled deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation) of the isotope enrichment factor.

The second aspect herein provides a method for preparing compounds of formula (I), formula (II), formula (III), formula (IV) and formula (V) or pharmaceutically acceptable salts thereof as described in the first aspect herein. An illustrative general synthetic method is listed below, and the specific compounds prepared herein are provided in the examples.

The compounds of formula (I), formula (II), formula (III), formula (IV) and formula (V) can be prepared by methods known in the field of organic synthesis. When referring to the methods of the examples described below, it should be understood that some substituents may be substituted with groups well known in the art to obtain similar derivatives without departing from the spirit of the present invention. If necessary, protecting groups are used for sensitive or reactive groups in accordance with general principles or chemical methods. The protecting group is operated according to standard methods of organic synthesis (T. W. Greene and P. G M. Wuts, "Protective Groups in Organic Synthesis", 3rd Edition, Wiley, New York 1999). These groups are removed at a convenient stage of compound synthesis using methods well known to those skilled in the art. The selection method, reaction conditions and treatment sequence should be consistent with the preparation of compounds of formula (I), formula (II), formula (III), formula (IV) and formula (V).

Those skilled in the art will be able to recognize whether there is a stereocenter in the compounds of formula (I), formula (II), formula (III), formula (IV) and formula (V). Therefore, possible stereoisomers are included herein, and both racemic compounds and individual enantiomers are included. When the desired compound is an individual enantiomer, it can be obtained by stereospecific synthesis or by resolution of the final product or any convenient intermediate. The resolution of the final product, intermediate or starting material can be achieved by any suitable method known in the art. See, for example, "Stereochemistry of Organic Compounds" by E. L. Eliel, S. H. Wilen and L. N. Mander (Wiley-interscience, 1994).

The compounds described herein can be prepared from commercially available starting materials or synthesized using known organic, inorganic, and/or enzymatic methods. For example, the compound of formula (I) herein can be prepared according to a method similar to the synthesis method described in PCT application PCT/GB2012/051783, using suitable compound raw materials.

(1) In the presence of Lewis acid or other catalysts, the intermediate (a3) is obtained by reacting the compound of formula (a1) with the compound of formula (a2):

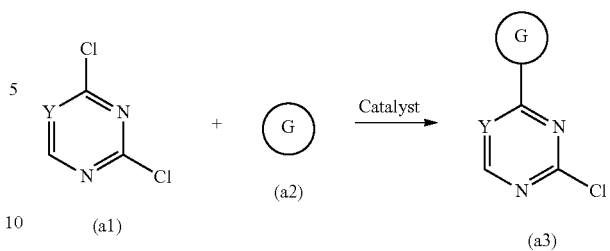

(2) In the presence of a suitable acid, intermediate (a3) is reacted with compound (a4) to obtain intermediate (a5), which is reacted with an amine under the action of a suitable base to obtain intermediate (a6):

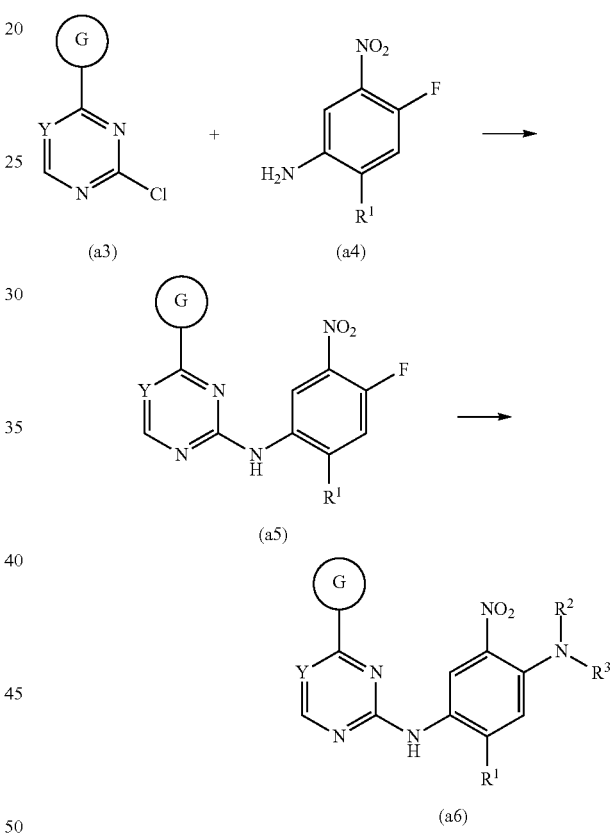

(3) The intermediate (a6) is reduced by a reducing agent to obtain the intermediate (a7):

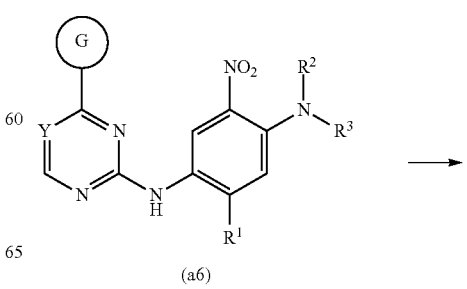

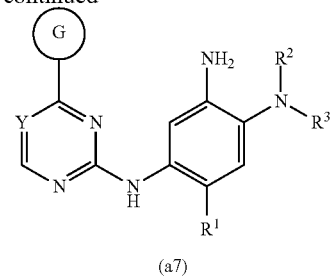

(a7)

(4) Intermediate (a7) is reacted with acryloyl chloride, acryloyl anhydride or acryloyl acid to obtain the compound of formula (I).

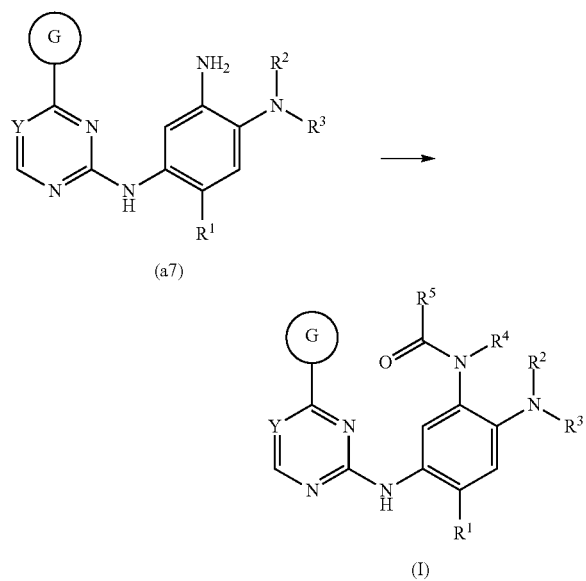

(5) The compound of formula I is reacted with the corresponding acid to obtain a pharmaceutically acceptable salt of the compound of formula I, or adjusted to the base of the corresponding formula I through alkali adjustment.

In step (1), the anhydrous solvent is selected from ethylene glycol dimethyl ether, dimethyl ether, xylene, etc.; the Lewis acid or catalyst is selected from $AlCl_3$, $FeCl_3$; the catalyst is selected from Pd/C, tetra(triphenylphosphine) palladium ($Pd(PPh_3)_4$), [1,1'-bis(diphenylphosphino)ferrocene]palladium dichloride ($Pd(dppf)Cl_2$); in step (2), the suitable acid is selected from p-toluenesulfonic acid, hydrochloric acid, hydrobromic acid, preferably p-toluenesulfonic acid; the suitable base is selected from an organic base or an inorganic base, preferably triethylamine, diisopropylethylamine, pyridine, sodium hydride, potassium carbonate and calcium hydride; the reducing agent is selected from $SnCl_2$ concentrated hydrochloric acid, Zn powder acetic acid, Fe powder acetic acid, Fe powder ammonium chloride, Pd/C catalytic hydrogenation; preferably Fe powder ammonium chloride, Pd/C catalytic hydrogenation. When necessary, in order to prevent undesired reactions of certain groups (such as amino, hydroxyl, etc.), the corresponding groups need to be protected, and at the same time, the protecting groups should be removed when appropriate.

The following further describes the present application through specific preparation examples. It is clear to those skilled in the art that in the following, unless otherwise specified, the materials and operating methods used are well known in the art. Unless otherwise stated, wherein: (i) the temperature is expressed in degrees Celsius (° C.) and the operation is carried out at room temperature, which generally refers to 15-35° C., preferably 20-30° C., more preferably 25-30° C.; (ii) the organic solvent is dried with anhydrous sodium sulfate, the solvent is removed by pressure distillation using rotary evaporator, and the bath temperature does not exceed 60° C.; (iii) the reaction process is followed by thin layer chromatography (TLC); (iv) the final product has a satisfactory hydrogen nuclear magnetic resonance spectroscopy ($^1$H-NMR), purity data (high performance liquid chromatography HPLC) and mass spectrometry (MS) data.

Pharmaceutical Composition

Provided herein is a pharmaceutical composition comprising a compound of formula (I), formula (II), formula (III), formula (IV) and formula (V) or pharmaceutically acceptable salts thereof as described above and a pharmaceutical acceptable diluent or carrier.

The pharmaceutical composition can be formulated for a specific route of administration, such as oral administration, parenteral administration, rectal administration, and the like. In addition, the pharmaceutical compositions herein can be produced in solid form (without limitation including capsules, tablets, pills, granules, powders or suppositories) or in liquid form (without limitation including solutions, suspensions or emulsions). The pharmaceutical composition can undergo conventional pharmaceutical operations (e.g., sterilization) and/or can contain conventional inert diluents, lubricants or buffers, and auxiliary materials such as preservatives, stabilizers, wetting agents, emulsifiers and buffers, etc.

Generally, the pharmaceutical composition is a tablet or gelatin capsule, which contains the active ingredient and
 a) diluents such as lactose, dextrose, sucrose, mannitol, sorbitol, cellulose and/or glycine;
 b) lubricants, such as silica, talc, stearic acid, magnesium or calcium salts thereof and/or polyethylene glycol; for tablets also contains
 c) binders, such as magnesium aluminum silicate, starch paste, gelatin, tragacanth, methyl cellulose, sodium carboxymethyl cellulose and/or polyvinylpyrrolidone; if necessary, also contains
 d) disintegrants, such as starch, agar, alginic acid or its sodium salt, or an effervescent mixture; and/or
 e) absorbents, colorants, flavoring agents and sweeteners.
According to methods known in the art, tablets may be film-coated or enteric-coated.

Suitable compositions for oral administration include an effective amount of a compound of formula (I) or a pharmaceutically acceptable salt thereof, which is in the form of a tablet, lozenge, water or oil suspension, dispersible powder or granules, emulsions, hard or soft capsules, or syrups or elixirs. A composition for oral use is prepared according to any method known in the art for preparing a pharmaceutical composition, and in order to provide a refined and palatable formulation, the composition can contain one or more agent selected from sweeteners, flavoring agents, colorants and preservatives. Tablets may contain the active ingredients in admixture with non-toxic pharmaceutically acceptable excipients which are suitable for the manufacture of tablets.

These excipients are, for example, inert diluents (such as calcium carbonate, sodium carbonate, lactose, calcium phosphate, or sodium phosphate); granulating agents and disintegrating agents (such as corn starch, or alginic acid); binders (such as starch, gelatin or gum arabic); and lubricants (such as magnesium stearate, stearic acid or talc). The tablets are uncoated or coated by known techniques to delay disintegration and absorption in the gastrointestinal tract, thereby providing a long-lasting effect over a longer period. For example, a time delay material can be used, such as glyceryl monostearate or glyceryl distearate. Formulations for oral administration can be delivered in hard gelatin capsules, wherein the active ingredient is mixed with an inert solid diluent (such as calcium carbonate, calcium phosphate, or kaolin), or delivered in soft gelatin capsules, wherein the active ingredient is mixed with water or oil medium (such as peanut oil, liquid paraffin or olive oil).

Certain injectable compositions are isotonic aqueous solutions or suspensions, and suppositories are advantageously prepared from fatty milk or suspensions. The composition may be sterilized and/or contain auxiliary materials, such as preservatives, stabilizers, wetting agents or emulsifier, dissolution promoters, salts for adjusting osmotic pressure, and/or buffers. In addition, it may also contain other therapeutically valuable substances. The compositions are prepared according to conventional mixing, granulating or coating methods, respectively, and contain about 0.1-75% or about 1-50% of the active ingredient.

Since water may promote the degradation of certain compounds, anhydrous pharmaceutical compositions and dosage forms are also provided herein, which contain the compounds herein as active ingredients.

The anhydrous pharmaceutical compositions and dosage forms herein can be prepared using anhydrous or low water content ingredients and low water content or low humidity conditions. Anhydrous pharmaceutical compositions can be prepared and stored in order to maintain their anhydrous nature. Therefore, the anhydrous composition is packaged using materials known to prevent contact with water so that it can be contained in a suitable formulation kit. Examples of suitable packaging include, without limitation, airtight foil, plastic, unit-dose containers (e.g., vials), blister packs, and tape packs.

Further provided herein are pharmaceutical compositions and dosage forms comprising one or more agents that reduce the rate of decomposition of the compounds herein as active ingredients. The agent (which is referred to herein as a "stabilizer") includes, without limitation, antioxidants (e.g., ascorbic acid), pH buffers, or salt buffers, and the like.

For individuals of about 50-70 kg, the pharmaceutical composition or combination product herein can be a unit dose of about 1-1000 mg of active ingredient, or about 1-500 mg or about 1-250 mg or about 1-150 mg or about 0.5-100 mg, or approximately 1-50 mg of active ingredient. The therapeutically effective dose of a compound, pharmaceutical composition, or combination product depends on the species, weight, age, and condition of the individual, the condition or disease being treated, or the severity thereof. A general practitioner, clinician, or veterinarian can easily determine the effective amount of each active ingredient required to prevent, treat, or inhibit the development of the condition or disease.

Therapeutic Use

In another aspect, provided herein are compounds of formula (I), formula (II), formula (III), formula (IV) and formula (V), or pharmaceutically acceptable salts thereof, for use as a medicament. In another aspect, provided herein is use of a compound of formula (I) or a pharmaceutically acceptable salt thereof in the preparation of a medicament for treating cancer.

In another aspect, provided herein is also a method for producing an anticancer effect in a warm-blooded animal, such as a human, in need of such treatment, which comprises: administering an effective amount of compounds of formula (I), formula (II), formula (III), formula (IV) and formula (V) or pharmaceutically acceptable salts thereof to the animal.

In another aspect, provided herein is use of compounds of formula (I), formula (II), formula (III), formula (IV) and formula (V) or pharmaceutically acceptable salts thereof and additional antitumor substances for the simultaneous, independent or sequential treatment of cancer.

In another aspect, provided herein is use of compounds of formula (I), formula (II), formula (III), formula (IV) and formula (V) or pharmaceutically acceptable salts thereof in the preparation of a medicament for treating cancer.

In another aspect, provided herein is use of compounds of formula (I), formula (II), formula (III), formula (IV) and formula (V) or pharmaceutically acceptable salts thereof in preparation of a medicament for inhibiting EGFR (also referred to as HER1) or HER2 or HER4 pathway.

In a preferred embodiment, provided herein is also a method for treating cancer, which comprises: administering compounds of formula (I), formula (II), formula (III), formula (IV) and formula (V) or pharmaceutically acceptable salts thereof to a subject in need thereof.

In a preferred embodiment, provided herein is also a method for inhibiting the EGFR (also referred to as HER1) or HER2 or HER4 pathway, which comprises: administering a compound of formula (I) or a pharmaceutically acceptable salts thereof to a subject in need thereof.

In the above embodiments, the subject may be a mammal or a human.

In another aspect, provided herein is also use of compounds of formula (II), formula (III), formula (IV) and formula (V) or pharmaceutically acceptable salts thereof as described above in the preparation of EGFR exon 20 mutations inhibitor and/or HER2 and HER4 kinase inhibitors.

In another aspect, provided herein is also a composition as described above for use in inhibiting the activity of EGFR kinase with EGFR exon 20 mutant, and/or the activity of HER2 kinase with exon mutant, and/or activity of HER4 kinase with exon 20 mutant.

The compounds of formula (I), formula (II), formula (III), formula (IV) and formula (V) or pharmaceutically acceptable salts thereof are as defined above.

In any aspect or embodiment mentioned above, the cancer may be selected from ovarian cancer, non-small cell lung cancer, cervical cancer, colorectal cancer, breast cancer, pancreatic cancer, glioma, glioblastoma, melanoma, prostate cancer, leukemia, lymphoma, non-Hodgkin lymphoma, gastric cancer, lung cancer, hepatocellular carcinoma, gastric cancer, gastrointestinal stromal tumor (GIST), thyroid cancer, cholangiocarcinoma, endometrial cancer, kidney cancer, anaplastic large cell lymphoma, acute myeloid leukemia (AML), multiple myeloma, melanoma, mesothelioma.

In a preferred embodiment, the cancer is non-small cell lung cancer.

The compound of formula (I), formula (II), formula (III), formula (IV) and formula (V) or pharmaceutically acceptable salts thereof can be used as a single therapeutic treatment, or in addition to the compounds of the present invention, it also involves routine surgery or radiation therapy or chemotherapy or immunotherapy. Such chemotherapy and the compounds of the present invention can be administered side-by-side, simultaneously, sequentially, or separately, and can contain one or more of the following types of anti-tumor agents:

(i) Antiproliferative/antitumor drugs and a combination thereof used in medical oncology, such as alkylating agents (e.g., cisplatin, oxaliplatin, carboplatin, cyclophosphamide, nitrogen mustard, melphalan, phenylbutyric acid nitrogen mustard, busulfan, temozolomide, nitrosoureas); antimetabolites (e.g., gemcitabine and antifolate, such as fluoropyrimidines (e.g., 5-fluorouracil and tegafur), raltitrexed, methotrexate, cytarabine, hydroxyurea); antitumor antibiotics (e.g., anthracyclines, such as adriamycin, bleomycin, doxorubicin, daunorubicin, epirubicin, idarubicin, mitomycin C, actinomycin, mithramycin); antimitotic agents (e.g., vinca alkaloids, such as vincristine, vinblastine, vindesine, vinorelbine; and taxanes, such as Paclitaxel, Taxotere); topoisomerase inhibitors (e.g., epipodophyllotoxin (such as etoposide, teniposide), anacridine, topotecan, camptothecin);

(ii) Cell growth inhibitors, such as anti-estrogen drugs (e.g., Tamoxifen, Fulvestrant, Toremifene, Raloxifene, Droloxifene, anti-androgens (e.g., Bicalutamide, Flutamide, Nilutamide, cyproterone acetate), LHRH antagonists or LHRH agonists (e.g., Goserelin, Leuprolide, and Buserelin), progestins (e.g., Megestrol acetate), aromatase inhibitors (e.g., Anastrozole, Letrozole, Exemestane), 5α-reductase inhibitors (e.g., finasteride);

(iii) Anti-invasive agents, such as c-Src kinase family inhibitors, such as Dasatinib and Bosutinib (SKI-606), and metalloproteinase inhibitors (such as marimastat), inhibitor of urokinase plasminogen activator receptor function or antibodies to heparinase;

(iv) Inhibitors of growth factor function: e.g., such inhibitors include growth factor antibodies and growth factor receptor antibodies (e.g., anti-erbB2 antibody Trastuzumab, anti-EGFR antibody Panitumumab, anti-erbB1 antibody Cetuximab and any growth factor or growth factor receptor antibody); such inhibitors also include: tyrosine kinase inhibitors, e.g., inhibitors of the epidermal growth factor family (e.g., EGFR family tyrosine kinase inhibitors, such as N-(3-chloro-4-fluorophenyl)-7-methoxy-6-(3-morpholinylpropoxy)-quinazolin-4-amine (Gefitinib, ZD1839), N-(3-ethynylphenyl)-6,7-bis(2-methoxyethoxy)quinazoline-4-amine (Erlotinib, OSI-774), 6-acrylamido-N-(3-chloro-4-fluorophenyl)-7-(3-morpholinylpropoxy)-quinazoline-4-amine (CI 1033), erbB2 tyrosine kinase inhibitor (e.g., Lapatinib); inhibitors of the hepatocyte growth factor family; inhibitors of the insulin growth factor family; inhibitors of the platelet-derived growth factor family, e.g., Imatinib and/or Nilotinib (AMN107); inhibitors of serine/threonine kinase (e.g., Ras/Raf signaling inhibitors, such as farnesyl transferase inhibitors, such as Sorafenib (BAY43-9006), Tipifarnib (R115777), Clonafenib (SCH66336)), through cell signaling inhibitors of mEK and/or AKT kinase, c-kit inhibitors, abl kinase inhibitors, PI3 kinase inhibitors, Plt3 kinase inhibitors, CSF-1R kinase inhibitors, IGF receptor (insulin-like growth factors) kinase inhibitors; aurora kinase inhibitors (e.g., AZD1152, PH739358, VX-680, MLN8054, R763, MP235, MP529, VX-528, AX39459), cyclin dependent kinase inhibitors, such as CDK2 and/or CDK4 inhibitor;

(v) Anti-angiogenic agents, such as agents that inhibit the action of vascular endothelial growth factor, such as anti-human vascular endothelial cell growth factor antibody Bevacizumab and, for example, VEGF receptor tyrosine kinase inhibitors, such as Vandetanib (ZD6474), Valtarani (PTK787), Sunitinib (SU11248), Axitinib (AG-013736), Pazopanib (GW786034), 4-(4-fluoro-2-methylindole-5-yloxy)-6-methoxy-7-(3-pyrrolidin-1-ylpropoxy)quinazoline (AZD2171; Example 240 in WO 00/47212), such as those disclosed in WO 97/22596, WO 97/30035, WO 97/32856 and WO 98/13354;

(vi) Vascular damaging agents, such as Complementin A4 and the compounds disclosed in WO 99/02166, WO 00/40529, WO00/41669, WO 01/92224, WO 02/04434 and WO 02/08213;

(vii) endothelin receptor antagonists, such as Zipotentan (ZD4054) or Atrasentan;

(viii) Gene therapy methods, including, for example, a method for replacing abnormal genes (such as abnormal p53 or abnormal BRCA1 or BRCA2); a GDEPT (gene-directed enzyme prodrug therapy) method, such as those using cytosine deaminase, thymidine kinase or bacteria nitroreductases; a method to increase patient tolerance to chemotherapy or radiation therapy, such as multidrug resistance gene therapy; and (ix) Immunotherapy methods, including, for example, in vitro and in vivo methods to increase the immunogenicity of the patient's tumor cells, such as transfection with cytokines (such as interleukin 2, interleukin 4, or granulocyte macrophage colony-stimulating factor); a method of reducing T cell inefficiency; a method of using transfected immune cells (such as cytokine-transfected dendritic cells); a method of using cytokine-transfected tumor cell lines; a method of using anti-idiotypic antibodies; a method of reducing function of immunosuppressive cells (e.g., regulatory T cells, myeloid-derived suppressor cells, or dendritic cells expressing IDO (indolamine 2,3-deoxygen enzymes)); and a method of using cancer vaccines composed of proteins or peptides derived from tumor-associated antigens (e.g., NY-ESO-1, mAGE-3, WT1 or Her2/neu).

Herein, if the term "combination therapy" is used to describe combined treatment, it should be understood that this may also mean simultaneous, independent, or sequential administration. The "combination administration" should be understood similarly. In one aspect of the present invention, "combination therapy" refers to simultaneous administration. In another aspect of the present invention, "combination therapy" refers to independent administration. In another aspect of the present invention, "combination therapy" refers to sequential administration. When administered sequentially or independently, the delay in the administration of the second component should not, for example, lose the benefit of the effects produced by using the combination.

EXAMPLE

The following further describes the present application in conjunction with the examples. It should be understood that the examples are only used to further illustrate and explain the present application, not to limit it.

Unless otherwise defined, technical and scientific terms in this specification have the same meaning as commonly understood by those skilled in the art. Although methods and materials similar or identical to those described herein can be used in experiments or practical applications, the materials and methods are described herein below. In case of conflict, the present specification, including definitions, will control. In addition, the materials, methods, and examples are for illustration only and are not limiting. The following further describes the present application in conjunction with specific examples, but it is not intended to limit the scope of the present application.

Example 1

Synthesis of (R)—N-(5-((4-(1H-pyrrole[3,2-c]pyridin-1-yl)-1,3,5-triazin-2-yl)amino)-2-(2-((dimethylamino)methyl)azetidine-1-yl)-4-methoxyphenyl)acrylamide (Compound 1)

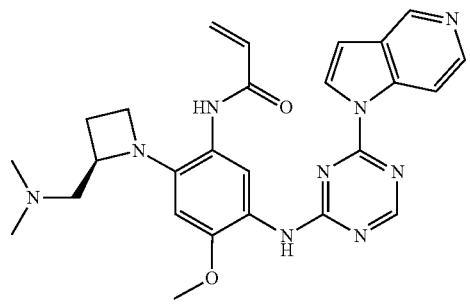 [SMILES: C=CC(=O)Nc1cc(Nc2ncnc(-n3ccc4cnccc43)n2)c(OC)cc1N1CC[C@@H]1CN(C)C]

Synthetic Route:

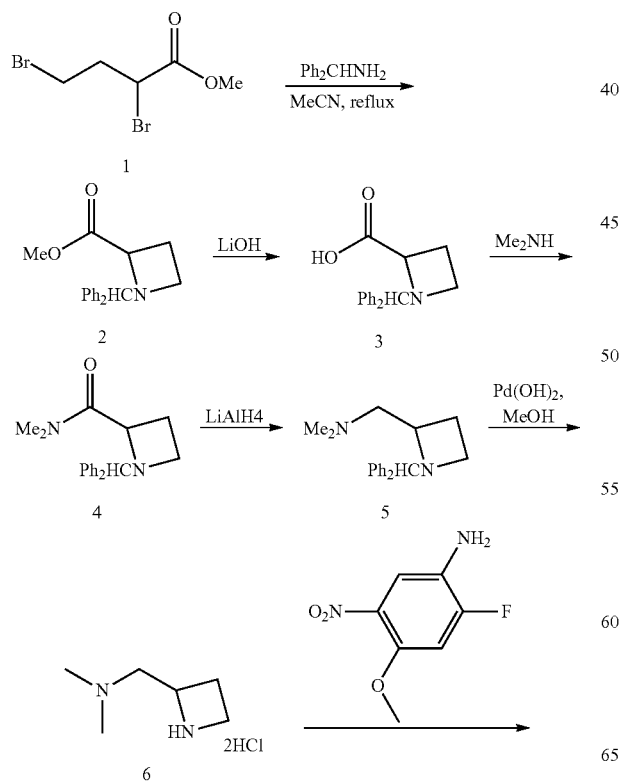

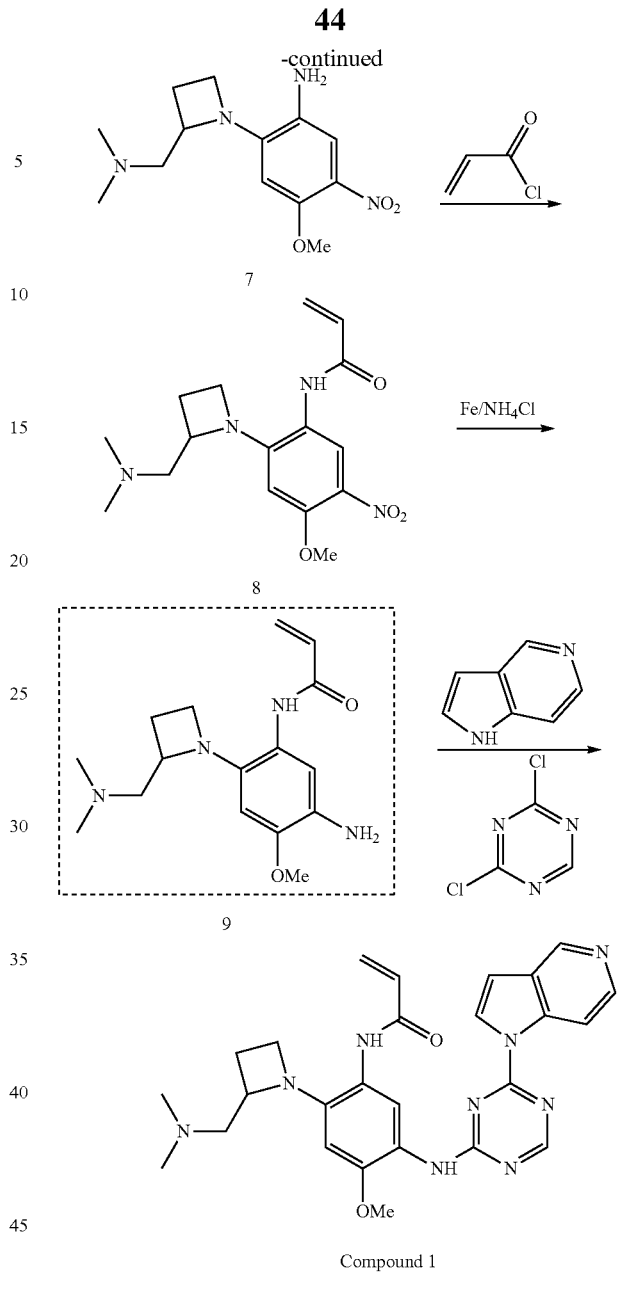

Compound 1 a. Synthesis of 1-diphenylmethylazetidine-2-carboxylic acid methyl ester (2)

To a solution of methyl 2,4-dibromobutyrate (40.0 g, 154 mmol) in acetonitrile (300 mL), benzylamine (49.9 g, 274 mmol) was slowly added dropwise at 20° C., and the reaction liquid was stirred at 20° C. for 2 hours. Triethylamine (23.4 g, 231 mmol) was added, and after the reaction solution was stirred at 55° C. for 48 hours, TLC (PE:EA=10:1) showed new spots, and the reaction mixture was concentrated to dryness by distillation under reduced pressure, water (1 L) and saturated sodium bicarbonate solution (500 mL) were added, and extraction was preformed with acetic ether (1 L×3). The organic phases were combined and dried over anhydrous sodium sulfate, filtered, concentrated and mixed with silica gel, and passed through the column (PE:EA=100:1 to 20:1) to obtain a colorless colloidal semi-solid methyl 1-dibenzylazetidine-2-carboxylate (16.0 g, yield: 35%).

$^1$H NMR: (CDCl$_3$, 400 MHz) δ7.49 (d, J=6.8 Hz, 2H), 7.41 (d, J=7.6 Hz, 2H), 7.34-7.20 (m, 6H), 4.49 (s, 1H), 3.76 (t, J=8.0 Hz, 1H), 3.44 (dt, J=4.2 Hz, 6.8 Hz, 1H), 3.40 (s, 3H), 2.99-2.90 (m, 1H), 2.39-2.33 (m, 1H), 2.24-2.18 (m, 1H).

b. Synthesis of 1-dibenzylazetidine-2-carboxylic acid (3)

To a mixed solution of methyl 1-diphenylmethylazetidine-2-carboxylate (44 g, 156 mmol) in THF (200 mL), MeOH (200 mL) and water (100 mL), LiOH·H$_2$O (32.8 g, 782 mmol) was added. After the reaction solution was stirred at 30° C. for 16 hours, TLC (PE:EA=10:1) showed that the reaction was complete. After concentrating under reduced pressure to remove THF and MeOH, water (500 mL) and dichloromethane (500 mL) were added, and after standing to obtain an aqueous phase, the pH was adjusted to about 5 with 2M dilute hydrochloric acid, and then extracted with acetic ether 500 mL×10). The organic phase was dried over anhydrous sodium sulfate, filtered, and concentrated to obtain the crude product of 1-dibenzylazetidine-2-carboxylic acid (40.0 g, yield: 86%). The crude product was used for the next reaction without purification.

$^1$H NMR: (CD$_3$OD, 400 MHz) δ7.58 (d, J=7.2 Hz, 2H), 7.54 (d, J=6.8 Hz, 2H), 7.46-7.36 (m, 6H), 5.63 (s, 1H), 4.58 (t, J=9.2 Hz, 1H), 4.03-3.96 (m, 1H), 3.94-3.86 (m, 1H), 2.76-2.70 (m, 1H), 2.46-2.40 (m, 1H).

c. Synthesis of 1-dibenzyl-N,N-dimethylazetidine-2-formamide (4)

To a solution of 1-dibenzylazetidine-2-carboxylic acid (30 g, 112 mmol) in DMF (300 mL), N-dimethylamine (27.5 g, 337 mmol) and HATU (64.0 g, 168 mmol) were added, and then triethylamine (56.8 g, 561 mmol) was added dropwise at 0° C. After the reaction solution was stirred at 20° C. for 16 hours, LCMS showed that the reaction was complete. After the reaction solution was quenched with water (1 L), acetic ether (1 L×3) was added, the layers were separated, the organic phase was dried over anhydrous sodium sulfate, concentrated and mixed with silica gel, and passed through the column (PE:EA=20:1 to 1:1) to obtain a white solid 1-benzyl-N,N-dimethylazetidine-2-formamide (25.0 g, yield: 68%).

$^1$H NMR: (CD$_3$OD, 400 MHz) δ7.51 (d, J=7.2 Hz, 2H), 7.41 (d, J=7.2 Hz, 2H), 7.28-7.16 (m, 6H), 4.58 (s, 1H), 4.25 (t, J=8.0 Hz, 1H), 3.38-3.34 (m, 1H), 2.98-2.95 (m, 1H), 2.63 (s, 3H), 2.53 (s, 3H), 2.36-2.20 (m, 1H), 2.18-2.10 (m, 1H).

d. Synthesis of 1-(1-dibenzylazetidine-2-yl)-N,N-dimethylmethylamine (5)

To a solution of 1-benzyl-N,N-dimethylazetidine-2-formamide in THF (200 mL), LiAlH4 (2.30 g, 60.6 mmol) was added in portions at 0° C., after the reaction solution was stirred at 0° C. for 0.5 hours, TLC (PE:EA=1:1) showed that the reaction was complete. The reaction solution was quenched with a mixed solution of water (2 mL) and 15% of aqueous sodium hydroxide solution (5 mL), and the filtrate obtained after filtration was concentrated to dryness to obtain a colorless oily liquid 1-(1-dibenzylazetidine-2-yl)-N,N-dimethylmethylamine (12.0 g, yield: 76%), which was used directly for the next reaction without further purification.

$^1$H NMR: (CD$_3$OD, 400 MHz) δ7.45-7.40 (m, 4H), 7.30-7.26 (m, 6H), 4.47 (s, 1H), 3.51-3.46 (m, 1H), 3.36-3.34 (m, 1H), 2.85-2.80 (m, 1H), 2.28-2.21 (m, 2H), 1.97 (s, 6H), 1.96-1.94 (m, 1H), 1.56 (dd, J=2.8 Hz, 12 Hz, 1H).

e. Synthesis of 1-(azetidine-2-yl)-N,N-dimethylmethylamine hydrochloride (6)

1-(1-Dibenzylazetidine-2-yl)-N,N-dimethylmethylamine (12.0 g, 42.8 mmol) and Pd(OH)$_2$ (3.0 g, 20% purity, 50% humidity) were dissolved in ethanol (250 mL), hydrogen gas (30 psi) was bubbled, and the reaction solution was stirred at 35° C. for 16 hours, TLC (DCM:MeOH=20:1) showed the reaction was complete. After filtration, HCl/MeOH (30 mL, 4M) was added to the filtrate, stirred at 20° C. for 0.5 hours, and then concentrated to dryness. PE/DCM (2/1, 30 mL) was added, stirred for 5 minutes, the excess liquid was poured out, and the remaining gum was dried under reduced pressure to obtain 1-(azetidin-2-yl)-N,N-dimethylmethylamine hydrochloride (7.0 g, yield: 70%, 2HCl), which was used directly for the next reaction without purification.

$^1$H NMR: (CD$_3$OD, 400 MHz) δ5.11-5.04 (m, 1H), 4.18-4.14 (m, 1H), 4.06-3.98 (m, 2H), 3.65 (dd, J=4.0 Hz, 14.4 Hz, 1H), 3.00 (s, 3H), 2.98 (s, 3H), 2.74-2.70 (m, 1H), 2.62-2.54 (m, 1H).

f. Synthesis of 2-(2-((dimethylamino)methyl)azetidine-1-yl)-4-methoxy-5-nitroaniline (7)

To a solution of 1-(azetidin-2-yl)-N,N-dimethylmethylamine hydrochloride (6.5 g, 34.9 mmol, 2HCl) in DMF (200 mL), 2-fluoro-4-methoxy-5 nitroaniline (5.0 g, 26.8 mmol) and cesium carbonate (43.7 g, 134 mmol) were added at 25° C., the reaction solution was heated to 130° C. and stirred at this temperature for 16 hours, TLC (DCM:MeOH=20:1) showed the reaction was complete. After the temperature of the reaction solution was reduced to 20° C., the reaction solution was poured into water (200 mL) and extracted with acetic ether (200 mL×4). The organic phases were combined and washed with saturated brine, dried over anhydrous sodium sulfate, filtered, concentrated and mixed with silica gel, passed through the column (PE:EA=5:1 to 2:1, then DCM:MeOH=50:1 to 20:1) to obtain a brown-black solid 2-(2-((dimethylamino)methyl)azetidine-1-yl)-4-methoxy-5-nitroaniline (3.7 g, yield: 49%).

$^1$H NMR: (CD$_3$OD, 400 MHz) δ7.39 (s, 1H), 6.35 (s, 1H), 4.49-4.47 (m, 1H), 4.31-4.29 (m, 1H), 3.88 (s, 3H), 3.71-3.69 (m, 1H), 2.79-2.75 (dd, J$_1$=4.0 Hz, J$_2$=12.8 Hz, 1H), 2.58-2.54 (m, 1H), 2.53-2.46 (m, 1H), 2.31 (s, 6H), 2.19-2.15 (m, 1H).

g. Synthesis of N-(2-(2-((dimethylamino)methyl) azetidine-1-yl)-4-methoxy-5-nitrophenyl)acrylamide (8)

To a solution of 2-(2-((dimethylamino)methyl)azetidine-1-yl)-4-methoxy-5-nitroaniline (1.5 g, 5.4 mmol) in DCM (20 mL), TEA (1.62 g, 16.1 mmol) was added and acrylic acid chloride (969 mg, 10.7 mmol) was added dropwise at 0° C. After the reaction was stirred at 0° C. for 1 hour, the reaction solution was heated to 25° C. and stirred for 16 hours, LCMS showed the reaction was complete. After quenched with water (100 mL), the reaction solution was extracted with DCM (100 mL×3). The organic phases were combined and dried over anhydrous sodium sulfate, filtered, concentrated and mixed with silica gel, and passed through the column (DCM:MeOH=100:1 to 20:1) to obtain a tan solid N-(2-(2-((dimethylamino)methyl)azetidine-1-yl)-4-methoxy-5-nitrophenyl)acrylamide (1.0 g, yield: 56%).

$^1$H NMR: (CDCl$_3$, 400 MHz) δ6.88 (s, 1H), 6.51 (s, 1H), 6.47-6.34 (m, 2H), 5.83-5.80 (dd, J$_1$=2.8 Hz, J$_2$=8.8 Hz, 1H), 4.51-4.49 (m, 1H), 4.18-4.16 (m, 1H), 3.98 (s, 3H), 3.95-3.82 (m, 4H), 2.85-2.80 (dd, J$_1$=4.8 Hz, J$_2$=12.8 Hz, 1H), 2.60-2.49 (m, 2H), 2.32 (s, 6H), 2.30-2.15 (m, 1H).

h. Synthesis of N-(5-amino-2-(2-((dimethylamino)methyl)azetidine-1-yl)-4-methoxyphenyl)acrylamide (9)

A mixture reaction solution of N-(2-(2-((dimethylamino)methyl)azetidine-1-yl)-4-methoxy-5-nitrophenyl)acrylamide (1.6 g, 4.8 mmol) and Fe powder (1.3 g, 23.8 mmol) in ethanol (100 mL) and water (50 mL) was stirred at 50° C. for 16 hours. TLC (DCM:MeOH=10:1) showed that the reaction was complete. The reaction solution obtained after filtering through celite was concentrated and mixed with silica gel, and passed through a column (DCM:MeOH=10:1) to obtain a yellow solid N-(5-amino-2-(2-((dimethylamino)methyl)azetidine-1-yl)-4-methoxyphenyl)acrylamide (990 mg).

$^1$H NMR: (CD$_3$OD, 400 MHz) δ6.95 (s, 1H), 6.94-6.36 (m, 2H), 6.36-6.32 (m, 1H), 5.79-5.76 (m, 1H), 4.56-4.54 (dd, J$_1$=3.6 Hz, J$_2$=7.2 Hz, 1H), 3.92 (s, 3H), 3.90-3.86 (m, 1H), 3.39-3.31 (m, 3H), 2.89 (s, 6H), 2.44-2.42 (m, 1H), 2.32-2.30 (m, 1H).

i. Synthesis of (R)—N-(5-((4-(1H-pyrrole[3,2-c]pyridin-1-yl)-1,3,5-triazin-2-yl)amino)-2-(2-((dimethylamino)methyl)azetidine-1-yl)-4-methoxyphenyl)acrylamide To a solution of N-(5-amino-2-(2-((dimethylamino)methyl)azetidine-1-yl)-4-methoxyphenyl)acrylamide (400 mg, 1.30 mmol) in DMF (10 mL), 2,4-dichloro-1,3,5-triazine (197 mg, 1.30 mmol) and DIPEA (180 mg, 1.40 mmol) were added at 10° C. After the reaction solution was stirred at 0° C. for 1 hour, DIPEA (180 mg, 1.40 mmol) and 1H-pyrrolo[3,2-c]pyridine (155 mg, 1.31 mmol) were added. After the reaction was stirred at 25° C. for 5 hours, LCMS showed the reaction was complete. After the crude product was purified by prep-HPLC (chromatographic column: Waters Xbridge 150*25 5 u; mobile phase: [water (10 mM NH$_4$HCO$_3$)-ACN]; B %: 20%-40%, 10 min) and the second prep-HPLC (chromatographic column: Waters Xbridge 150*25 5 u; mobile phase: [Water (10 mM NH$_4$HCO$_3$)-ACN]; B %: 32%-62%, 10 min), a yellow solid (R)—N-(5-((4-(1H-pyrrole[3,2-c]pyridin-1-yl)-1,3,5-triazin-2-yl)amino)-2-(2-((dimethylamino)methyl)azetidine-1-yl)-4-methoxyphenyl)acrylamide (67 mg, yield: 10%) was obtained.

$^1$H NMR: (CDCl$_3$, 400 MHz) δ8.90 (s, 1H), 8.72-8.43 (m, 6H), 6.79-6.78 (d, J=3.6 Hz, 1H), 6.57 (s, 1H), 6.49-6.44 (d, J=16.8 Hz, 1H), 6.35-6.29 (m, 1H), 5.79-5.76 (d, J=10.0 Hz, 1H), 4.34 (s, 1H), 3.95-3.91 (m, 4H), 3.65-3.59 (dd, J$_1$=8.0 Hz, J$_2$=15.6 Hz, 1H), 2.74-2.69 (dd, J$_1$=5.2 Hz, J$_2$=12.8 Hz, 1H), 2.50-2.46 (m, 2H), 2.30 (s, 7H), 2.12-2.06 (m, 1H).

ESI-MS (m/z): [M+H]$^+$ 500.2, HPLC: 99.1% (220 nm).

Example 2

Synthesis of (R,E)-N-(5-((4-(1H-pyrrole[3,2-c]pyridin-1-yl)-1,3,5-triazin-2-yl)amino)-2-(2-((dimethylamino)methyl)azetidine-1-yl)-4-methoxyphenyl)-4-(dimethylamino)butene-2-amide (Compound 2)

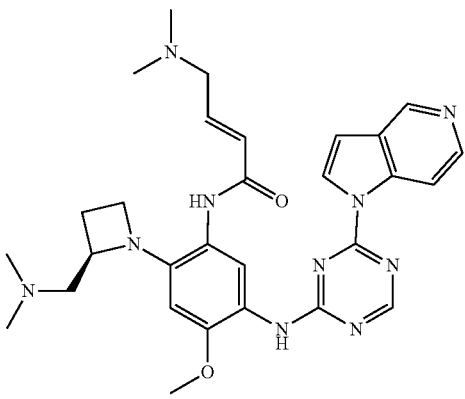 [SMILES: COc1cc(N2CC[C@@H]2CN(C)C)c(NC(=O)/C=C/CN(C)C)cc1Nc1ncnc(-n2ccc3cnccc32)n1]

Synthetic Route:

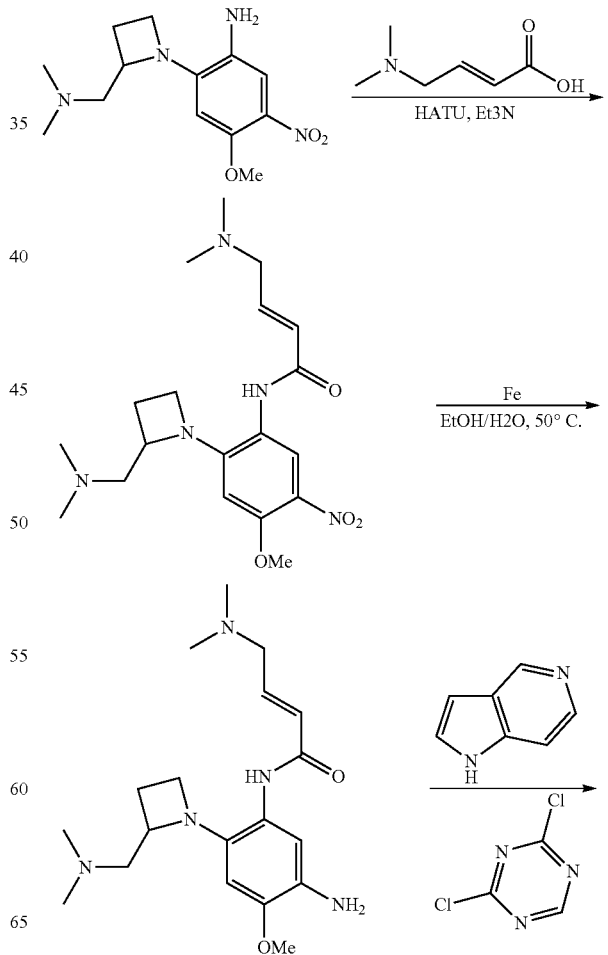

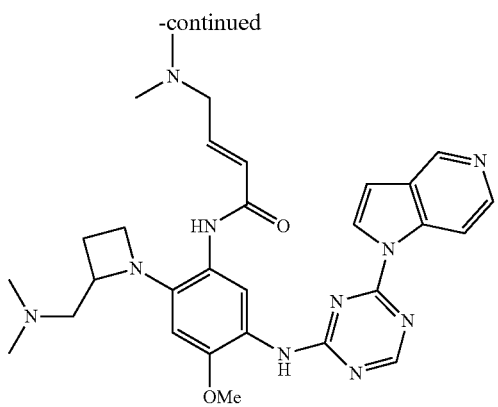

To a solution of (E)-4-(dimethylamino)but-2-enoic acid (1.8 g, 11.0 mmol, HCl) in DCM (120 mL), HATU (4.2 g, 11.0 mmol), 2-(2-((dimethylamino)methyl)azetidine-1-yl)-4-methoxy-5-nitroaniline (2.4 g, 8.6 mmol), and triethylamine (3.5 g, 34.3 mmol) were added at 25° C. After the reaction was stirred at 25° C. for 16 hours, TLC (DCM:MeOH=10:1) showed that the reaction was complete. The reaction solution was washed with water, and allowed to stand for separation. The organic phase was washed with saturated brine, dried over anhydrous sodium sulfate, filtered, and concentrated to obtain a crude product. The crude product was subjected to silica gel column chromatography (DCM:MeOH=100:1 to 10:1) to obtain a brown solid (E)-(dimethylamino)-N-(2-(2-((dimethylamino)methyl)azetidine-1-yl)-4-methoxy-5-nitrophenyl)-but ene-2-amide (2.3 g, yield: 69%).

$^1$H NMR: (CDCl$_3$, 400 MHz) δ9.54 (s, 1H), 8.06 (s, 1H), 6.99-6.93 (m, 1H), 6.14-6.10 (m, 2H), 4.66-4.64 (t, J=4.0 Hz, 1H), 4.15-4.12 (m, 1H), 3.94-3.95 (m, 4H), 3.12-3.09 (m, 2H), 3.06-2.95 (m, 1H), 2.83-2.79 (m, 1H), 2.56-2.52 (m, 2H), 2.34 (s, 6H), 2.29 (s, 6H), 1.94-1.92 (s, 6H).

(E)-(dimethylamino)-N-(2-(2-(((dimethylamino)methyl)azetidine-1-yl)-4-methoxy-5-nitrophenyl)-butene-2-amide (1.5 g, 3.8 mmol), ammonium chloride (1.1 g, 19.2 mmol), Fe powder (1.1 g, 19.0 mmol) were dissolved in a mixture of ethanol (100 mL) and water (50 mL), after the reaction mixture was stirred at 50° C. for 16 hours, TLC showed that the reaction was complete. The reaction mixture was filtered through celite and concentrated to obtain a crude product, which was purified and lyophilized by prep-HPLC (chromatographic column: Waters Xbridge 150*25 5 u; Mobile phase: [water (10 mM NH$_4$HCO$_3$)-ACN]; B %: 3%-33%, 10 min) to obtain (E)-N-(5-amino-2-(2-((dimethylamino) methyl) azetidine-1-yl)-4-methoxyphenyl)-4-(dimethylamino)-butene-2-amide (300 mg, yield: 44%).

$^1$H NMR: (CD$_3$OD, 400 MHz) δ6.99 (s, 1H), 6.89-6.81 (m, 1H), 6.54 (s, 1H), 6.33-6.29 (d, J=15.6 Hz, 1H), 4.18-4.15 (dd, J$_1$=3.2 Hz, J$_2$=7.2 Hz, 1H), 3.86-3.83 (m, 4H), 3.31-3.29 (m, 1H), 3.18-3.16 (m, 2H), 2.65-2.64 (m, 1H), 2.53-2.51 (m, 1H), 2.34-2.32 (m, 16H), 2.29-2.13 (s, 1H).

To a solution of (E)-N-(5-amino-2-(2-((dimethylamino)methyl)azetidine-1-yl)-4-methoxyphenyl)-4-(dimethylamino)-butene-2-amide (130 mg, 0.36 mmol) in DMF (4 mL), 2,4-dichloro-1,3,5-triazine (54 mg, 0.36 mmol) and DIPEA (49 mg, 0.38 mmol) were slowly added dropwise at 0° C., the reaction was carried out at 0° C. for 1 hour. DIPEA (49 mg, 0.38 mmol) was added, followed by 1H-pyrrolo[3,2-c]pyridine (43 mg, 0.36 mmol). After the reaction solution was stirred at 25° C. for 16 hours, LCMS showed that the reaction was complete. The reaction mixture was purified by prep-HPLC (chromatographic column: Waters Xbridge 150*25 5 u; mobile phase: [water (10 mM NH$_4$HCO$_3$)-ACN]; B %: 23%-43%, 8 min), and lyophilized to obtain a white solid (R,E)-N-(5-((4-(1H-pyrrole[3,2-c]pyridin-1-yl)-1,3,5-triazin-2-yl)amino)-2-(2-((dimethylamino)meth yl)azetidine-1-yl)-4-methoxyphenyl)-4-(dimethylamino) butene-2-amide (13 mg, yield: 6%).

$^1$H NMR: (CDCl$_3$, 400 MHz) δ8.90 (s, 1H), 8.72-8.43 (m, 6H), 6.79-6.78 (d, J=3.6 Hz, 1H), 6.57 (s, 1H), 6.49-6.44 (d, J=16.8 Hz, 1H), 6.35-6.29 (m, 1H), 5.79-5.76 (d, J=10.0 Hz, 1H), 4.34 (s, 1H), 3.95-3.91 (m, 4H), 3.65-3.59 (dd, J$_1$=8.0 Hz, J$_2$=15.6 Hz, 1H), 2.74-2.69 (dd, J$_1$=5.2 Hz, J$_2$=12.8 Hz, 1H), 2.50-2.46 (m, 2H), 2.30 (s, 7H), 2.12-2.06 (m, 1H).

ESI-MS (m/z): [M+H]$^+$ 556.2, HPLC: 99.1%(220 nm).

Example 3

Synthesis of N-(2-((2-(dimethylamino)ethyl)(methyl)amino)-5-((4-(3-fluoro-1H-indazol-1-yl)-1,3,5-triazin-2-yl)amino)-4-methoxyphenyl)acrylamide (Compound 3)

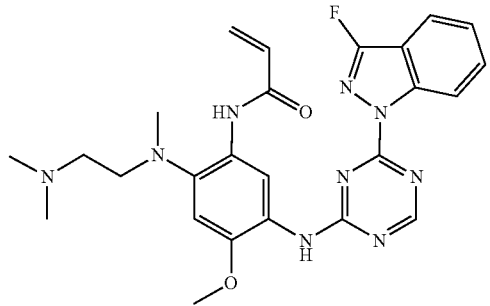 [SMILES: C=CC(=O)Nc1cc(Nc2ncnc(-n3nc(F)c4ccccc43)n2)c(OC)cc1N(C)CCN(C)C]

a. Synthesis of 4-(3-fluoro-1H-indazol-1-yl)-N-(4-fluoro-2-methoxy-5-nitrophenyl)-1,3,5-triazin-2-amine

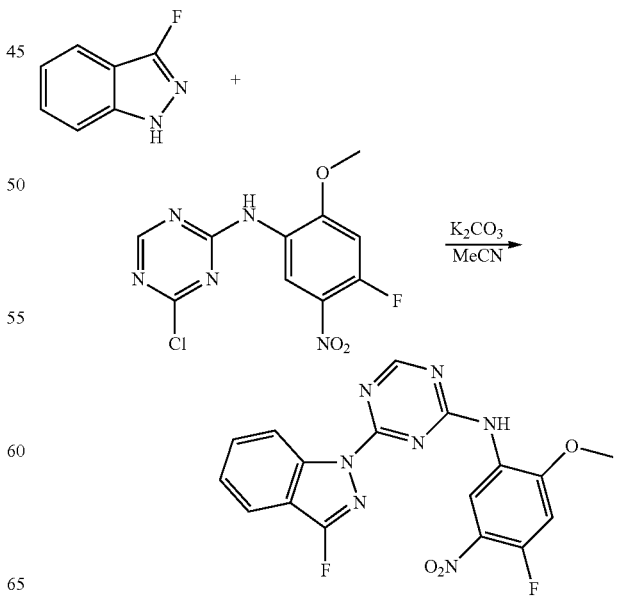

3-Fluoro-1H-indazole (200 mg, 1.47 mmol) and 4-chloro-N-(4-fluoro-2-methoxy-5-nitrophenyl)-1,3,5-triazin-2-amine (420 mg, 1.40 mmol) were dissolved in acetonitrile (20 ml), K$_2$CO$_3$ (386.7 mg, 2.80 mmol) was added, and stirred at room temperature overnight. LC-MS was used to detect the progress of the reaction. After the reaction was completed, it was quenched by adding water, extracted with acetic ether (50 ml×3), dried over anhydrous sodium sulfate, and rotary dried to obtain the crude product 4-(3-fluoro-1H-indazole-1-yl)-N-(4-fluoro-2-methoxy-5-nitrophenyl)-1,3,5-triazin-2-amine.

b. Synthesis of N$^1$-(2-(dimethylamino)ethyl)-N$^4$-(4-(3-fluoro-1H-indazol-1-yl)-1,3,5-triazin-2-yl)-5-methoxy-N$^1$-methyl-2-nitrophenyl-1,4-diamine

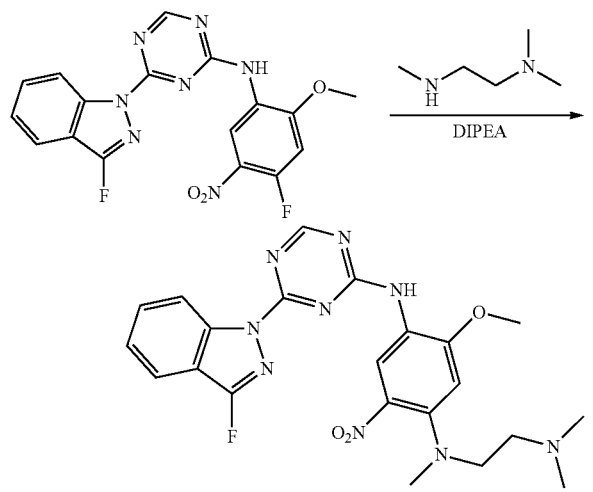

The crude product obtained in the previous step 4-(3-fluoro-1H-indazole-1-yl)-N-(4-fluoro-2-methoxy-5-nitrophenyl)-1,3,5-triazin-2-amine and N$^1$,N$^1$,N$^2$-trimethylethyl-1,2-diamine (123.5 mg, 1.2 mmol) were dissolved in DMA (10 ml), and DIPEA (260.4 mg, 2.0 mmol) was added, under microwave conditions, the reaction was carried out at 80° C. for 1 hour. LC-MS was used to detect the progress of the reaction. After the reaction was completed, it was quenched by adding water, extracted with acetic ether (3 ml×3), dryed over anhydrous sodium sulfate, and rotary dried to obtain the crude product N$^1$-(2-(dimethylamino)ethyl)-N$^4$-(4-(3-fluoro-1H-indazol-1-yl)-1,3,5-triazin-2-yl)-5-methoxy-N-methyl-2-nitrophenyl-1,4-diamine.

c. Synthesis of N$^1$-(2-(dimethylamino)ethyl)-N$^4$-(4-(3-fluoro-1H-indazol-1-yl)-1,3,5-triazin-2-yl)-5-methoxy-N$^1$-methylphenyl-1,2,4-triamine

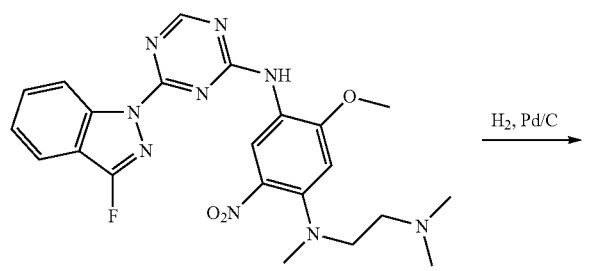

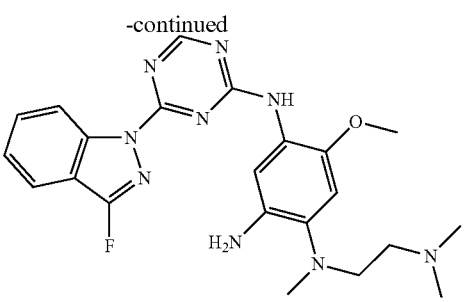

The crude product obtained in the previous step, N$^1$-(2-(dimethylamino)ethyl)-N$^4$-(4-(3-fluoro-1H-indazol-1-yl)-1,3,5-triazin-2-yl)-5-methoxy-N-methyl-2-nitrophenyl-1,4-diamine was dissolved in CH$_3$OH (20 ml), Pd/C (50 mg) was added, and reduced overnight at 1 standard atmospheric pressure under H2 atmosphere. LC-MS was used to detect the progress of the reaction, after the reaction was completed, the Pd/C was filtered off with suction, washed with acetic ether (5 ml×3), and rotary dried to obtain the crude product N$^1$-(2-(dimethylamino)ethyl)-N$^4$-(4-(3-fluoro-1H-indazol-1-yl)-1,3,5-triazin-2-yl)-5-methoxy-N$^1$-methylphenyl-1,2,4-triamine.

d. Synthesis of N-(2-((2-(dimethylamino)ethyl)(methyl)amino)-5-((4-(3-fluoro-1H-indazol-1-yl)-1,3,5-triazin-2-yl)amino)-4-methoxyphenyl)acrylamide

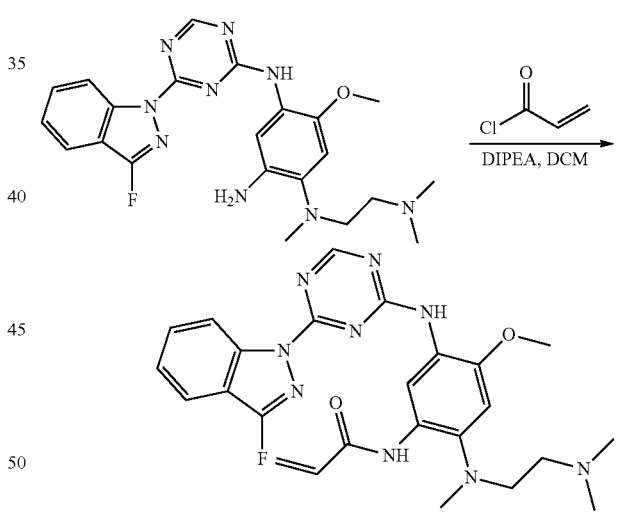

The crude product obtained in the previous step N$^1$-(2-(dimethylamino)ethyl)-N$^4$-(4-(3-fluoro-1H-indazol-1-yl)-1,3,5-triazin-2-yl)-5-methoxy-N$^1$-methylphenyl-1,2,4-triamine and DIPEA (219.7 mg, 1.7 mmol) were dissolved in DCM (20 ml), and acryloyl chloride was added (67.7 mg, 0.75 mmol), the reaction was carried out at room temperature for 30 min. LC-MS was used to detect the progress of the reaction. After the reaction was completed, it was quenched by saturated sodium bicarbonate solution, extracted with acetic ether (30 ml×3), and rotary dried to obtain the crude product 8, to obtain a white solid N-(2-((2-(dimethylamino)ethyl)(methyl)amino)-5-((4-(3-fluoro-1H-indazole-1-yl)-1,3,5-triazin-2-yl) amino)-4-methoxyphenyl) acrylamide (10 mg) separated by preparative liquid chromatography. 20 $^1$H NMR: (500 MHz, DMSO-d6) δ 9.84 (br, 1H), 9.58 (br, 1H), 9.38 (br, 1H), 8.66 (br, 1H), 8.02 (s, 1H), 7.88 (br, 1H), 7.46 (m, 2H), 7.08 (m, 1H), 6.66 (m, 1H), 6.28 (d, J=17 Hz, 1H), 5.78 (d, J=12 Hz, 1H), 3.82 (s, 3H), 3.33 (m, 7H), 2.83 (s, 3H), 2.82 (s, 3H), 2.64 (m, 4H). $^{19}$F NMR (376 MHz, DMSO-d6) δ−73.7.

MS (ESI) $[C_{25}H_{28}FN_9O_2H]^+$ (M+H)$^+$: m/z 506.24.

Example 4

Synthesis of N-(2-((2-(dimethylamino)ethyl)(methyl)amino)-4-methoxy-5-((4-(8-iodoimidazo[1,2-a]pyridin-3-yl) pyrimidin-2-yl)amino)phenyl)acrylamide (Compound 4)

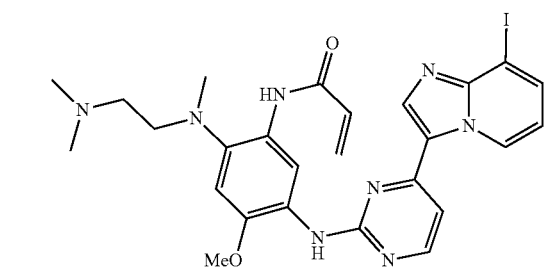 [SMILES: C=CC(=O)Nc1cc(Nc2nccc(-c3cnc4c(I)cccn34)n2)c(OC)cc1N(C)CCN(C)C]

a. Synthesis of (E)-2-chloro-4-(2-ethoxyvinyl)pyrimidine

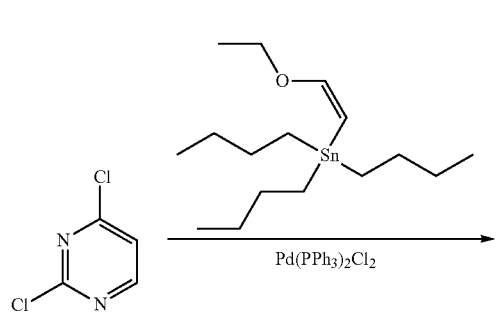

2,4-Dichloropyrimidine (1.00 g, 6.71 mmol) and (Z)-tributyl(2-ethoxyvinyl)stannane (2.67 g, 7.38 mmol) were dissolved in acetonitrile (20 mL), Pd(PPh$_3$)$_2$Cl$_2$ (471 mmg, 671 umol) was added under nitrogen protection. After the reaction mixture was stirred at 80° C. for 3 hours, TLC showed that the reaction was complete. CsF solution (15 mL) was added, and the reaction mixture was stirred at 25° C. for 1 hour. LCMS showed that the reaction was complete. The reaction solution was extracted with acetic ether (30 mL×2), washed with water (30 mL), dried over anhydrous sodium sulfate, concentrated under reduced pressure and mixed with silica gel, and passed through the column (PE:EA=10:1) to obtain a white solid (E)-2-chloro-4-(2-ethoxyvinyl)pyrimidine (1.00 g, yield: 75%).

b. Synthesis of 3-(2-chloropyrimidin-4-yl)-8-iodoimidazo[1,2-a]pyridine

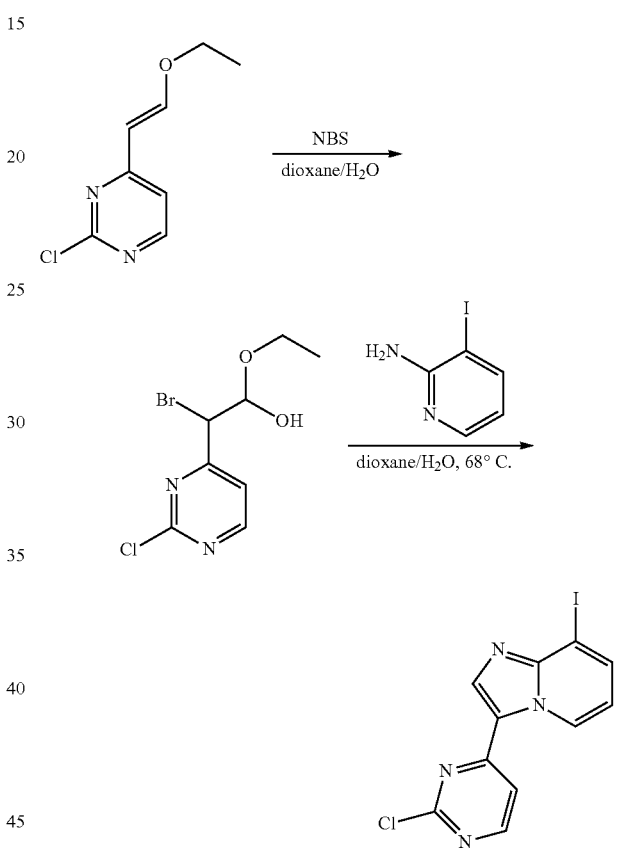

The obtained white solid (E)-2-chloro-4-(2-ethoxyvinyl) pyrimidine (1.00 g, 5.42 mmol) was dissolved in dioxane (20 mL) and water (4 mL) and NBS (1.06 g, 5.96 mmol) was added, the reaction solution was stirred at 25° C. for 1 hour. 3-iodopyrimidin-2-amine (1.19 g, 5.42 mmol) was added in portions, and the reaction mixture was stirred at 68° C. for 3 hours. After LCMS showed the reaction was complete, water (40 mL) was added, and the solvent was distilled off under reduced pressure. The aqueous solution was extracted with acetic ether (30 mL×3), and the combined organic phases were washed with water (20 mL), dried over anhydrous sodium sulfate, concentrated under reduced pressure and mixed with silica gel, and passed through the column (PE:EA=5:1 to 2:1) to obtain a yellow solid 3-(2-chloropyrimidin-4-yl)-8-iodoimidazo[1,2-a]pyridine (1.93 g, yield: 60.9%).

c. Synthesis of N-(4-fluoro-2-methoxy-5-nitrophenyl)-4-(8-iodoimidazole[1,2-a]pyridin-3-yl)pyrimidin-2-amine

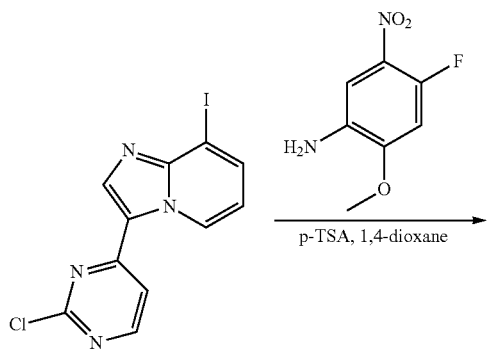

3-(2-Chloropyrimidin-4-yl)-8-iodoimidazo[1,2-a]pyridine (1.93 g, 5.41 mmol) and 4-fluoro-2-methoxy-5-nitroaniline (1.31 g, 7.04 mmol) were dissolved in dioxane (20 mL), p-toluenesulfonic acid (1.12 g, 6.50 mmol) was added, and the reaction solution was stirred at 85° C. for 16 hours. After LCMS showed the reaction was complete, water (70 mL) was added and stirred for 30 minutes, filtered to obtain a crude solid, and the filter cake was washed with water (20 mL). The solid was dissolved in THF (50 mL) and the solvent was distilled off under reduced pressure to obtain a yellow solid N-(4-fluoro-2-methoxy-5-nitrophenyl)-4-(8-iodoimidazole[1,2-a]pyridin-3-yl)pyrimidin-2-amine (1.0 g, yield: 27%).

d. Synthesis of $N^1$-(2-(dimethylamino)ethyl)-$N^4$-(4-(8-iodoimidazole[1,2-a]pyridin-3-yl)pyrimidin-2-yl)-5-methoxy-$N^1$-methyl-2-nitrophenyl-1,4-diamine

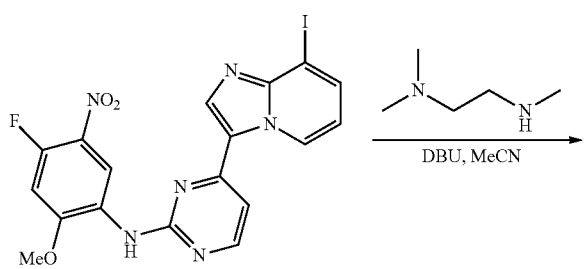

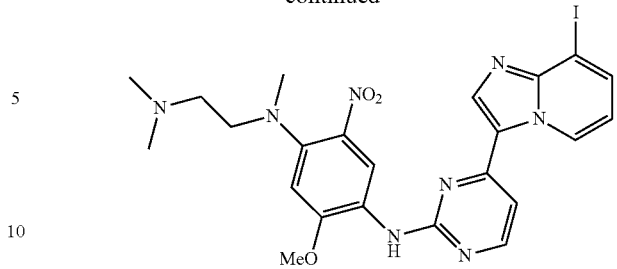

N-(4-fluoro-2-methoxy-5-nitrophenyl)-4-(8-iodoimidazole[1,2-a]pyridin-3-yl)pyrimidin-2-amine (1.00 g, 1.46 mmol) and $N^1,N^1,N^2$-trimethylethane-1,2-diamine (133 mg, 1.30 mmol) were dissolved in acetonitrile (20 mL), DBU (200 mg, 1.32 mmol) was added, the reaction mixture was stirred at 85° C. for 16 hours. After TLC showed that the reaction was complete, water (50 mL) was added, and the solvent was distilled off under reduced pressure. The aqueous phase was extracted with DCM (50 mL×3), the combined organic phases were washed with water (50 mL), dried over anhydrous sodium sulfate, concentrated under reduced pressure and mixed with silica gel, and passed through the column (DCM:MeOH=10:1) to obtain $N^1$-(2-(dimethylamino)ethyl)-$N^4$-(4-(8-iodoimidazole[1,2-a]pyridin-3-yl)pyrimidin-2-yl)-5-methoxy-$N^1$-methyl-2-nitrophenyl-1,4-diamine (0.9 g, yield: 75.3%).

e. Synthesis of $N^1$-(2-(dimethylamino)ethyl)-$N^4$-(4-(8-iodoimidazole[1,2-a]pyridin-3-yl)pyrimidin-2-yl)-5-methoxy-N-methylphenyl-1,2,4-triamine

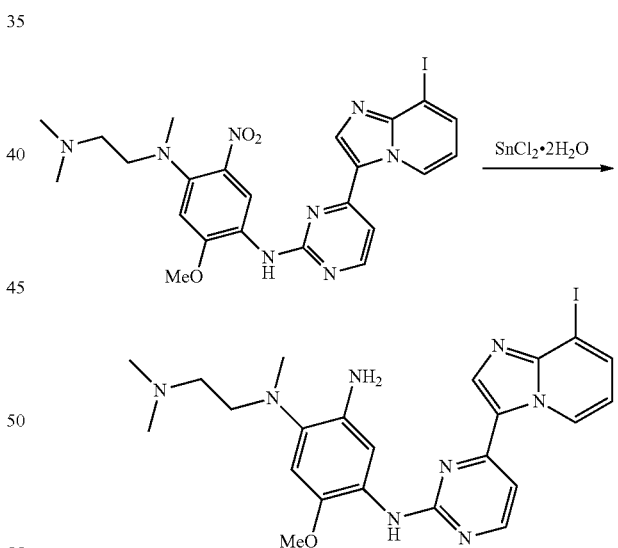

$N^1$-(2-(dimethylamino)ethyl)-$N^4$-(4-(8-iodoimidazole[1,2-a]pyridin-3-yl)pyrimidin-2-yl)-5-methoxy-$N^1$-methyl-2-nitrophenyl-1,4-diamine (0.9 g, 1.53 mmol) was dissolved in ethanol (20 mL), $SnCl_2 \cdot 2H_2O$ (1.73 g, 7.65 mmol) and HCl (12 M, 2.70 mL) were added, and the reaction solution was stirred at 45° C. for 2.5 hours. After LCMS showed the reaction was complete, water (100 mL) was added, and the solvent was concentrated under reduced pressure. The aqueous phase was extracted with dichloromethane (50 mL×3), and the combined organic phases were washed with water (50 mL), dried over anhydrous sodium sulfate, and concentrated under reduced pressure, purified by prep-HPLC (chromatographic column: Xtimate C18 150*25 mm*5 um; mobile phase: [water (0.225% FA)-ACN]; B %: 4%-34%, 7 min) to obtain $N^1$-(2-(dimethylamino)ethyl)-$N^4$-(4-(8-iodoimidazole[1,2-a]pyridin-3-yl)pyrimidin-2-yl)-5-methoxy-$N^1$-methylphenyl-1,2,4-triamine (350 mg, yield: 41.0%).

$^1$H NMR (CDCl$_3$, 400 MHz): δ 8.50 (d, J=5.2 Hz, 1H), 8.44 (s, 1H), 8.17 (dd, J$_1$=1.2 Hz, J$_2$=6.8 Hz, 1H), 8.10 (s, 1H), 7.73-7.71 (m, 1H), 7.66-7.63 (m, 2H), 6.71 (s, 1H), 6.59-6.56 (m, 1H), 3.84 (s, 3H), 2.99-2.96 (m, 2H), 2.67 (s, 3H), 2.45-2.41 (m, 2H), 2.28 (s, 6H).

f. Synthesis of N-(2-((2-(dimethylamino)ethyl)(methyl)amino)-4-methoxy-5-((4-(8-iodoimidazo[1,2-a]pyridin-3-yl) pyrimidin-2-yl)amino)phenyl)acrylamide

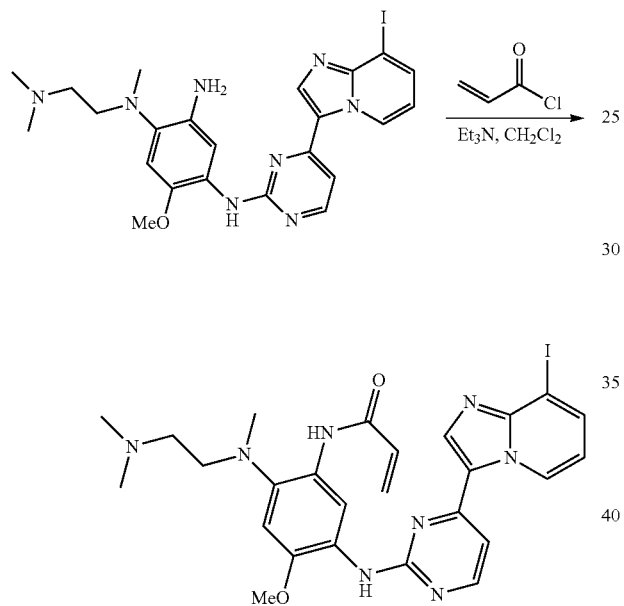

$N^1$-(2-(dimethylamino)ethyl)-$N^4$-(4-(8-iodoimidazole[1,2-a]pyridin-3-yl)pyrimidin-2-yl)-5-methoxy-$N^1$-methylphenyl-1,2,4-triamine (350 mg, 627 umol) and triethylamine (76.1 mg, 752 umol) were dissolved in dichloromethane (10 mL), acryloyl chloride (68.1 mg, 752 umol) diluted in dichloromethane (3 mL) was adduced, the reaction was stirred at 25° C. for 3 hours. LCMS showed the reaction was complete. The reaction solution was quenched with water (20 mL), extracted with dichloromethane (20 mL×3), and the combined organic phases were washed with water (20 mL), dried over anhydrous sodium sulfate, concentrated under reduced pressure, mixed with silica gel, passed through the column (DCM:MeOH=10:1) to obtain N-(2-((2-(dimethylamino)ethyl)(methyl)amino)-4-methoxy-5-((4-(8-iodoimidazo[1,2-a]pyridin-3-yl) pyrimidin-2-yl)amino)phenyl)acrylamide (190 mg, yield: 49.5%).

$^1$H NMR (CDCl$_3$, 400 MHz): δ 10.12 (s, 1H), 9.94 (s, 1H), 9.85 (s, 1H), 8.49 (d, J=5.2 Hz, 1H), 8.27 (d, J=6.8 Hz, 1H) 7.86 (s, 1H), 7.72-7.68 (m, 2H), 6.78 (s, 1H), 6.57-6.48 (m, 3H), 5.78-6.75 (m, 1H), 3.89 (s, 3H) 2.96 (s, 2H) 2.71 (s, 3H) 2.35 (s, 8H). ESI-MS (m/z): [M+H]$^+$ 613.3.

Example 5

Synthesis of N-(2-((2-(dimethylamino)ethyl)(methyl)amino)-5-((4-(8-fluoroimidazo[1,2-a]pyridin-3-yl)pyrimidin-2-yl)amino)-4-methoxyphenyl) acrylamide (Compound 5)

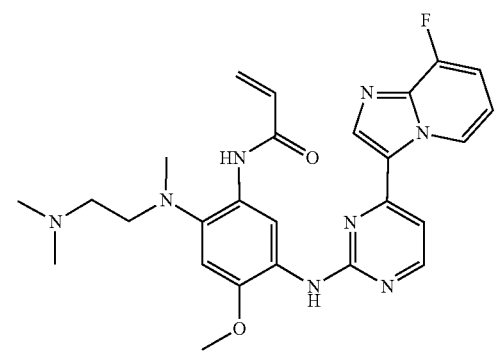 [SMILES: C=CC(=O)Nc1cc(Nc2nccc(-c3cnc4c(F)cccn34)n2)c(OC)cc1N(C)CCN(C)C]

a. Synthesis of 8-fluoroimidazo[1,2-a]pyridine

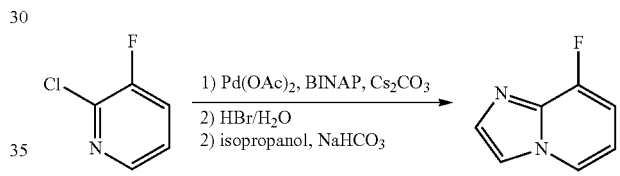

2-Chloro-3-fluoropyridine (21 g, 159 mmol), benzophenone imine (32 g, 176 mmol), BINAP (4.96 g, 7.97 mmol) and cesium carbonate (73 g, 224 mmol) were dissolved in toluene (370 mL), Pd(OAc)$_2$ (1.45 g, 6.46 mmol) was added under nitrogen protection, and the reaction was stirred at 100° C. for 48 hours. LCMS showed the reaction was complete, and the reaction mixture was filtered through celite, and the filter cake was rinsed with acetic ether. The organic phase was extracted with water (200 mL×2), concentrated under reduced pressure, and the solvent was removed. The crude product was dissolved in HBr (29.8 g, 147 mmol, 20 mL) and water (20 mL). After the reaction was stirred at 90° C. for 30 minutes, isopropyl alcohol (300 mL) and sodium bicarbonate (68.4 g, 814 mmol) were added, and the reaction was stirred at 25° C. for 20 minutes. After filtration, the solid was rinsed with isopropanol (200 mL). After the filtrate was stirred at 55° C. for 16 hours, LCMS showed that the reaction was complete. After concentration under reduced pressure, it was dissolved in acetic ether (300 mL) and washed with water (200 mL). The aqueous phase was extracted with acetic ether (200 mL×2). The organic phases were combined and dried over anhydrous sodium sulfate, concentrated under reduced pressure, mixed with silica gel, and passed through the column (PE:EA=1:1) to obtain a brown solid 8-fluoroimidazo[1,2-a]pyridine (14.0 g, yield: 64.4%).

$^1$H NMR (CDCl$_3$, 400 MHz): δ 7.94-7.91 (m, 1H), 7.62-7.61 (m, 2H), 6.85-6.81 (m, 1H), 6.70-6.65 (m, 1H).

b. Synthesis of 3-bromo-8-fluoroimidazo[1,2-a]pyridine

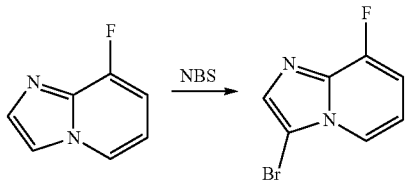

8-Fluoroimidazo[1,2-a]pyridine (3.00 g, 22.0 mmol) was dissolved in dichloromethane (30 mL), NBS (3.92 g, 22.0 mmol) was added in portions, and the reaction solution was stirred at 25° C. for 16 hours. LCMS showed the reaction was complete, and the reaction solution was diluted with dichloromethane (50 mL) and washed with water (50 mL×2). The organic phase was dried with anhydrous sodium sulfate, distilled under reduced pressure for removing solvent, and purified through column (PE:EA=5:1) to obtain brown solid 3-bromo-8-fluoroimidazo[1,2-a]pyridine (3.50 g, yield: 73.8%).

$^1$H NMR ES10609-7-P1B (CDCl$_3$, 400 MHz): δ 7.97-7.95 (m, 1H), 7.64 (s, 1H), 7.98-7.94 (m, 1H), 7.89-7.84 (m, 1H).

c. Synthesis of 8-fluoro-3-(tri-n-butylvinyl)imidazo[1,2-a]pyridine

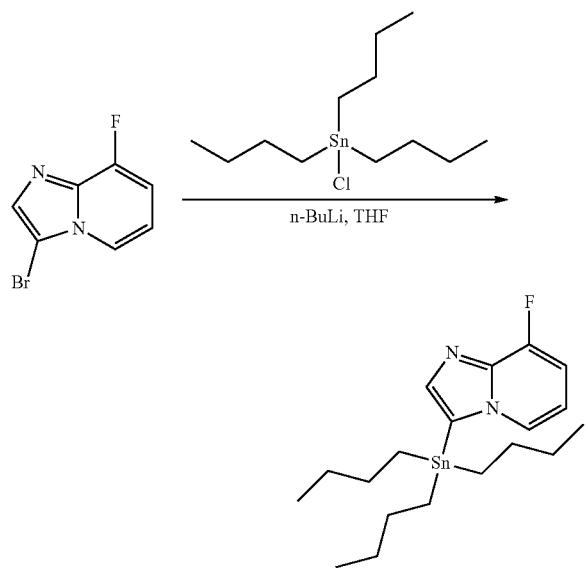

3-Bromo-8-fluoroimidazo[1,2-a]pyridine (1.00 g, 4.65 mmol) was dissolved in THF (20 mL), n-BuLi (2.5M, 2.23 mL) was added dropwise at minus 70° C., and the reaction solution was stirred at minus 70° C. for 30 minutes. Tri-n-butyltin chloride was dissolved in THF (5 mL) and slowly added dropwise to the reaction solution at minus 70° C. The reaction solution was heated to 25° C. and stirred for 3 hours. LCMS showed the reaction was complete. The reaction was quenched with water (20 mL), the aqueous phase was extracted with acetic ether (20 mL×3), the combined organic phases were washed with water (20 mL×2), dried over anhydrous sodium sulfate, and distilled under reduced pressure to obtain brown oily compound 8-fluoro-3-(tri-n-butyltinyl)imidazo[1,2-a]pyridine (2.39 g), used in the next reaction without further purification.

d. Synthesis of 3-(2-chloropyrimidin-4-yl)-8-fluoro-imidazo[1,2-a]pyridine

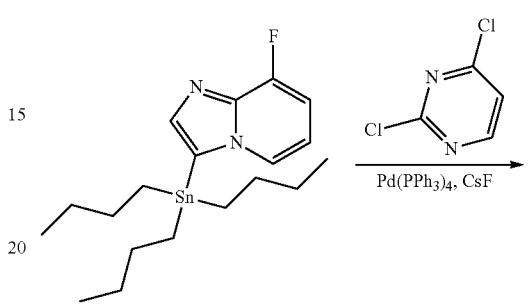

8-Fluoro-3-(tri-n-butyltinyl)imidazo[1,2-a]pyridine (2.00 g, 4.70 mmol), 2,4-dichloropyrimidine (771 mg, 5.17 mmol) and cesium carbonate (1.43 g, 9.41 mmol) were dissolved in toluene (40 mL), Pd(PPh$_3$)$_4$ (544 mg, 470 umol) was added under the protection of nitrogen, and the reaction solution was stirred at 90° C. for 16 hours. TLC (PE:EA=2:1) showed that the reaction was complete. Water (50 mL) was added. The aqueous phase was extracted with acetic ether (50 mL×3), dried over anhydrous sodium sulfate, concentrated under reduced pressure, and mixed with silica gel, purified by passing through the column (PE:EA=2:1 to 1:1) to obtain 3-(2-chloropyrimidin-4-yl)-8-fluoroimidazo[1,2-a]pyridine (650 mg, yield: 48.4%).

For the synthesis of the remaining intermediates and final products, referring to a method similar to Example 19, N-(2-((2-(dimethylamino)ethyl)(methyl)amino)-5-((4-(8-fluoroimidazo[1,2-a]pyridin-3-yl)pyrimidin-2-yl)amino)-4-methoxyphenyl)acrylamide (170 mg, yield: 39.9%) could be obtained.

$^1$H NMR (CDCl$_3$, 400 MHz): δ 10.14 (s, 1H), 9.70 (d, J=6.8 Hz, 1H), 9.36 (s, 1H), 8.46 (d, J=5.2 Hz, 1H) 8.26 (s, 1H), 7.43 (s, 1H), 7.09 (d, J=5.2 Hz, 1H), 6.99-6.97 (m, 1H), 6.82-6.78 (m, 2H), 6.37-6.28 (m, 2H), 5.69-5.66 (m, 1H) 3.88 (s, 3H) 2.89 (s, 2H), 2.72 (s, 3H) 2.33 (s, 2H), 2.28 (s, 6H).

ESI-MS (m/z): [M+H]$^+$ 505.5.

Example 6

Synthesis of N-(2-((2-(dimethylamino)ethyl)(methyl)amino)-4-methoxy-5-((4-(8-trifluoromethylimidazo[1,2-a]pyridin-3-yl)pyrimidin-2-yl)amino)phenyl)acrylamide (Compound 6)

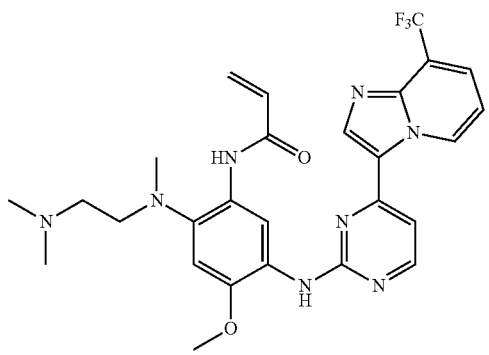 [SMILES: C=CC(=O)Nc1cc(Nc2nccc(-c3cnc4c(C(F)(F)F)cccn34)n2)c(OC)cc1N(C)CCN(C)C]

In a similar method to Example 4, N-(2-((2-(dimethylamino)ethyl)(methyl)amino)-4-methoxy-5-((4-(8-trifluoromethylimidazo[1,2-a]pyridin-3-yl)pyrimidin-2-yl)amino)phenyl)acrylamide (200 mg, 39.2%) could be obtained.

$^1$H NMR (CDCl$_3$, 400 MHz): δ 10.3 (s, 1H), 9.95 (s, 1H), 9.89 (s, 1H), 8.51-8.45 (m, 2H), 7.89 (s, 1H), 7.72 (d, J=5.2 Hz, 1H), 7.55 (d, J=7.2 Hz, 1H), 6.90-6.86 (m, 1H), 6.53-6.37 (m, 2H), 5.77 (d, J$_1$=2.0 Hz, d, J$_2$=9.6 Hz, 1H), 3.90 (s, 3H), 2.92-2.89 (m, 2H), 2.75-2.72 (m, 3H), 2.27 (s, 8H).

ESI-MS (m/z): [M+H]$^+$ 555.3.

Example 7

Synthesis of N-(2-((2-(dimethylamino)ethyl(methyl)amino)-5-((4-(3-fluoro-1H-indazol-1-yl)pyrimidine-2-yl)amino)-4-methoxyphenyl)acrylamide (Compound 7)

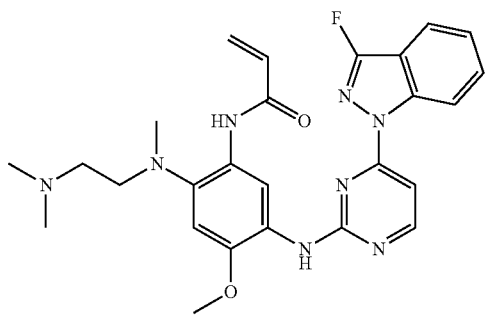 [SMILES: C=CC(=O)Nc1cc(Nc2nccc(-n3nc(F)c4ccccc43)n2)c(OC)cc1N(C)CCN(C)C]

In a similar method to Example 4, N-(2-((2-(dimethylamino)ethyl(methyl)amino)-5-((4-(3-fluoro-1H-indazol-1-yl)pyrimidine-2-yl)amino)-4-methoxyphenyl)acrylamide (100 mg, yield: 22.3%) could be obtained.

$^1$H NMR (CDCl$_3$, 400 MHz): δ 10.3 (s, 1H), 8.78-8.74 (m, 2H), 8.41 (d, J=6.0 Hz, 1H), 7.72 (d, J=8.0 Hz, 1H), 7.58-7.54 (m, 1H), 7.33-7.30 (m, 2H), 6.95 (d, J=6.0 Hz, 1H), 6.84 (s, 1H), 6.46-6.42 (m, 1H), 6.34-6.27 (m, 1H), 5.73-5.71 (m, 1H), 3.86 (s, 3H), 2.94-2.88 (m, 2H), 2.74 (s, 3H), 2.35-2.33 (m, 2H), 2.29 (s, 6H).

ESI-MS (m/z): [M+H]$^+$ 505.3.

Example 8

Synthesis of N-(2-((2-(dimethylamino)ethyl)(methyl)amino)-4-methoxy-5-((4-(5-methoxy-1-methyl-1H-indol-3-yl)-1,3,5-triazin-2-yl)amino)phenyl)acrylamide (Compound 8)

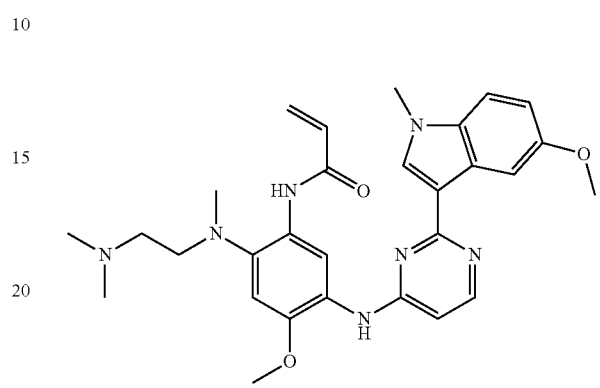

a. Synthesis of 5-methoxy-1-methyl-1H-indole

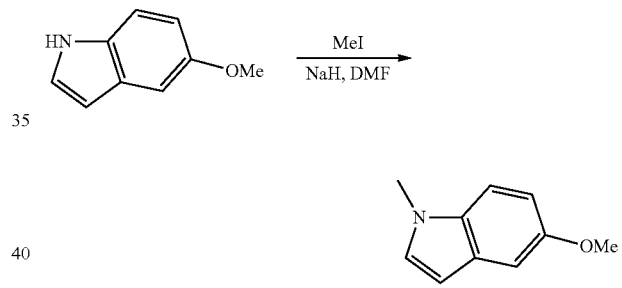

NaH (3.10 g, 77.5 mmol, 60% purity) was added to DMF (200 mL), 5-methoxyindole (9.50 g, 64.5 mmol) was added at 0° C., and stirred at this temperature for 20 minutes, methyl iodide (10.9 g, 77.5 mmol, 4.82 mL) dissolved in DMF (20 mL) was added, and after the reaction was stirred at 0-20° C. for 2 hours, LCMS showed that the reaction was complete. The reaction mixture was poured into water (500 mL), the filtered solid was dissolved in acetic ether (300 mL), dried over anhydrous sodium sulfate, and concentrated under reduced pressure, and the crude product was purified by silica gel column chromatography (petroleum ether: acetic ether=10:1) to obtain a light yellow solid 5-methoxy-1-methyl-1H-indole (10.0 g, 62.0 mmol, yield: 96.1%).

$^1$H NMR (CDCl$_3$, 400 MHz): δ 7.22 (d, J=8.8 Hz, 1H), 7.10 (d, J=2.0 Hz, 1H), 7.02 (d, J=2.4 Hz, 1H), 6.90 (dd, J1=2.4 Hz, J2=8.8 Hz, 1H), 6.41 (d, J=2.4 Hz, 1H), 3.86 (s, 3H), 3.77 (s, 3H).

b. Synthesis of 3-(4-chloro-1,3,5-triazin-2-yl)-5-methoxy-1-methyl-1H-indole

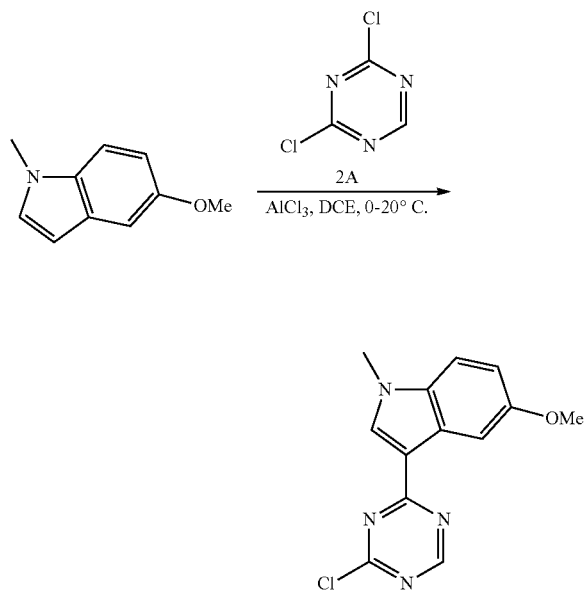

After dissolving compound 2A (8.70 g, 58.0 mmol) in dichloroethane DCE (200 mL), AlCl₃ (8.44 g, 63.3 mmol) was added at 0° C. The reaction was stirred at this temperature for 40 minutes, and 5-methoxy-1-methyl-TH-indole (8.5 g, 52.7 mmol) dissolved in dimethoxyethane DCE (40 mL) was added to the reaction mixture in portions over 40 minutes and stirred at 0-20° C. for 3 hours, LCMS showed the reaction was complete. The reaction mixture was poured into ice water (400 mL) and filtered. The obtained solid was dissolved in dichloromethane DCM (300 mL), dried over anhydrous sodium sulfate, concentrated under reduced pressure and subjected to silica gel column chromatography (petroleum ether:acetic ether=2:1) to obtain a yellow solid 3-(4-chloro-1,3,5-triazin-2-yl)-5-methoxy-1-methyl-1H-indole (1.00 g, 1.60 mmol, yield: 3.04%).

c. Synthesis of N-(4-fluoro-2-methoxy-5-nitrophenyl)-4-(5-methoxy-1-methyl-1H-indol-3-yl)-1,3,5-triazin-2-amine

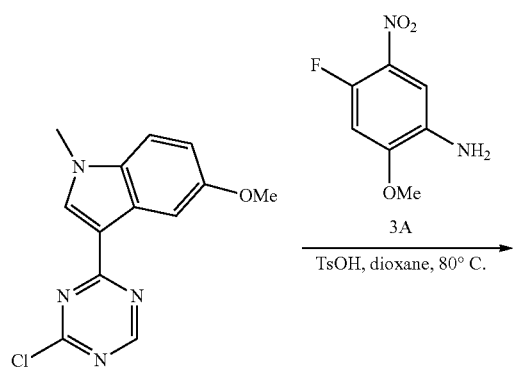

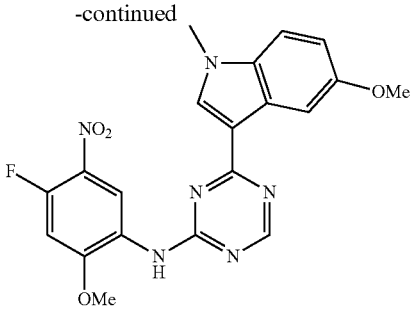

To a solution of 3-(4-chloro-1,3,5-triazin-2-yl)-5-methoxy-1-methyl-TH-indole (1.00 g, 3.64 mmol) and compound 3A (813 mg, 4.37 mmol) in 2,4-dioxane (40 mL), TsOH (815 mg, 4.73 mmol) was added, and the reaction solution was stirred at 80° C. for 16 hours. LCMS showed the reaction was complete. The reaction mixture was poured into ice water (300 mL), the solid was filtered and purified by titration with MeCN:H₂O (1:1, 50 mL) to obtain a brown solid N-(4-fluoro-2-methoxy-5-nitrophenyl)-4-(5-methoxy-1-methyl-TH-indol-3-yl)-1,3,5-triazin-2-amine (860 mg, 2.03 mmol, yield: 55.6%).

d. Synthesis of N¹-(2-(dimethylamino)ethyl)-5-methoxy-N⁴-(4-(5-methoxy-1-methyl-1H-indol-3-yl)-1,3,5-triazin-2-yl)-N¹-methyl-2-nitrophenyl-1,4-diamine

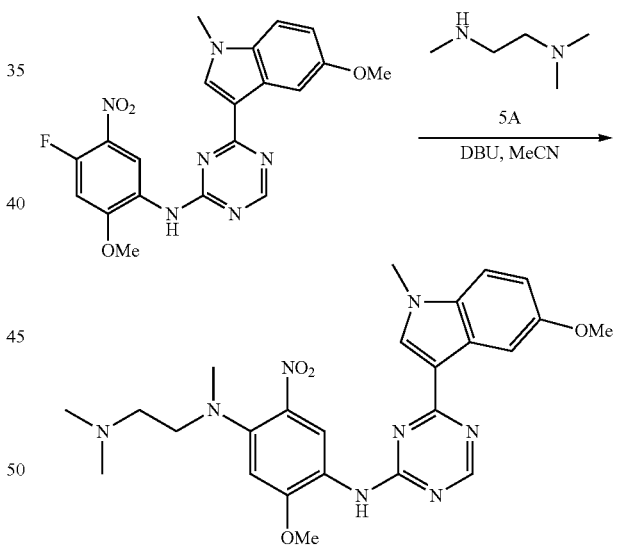

N-(4-fluoro-2-methoxy-5-nitrophenyl)-4-(5-methoxy-1-methyl-1H-indol-3-yl)-1,3,5-triazin-2-amine (860 mg, 2.03 mmol) was dissolved in acetonitrile ACN (30 mL), compound 5A (414 mg, 4.05 mmol, 527 μL) and DBU (617 mg, 4.05 mmol, 611 μL) were added, the reaction mixture was stirred at 80° C. for 1 hour, and LCMS showed that the reaction was complete. After concentration under reduced pressure, it was redissolved in dichloromethane DCM (200 mL) and extracted with water (100 mL), the aqueous phase was further extracted with dichloromethane DCM (100 mL), the combined organic phases were dried over anhydrous sodium sulfate, concentrated under reduced pressure to obtain a red solid N¹-(2-(dimethylamino)ethyl)-5-methoxy- N⁴-(4-(5-methoxy-1-methyl-1H-indole-3-yl)-1,3,5-triazin-2-yl)-N¹-methyl-2-nitrophenyl-1,4-diamine (1.00 g, 1.97 mmol, yield: 97.4%).

¹H NMR (CDCl₃, 400 MHz): δ 9.57 (s, 1H), 8.71 (s, 1H), 8.34 (s, 1H), 8.12 (d, J=2.4 Hz, 1H), 7.53 (s, 1H), 7.28 (s, 1H), 6.96 (dd, J1=2.8 Hz, J2=8.8 Hz, 1H), 6.67 (s, 1H), 3.98 (s, 3H), 3.93 (s, 3H), 3.90 (s, 3H), 3.31 (t, J=2.8 Hz, 2H), 2.91 (s, 3H), 2.57 (t, J=2.8 Hz, 2H), 2.26 (s, 6H).

e. Synthesis of N¹-(2-(dimethylamino)ethyl)-5-methoxy-N⁴-(4-(5-methoxy-1-methyl-1H-indol-3-yl)-1,3,5-triazin-2-yl)-N¹-methylphenyl-1,2,4-triamine f. Synthesis of N-(2-((2-(dimethylamino)ethyl)(methyl)amino)-4-methoxy-5-((4-(5-methoxy-1-methyl-1H-indol-3-v 1)-1,3,5-triazin-2-yl)amino)phenyl)acrylamide

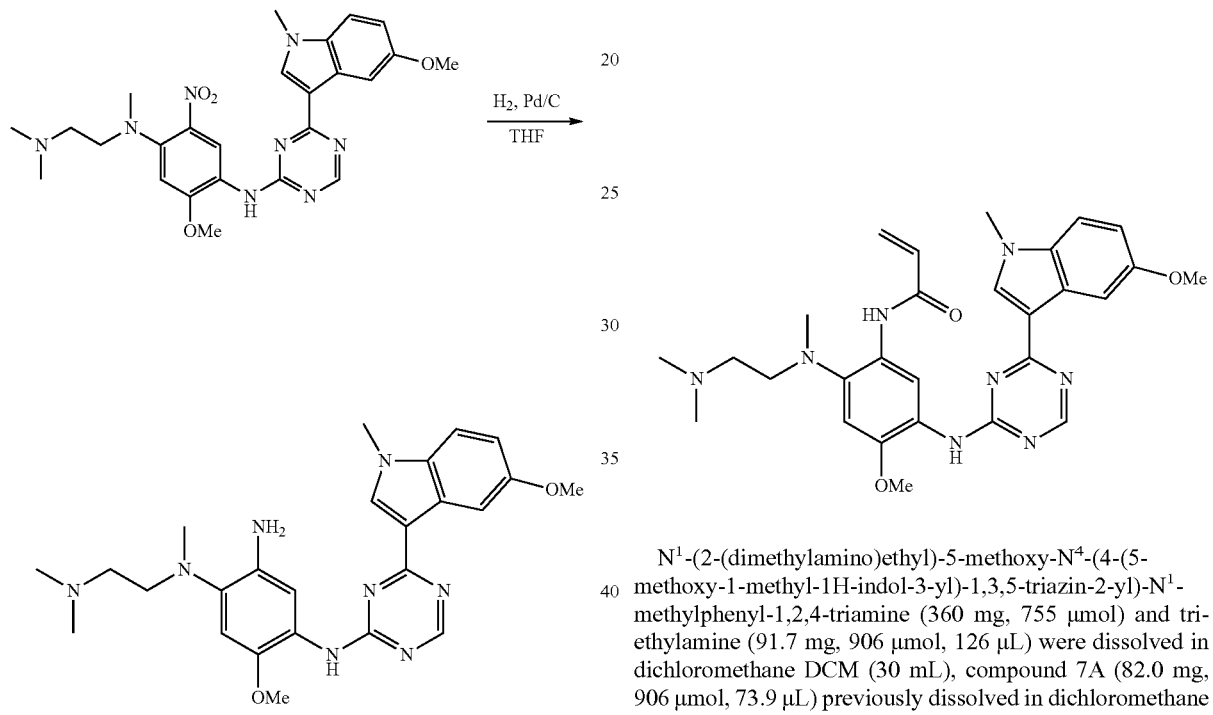

N¹-(2-(dimethylamino)ethyl)-5-methoxy-N⁴-(4-(5-methoxy-1-methyl-1H-indol-3-yl)-1,3,5-triazin-2-yl)-N¹-methyl-2-nitrophenyl-1,4-diamine (500 mg, 987 μmol) was dissolved in THF (30 mL) and Pd/C (0.1 g, 10% purity) was added, the reaction solution was stirred at 20° C. under hydrogen (16 psi) for 16 hours, LCMS showed the reaction was complete. The reaction mixture was filtered through celite, and the filter cake was washed with THF (50 mL). The resulting filtrate was concentrated under reduced pressure and subjected to silica gel column chromatography (DCM:MeOH:NH₄OH=10:1:0.1) to obtain a brown solid N¹-(2-(dimethylamino)ethyl)-5-methoxy-N⁴-(4-(5-methoxy-1-methyl-1H-indol-3-yl)-1,3,5-triazin-2-yl)-N¹-methylphenyl-1,2,4-triamine (360 mg, 755 μmol yield: 76.5%).

¹H NMR (CDCl₃, 400 MHz): δ 8.62 (s, 1H), 8.20 (s, 1H), 8.10 (s, 1H), 8.06 (s, 1H), 7.64 (s, 1H), 7.28 (s, 2H), 6.97 (dd, J1=2.4 Hz, J2=8.8 Hz, 1H), 6.72 (s, 1H), 3.90 (s, 3H), 3.86 (s, 3H), 3.85 (s, 3H), 2.98 (t, J=6.4 Hz, 2H), 2.66 (s, 3H), 2.43 (t, J=6.8 Hz, 2H), 2.28 (s, 6H).

N¹-(2-(dimethylamino)ethyl)-5-methoxy-N⁴-(4-(5-methoxy-1-methyl-1H-indol-3-yl)-1,3,5-triazin-2-yl)-N¹-methylphenyl-1,2,4-triamine (360 mg, 755 μmol) and triethylamine (91.7 mg, 906 μmol, 126 μL) were dissolved in dichloromethane DCM (30 mL), compound 7A (82.0 mg, 906 μmol, 73.9 μL) previously dissolved in dichloromethane DCM (5 mL) was added to the reaction mixture, and the reaction solution was stirred at 20° C. for 3 hours. LCMS showed that the reaction was complete. The reaction mixture was added with dichloromethane DCM (30 mL) and extracted with water (30 mL). The resulting aqueous phase was extracted with dichloromethane DCM (20 mL) again. The combined organic phases were dried over anhydrous sodium sulfate, concentrated under reduced pressure, subjected to silica gel column chromatography (DCM:MeOH=10:1) to obtain a yellow solid N-(2-((2-(dimethylamino)ethyl)(methyl)amino)-4-methoxy-5-((4-(5-methoxy-1-methyl-1H-indol-3-yl)-1,3,5-triazin-2-yl)amino)phenyl)acrylamide (220 mg, 414 μmol, yield: 54.8%).

¹H NMR (CDCl₃, 400 MHz): δ 10.0 (s, 1H), 9.94 (s, 1H), 9.35 (s, 1H), 8.70 (s, 1H), 8.14 (d, J=2.4 Hz, 1H), 7.77 (s, 1H), 7.27 (s, 3H), 6.92 (dd, J1=2.4 Hz, J2=8.8 Hz, 1H), 6.78 (s, 1H), 6.49-6.45 (m, 2H), 5.74-5.69 (m, 1H), 3.96 (s, 3H), 3.95 (s, 3H), 3.89 (s, 3H), 2.96 (s, 2H), 2.71 (s, 3H), 2.43 (s, 2H), 2.35 (s, 6H).

ESI-MS (m/z): [M+H]⁺ 531.3.

Example 9: Synthesis of N-(5-((4-(5-chloro-1-methyl-1H-indol-3-yl)-1,3,5-triazin-2-yl)amino)-2-((2-(dimethylamino)ethyl(m ethyl)amino)-4-methoxyphenyl)acrylamide (Compound 9)

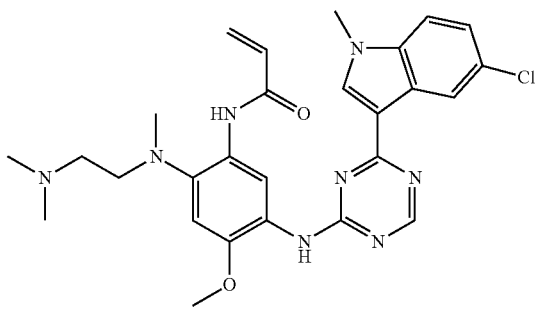 [SMILES: C=CC(=O)Nc1cc(Nc2ncnc(-c3cn(C)c4ccc(Cl)cc34)n2)c(OC)cc1N(C)CCN(C)C]

a. Synthesis of 5-chloro-1-methyl-1H-indole

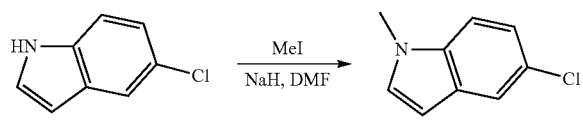

NaH (3.17 g, 79.5 mmol, 60% purity) was added to DMF (200 mL), 5-chloro-indole (10.0 g, 65.9 mmol) was added at 0° C., and stirred at this temperature for 20 minutes, and methyl iodide (11.2 g, 79.2 mmol, 4.93 mL) dissolved in DMF (20 mL) was added. After the reaction was stirred at 0-20° C. for 2 hours, LCMS showed that the reaction was complete. The reaction mixture was poured into water (500 mL), the filtered solid was dissolved in acetic ether (300 mL), dried over anhydrous sodium sulfate, and concentrated under reduced pressure. The crude product was purified by silica gel column chromatography (petroleum ether:acetic ether=10:1) to obtain a pale yellow liquid 5-chloro-1-methyl-1H-indole (10.7 g, 64.6 mmol, yield: 97.9%).

$^1$H NMR (CDCl$_3$, 400 MHz): δ 7.58 (d, J=2.0 Hz, 1H), 7.24-7.22 (m, 1H), 7.18-7.15 (m, 1H), 7.06 (d, J=3.2 Hz, 1H), 6.42 (d, J=2.8 Hz, 1H), 3.78 (s, 3H).

b. Synthesis of 5-chloro-3-(4-chloro-1,3,5-triazin-2-yl)-1-methyl-1H-indole

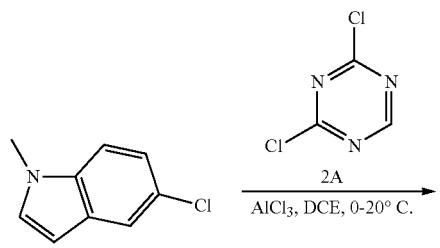

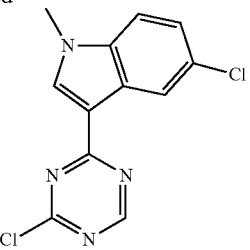

After dissolving compound 2A (9.96 g, 66.4 mmol) in dichloroethane DCE (200 mL), AlCl$_3$ (9.66 g, 72.5 mmol) was added at 0° C. The reaction solution was stirred at this temperature for 40 minutes and 5-chloro-1-methyl-1H-indole (10.0 g, 60.4 mmol) dissolved in dichloroethane DCE (40 mL) was added to the reaction mixture in portions within 40 minutes and stirred at 0-20° C. at 3 hours, LCMS showed the reaction was complete. The reaction mixture was poured into ice water (400 mL) and filtered. The obtained solid was dissolved in dichloromethane DCM (400 mL), dried over anhydrous sodium sulfate, concentrated under reduced pressure and subjected to silica gel column chromatography (petroleum ether:acetic ether=2:1) to obtain a yellow solid 5-chloro-3-(4-chloro-1,3,5-triazin-2-yl)-1-methyl-1H-indole (990 mg, 3.55 mmol, yield: 5.87%).

$^1$H NMR (CDCl$_3$, 400 MHz): δ 8.84 (s, 1H), 8.56 (s, 1H), 8.25 (s, 1H), 7.33 (s, 1H), 7.30 (s, 1H), 3.89 (s, 3H).

c. Synthesis of 4-(5-chloro-1-methyl-1H-indol-3-yl)-N-(4-fluoro-2-methoxy-5-nitrophenyl)-1,3,5-triazin-2-amine

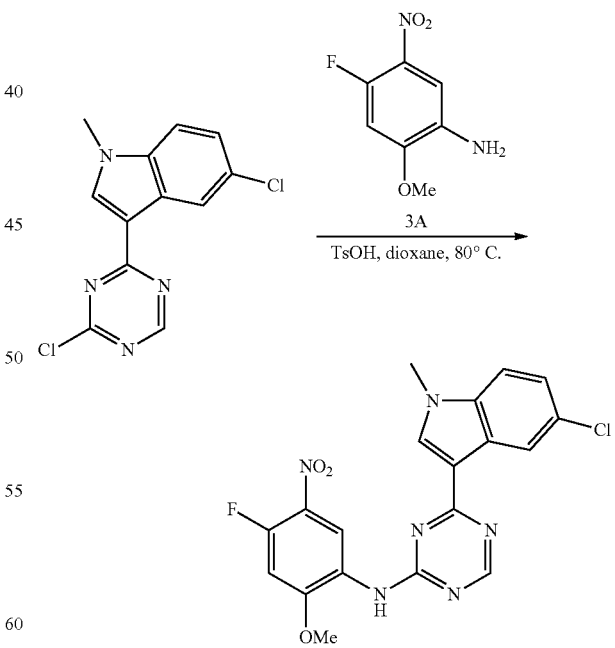

To a solution of 5-chloro-3-(4-chloro-1,3,5-triazin-2-yl)-1-methyl-1H-indole (990 mg, 3.55 mmol) and compound 3A (792 mg, 4.26 mmol) in 2,4-dioxane (50 mL), TsOH (794 mg, 4.61 mmol) was added, the reaction solution was stirred at 80° C. for 4 hours, LCMS showed the reaction was complete. The reaction mixture was poured into ice water (200 mL), the solid was filtered, washed with water (50 mL), and concentrated under reduced pressure to obtain a brown solid 4-(5-chloro-1-methyl-1H-indol-3-yl)-N-(4-fluoro-2-methoxy-5-nitrophenyl)-1,3,5-triazin-2-amine (1.50 g, 3.50 mmol, yield: 98.6%).

d. Synthesis of $N^1$-4-(5-chloro-1-methyl-1H-indol-3-yl)-1,3,5-triazin-2-yl)-$N^4$-(2-(dimethylamino)ethyl)-2-methoxy-$N^4$-methyl-5-nitrophenyl-1,4-diamine

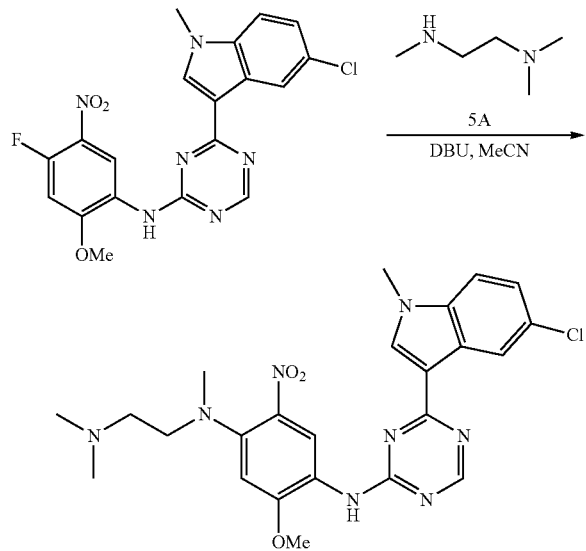

4-(5-chloro-1-methyl-1H-indol-3-yl)-N-(4-fluoro-2-methoxy-5-nitrophenyl)-1,3,5-triazin-2-amine (1.50 g, 3.50 mmol) was dissolved in acetonitrile ACN (30 mL), compound 5A (715 mg, 7.00 mmol, 909 μL) and DBU (1.07 g, 7.00 mmol, 1.05 mL) were added, and the reaction mixture was stirred at 80° C. for 5 hours, LCMS showed that the reaction was complete. After concentration under reduced pressure, it was dissolved in dichloromethane DCM (300 mL) and extracted with water (100 mL).

The aqueous phase was further extracted with dichloromethane DCM (100 mL). The organic phases were combined and dried over anhydrous sodium sulfate, concentrated under reduced pressure to obtain crude red solid $N^1$-4-(5-chloro-1-methyl-1H-indol-3-yl)-1,3,5-triazin-2-yl)-$N^4$-(2-(dimethylamino)ethyl)-2-methoxy-$N^4$-methyl-5-nitrophenyl-1,4-diamine (1.80 g).

e. Synthesis of $N^4$-(4-(5-chloro-1-methyl-1H-indol-3-yl)-1,3,5-triazin-2-yl)-$N^1$-(2-(dimethylamino)ethyl)-5-methoxy-$N^1$-methylphenyl-1,2,4-triamine

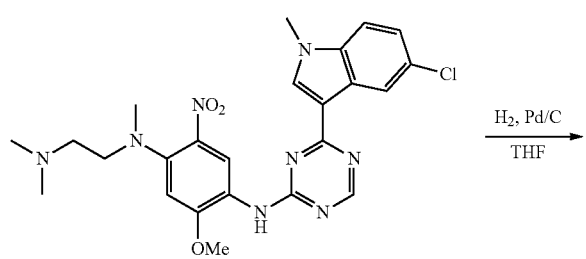

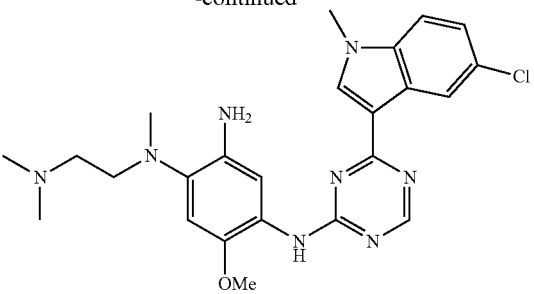

$N^1$-4-(5-chloro-1-methyl-1H-indol-3-yl)-1,3,5-triazin-2-yl)-$N^4$-(2-(dimethylamino)ethyl)-2-methoxy-$N^4$-methyl-5-nitrophenyl-1,4-diamine (1 g, 1.96 mmol) was dissolved in THF (30 mL) and Pd/C (0.2 g, purity is 10%) was added, the reaction solution was stirred at 20° C. under hydrogen (16 psi) for 16 hours, LCMS showed the reaction was complete. The reaction mixture was filtered through celite, and the filter cake was washed with THF (50 mL). The resulting filtrate was concentrated under reduced pressure and subjected to silica gel column chromatography (DCM:MeOH:NH$_4$OH=10:1:0.1) to obtain a brown solid $N^4$-(4-(5-chloro-1-methyl-TH-indol-3-yl)-1,3,5-triazin-2-yl)-$N^1$-(2-(dimethylamino)ethyl)-5-methoxy-$N^1$-methylphenyl-1,2,4-triamine (570 mg, 1.19 mmol yield: 60.5%).

$^1$H NMR (CDCl$_3$, 400 MHz): δ 8.62 (s, 2H), 8.14 (s, 1H), 7.95 (s, 1H), 7.67 (s, 1H), 7.27-7.26 (m, 3H), 6.73 (s, 1H), 3.86 (s, 3H), 3.85 (s, 3H), 2.98 (t, J=6.8 Hz, 2H), 2.69 (s, 3H), 2.43 (t, J=6.8 Hz, 2H), 2.27 (s, 6H).

f. Synthesis of N-(5-((4-(5-chloro-1-methyl-TH-indol-3-yl)-1,3,5-triazin-2-yl)amino)-2-((2-(dimethylamino)ethyl(m ethyl)amino)-4-methoxyphenyl) acrylamide

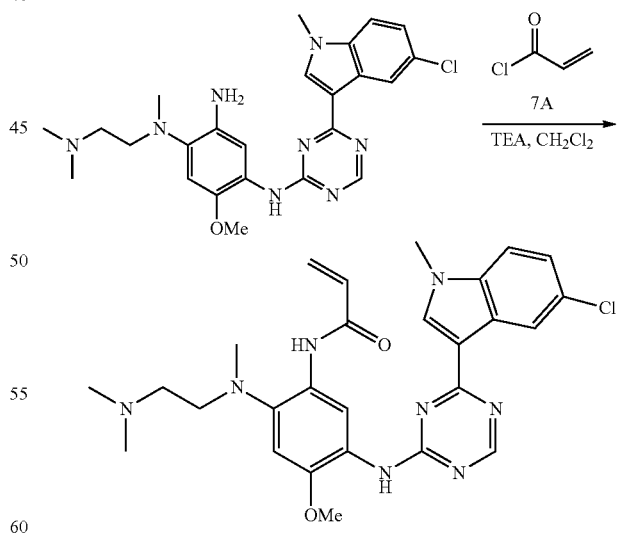

$N^4$-(4-(5-chloro-1-methyl-TH-indol-3-yl)-1,3,5-triazin-2-yl)-$N^1$-(2-(dimethylamino)ethyl)-5-methoxy-$N^1$-methylphenyl-1,2,4-triamine (570 mg, 1.19 mmol) and triethylamine (144 mg, 1.42 mmol, 197.9 μL) were dissolved in dichloromethane DCM (30 mL). Compound 7A (128.0 mg, 1.42 mmol, 116 μL) previously dissolved in dichloromethane DCM (5 mL) was added to the reaction mixture. The reaction mixture was stirred at 20° C. for 3 hours. LCMS showed the reaction was complete. The reaction mixture was added with dichloromethane DCM (30 mL) and extracted with water (30 mL). The resulting aqueous phase was extracted with dichloromethane DCM (20 mL) again. The organic phases were combined and dried over anhydrous sodium sulfate, concentrated under reduced pressure and subjected to silica gel column chromatography (DCM: MeOH=10:1) to obtain a yellow solid N-(5-((4-(5-chloro-1-methyl-1H-indol-3-yl)-1,3,5-triazin-2-yl)amino)-2-((2-(dimethylamino)ethyl(m ethyl)amino)-4-methoxyphenyl) acrylamide (340 mg, 635 μmol, yield: 53.0%).

$^1$H NMR (CDCl$_3$, 400 MHz): δ 10.20 (s, 1H), 9.92 (s, 1H), 9.42 (s, 1H), 8.70 (s, 1H), 8.62 (d, J=1.6 Hz, 1H), 7.80 (s, 1H), 7.29-7.22 (m, 2H), 6.81 (s, 1H), 6.48-6.44 (m, 2H), 5.74-6.71 (m, 1H), 3.98 (s, 3H), 3.89 (s, 3H), 2.90 (s, 2H), 2.71 (s, 3H), 2.27 (m, 8H).

ESI-MS (m/z): [M+H]$^+$ 535.1.

Example 10

Synthesis of N-(5-((4-(6-chloro-5-methoxy-1-methyl-1H-indol-3-yl)-1,3,5-triazin-2-yl)amino)-2-((2-(dimethylamino)ethyl(methyl)amino)-4-methoxyphenyl)acrylamide (Compound 10)

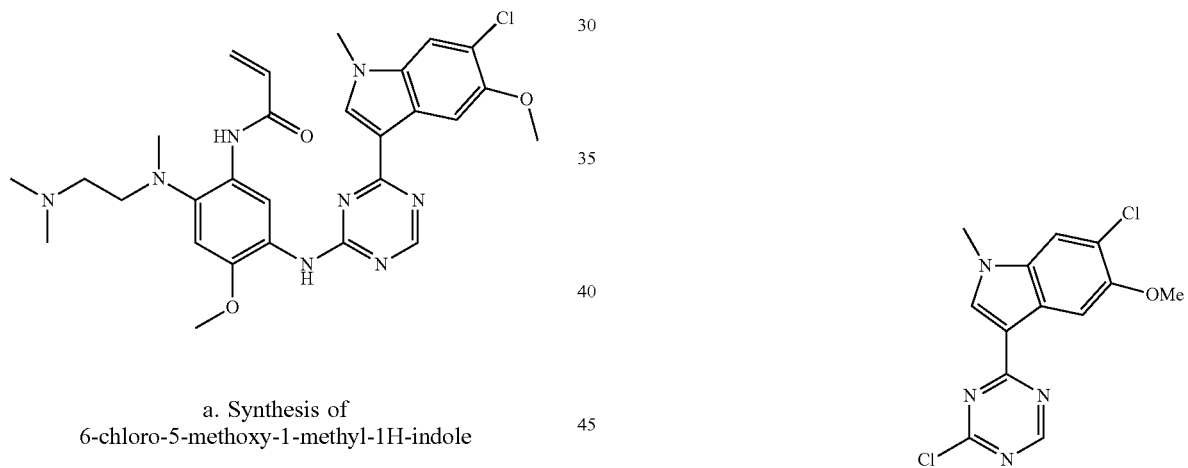

a. Synthesis of 6-chloro-5-methoxy-1-methyl-1H-indole

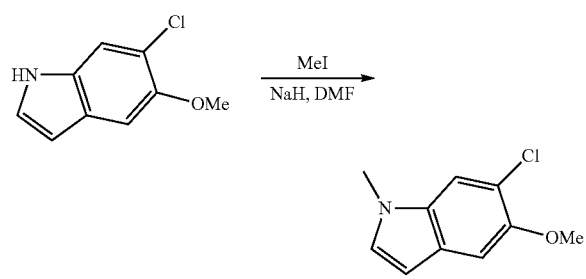

NaH (1.32 g, 33.0 mmol, 60% purity) was added to THF (100 mL), 6-chloro-5-methoxyindole (5.0 g, 27.5 mmol) was added at 0° C., and stirred at this temperature for 20 minutes, and methyl iodide (4.69 g, 33.0 mmol, 2.06 mL) dissolved in THF (5 mL) was added. After the reaction solution was stirred at 0-20° C. for 2 hours, LCMS showed that the reaction was complete. The reaction mixture was poured into water (500 mL), the filtered solid was dissolved in acetic ether (300 mL), dried over anhydrous sodium sulfate, and concentrated under reduced pressure. The crude product was purified by silica gel column chromatography (petroleum ether:acetic ether=10:1) to obtain a white solid 6-chloro-5-methoxy-1-methyl-1H-indole (4.8 g, 24.5 mmol, yield: 89.1%).

$^1$H NMR (CDCl$_3$, 400 MHz): δ 7.34 (s, 1H), 7.13 (s, 1H), 7.01 (d, J=3.2 Hz, 1H), 6.39 (d, J=2.0 Hz, 1H), 3.92 (s, 3H), 3.71 (s, 3H).

b. Synthesis of 6-chloro-3-(4-chloro-1,3,5-triazin-2-yl)-5-methoxy-1-methyl-1H-indole

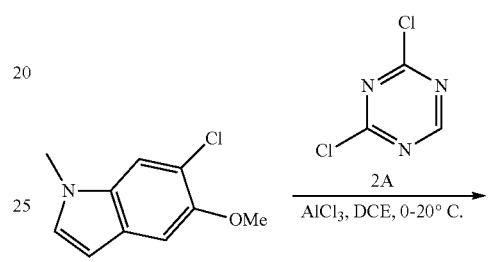

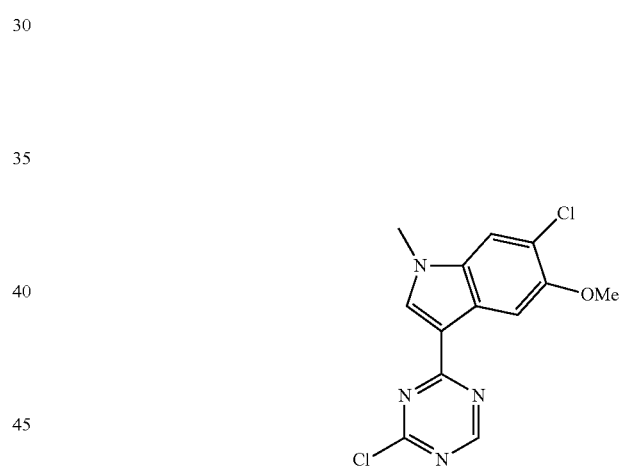

After dissolving compound 2A (2.95 g, 19.7 mmol) in dichloroethane DCE (200 mL), AlCl$_3$ (2.62 g, 19.7 mmol) was added at 0° C., the reaction solution was stirred at this temperature for 40 minutes, and 6-chloro-5-methoxy-1-methyl-1H-indole (3.5 g, 17.9 mmol) dissolved in dichloroethane DCE (40 mL) was added to the reaction mixture in portions within 40 minutes, and stirred at 0-20° C. for 16 hours, LCMS showed that the reaction was complete. The reaction mixture was poured into ice water (200 mL) and filtered. The resulting solid was dissolved in dichloromethane DCM (200 mL), dried over anhydrous sodium sulfate, concentrated under reduced pressure and subjected to silica gel column chromatography (petroleum ether:acetic ether=2:1) to obtain a yellow solid 6-chloro-3-(4-chloro-1,3,5-triazin-2-yl)-5-methoxy-1-methyl-1H-indole (410 mg, 1.33 mmol, yield: 7.41%).

$^1$H NMR (CDCl$_3$, 400 MHz): δ 8.83 (s, 1H), 8.20 (s, 1H), 8.12 (s, 1H), 7.42 (s, 1H), 4.03 (s, 3H), 3.85 (s, 3H).

c. Synthesis of 4-(6-chloro-5-methoxy-1-methyl-1H-indol-3-yl)-N-(4-fluoro-2-methoxy-5-nitrophenyl)-1,3,5-triazin-2-amine

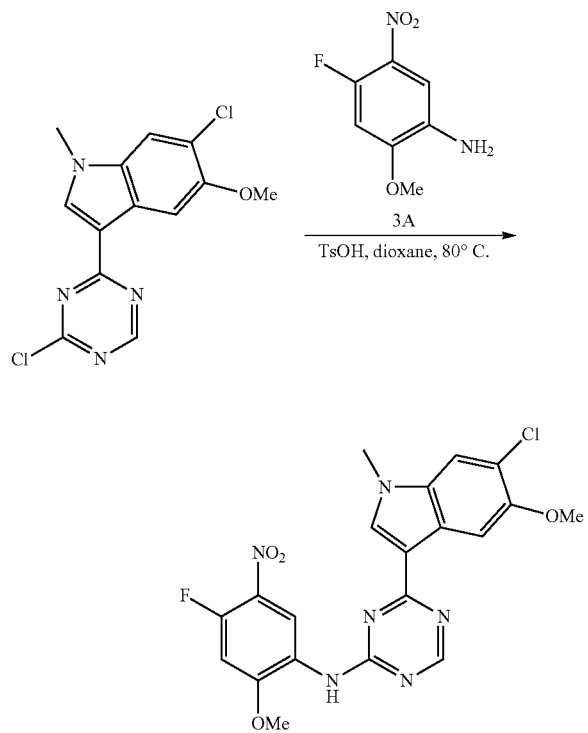

To a solution of 6-Chloro-3-(4-chloro-1,3,5-triazin-2-yl)-5-methoxy-1-methyl-1H-indole (410 mg, 1.33 mmol) and compound 3A (296 mg, 1.59 mmol) in 2,4-dioxane (30 mL), TsOH (297 mg, 1.72 mmol) was added, and the reaction solution was stirred at 80° C. for 4 hours. LCMS showed that the reaction was complete. The reaction mixture was poured into ice water (200 mL), the solid was filtered, washed with water (50 mL), and concentrated under reduced pressure to obtain a brown solid 4-(6-chloro-5-methoxy-1-methyl-1H-indol-3-yl)-N-(4-fluoro-2-methoxy-5-nitrophenyl)-1,3,5-triazin-2-amine (560 mg, 1.22 mmol, yield: 92.0%).

d. Synthesis of N$^1$-(4-(6-chloro-5-methoxy-1-methyl-1H-indol-3-yl)-1,3,5-triazin-2-yl)-N$^4$-(2-(dimethylamino)ethyl)-2-methoxy-N$^4$-methyl-5-nitrophenyl-1,4-diamine

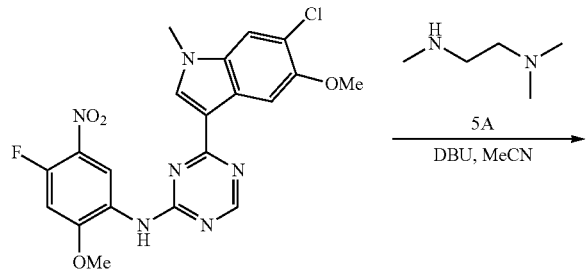

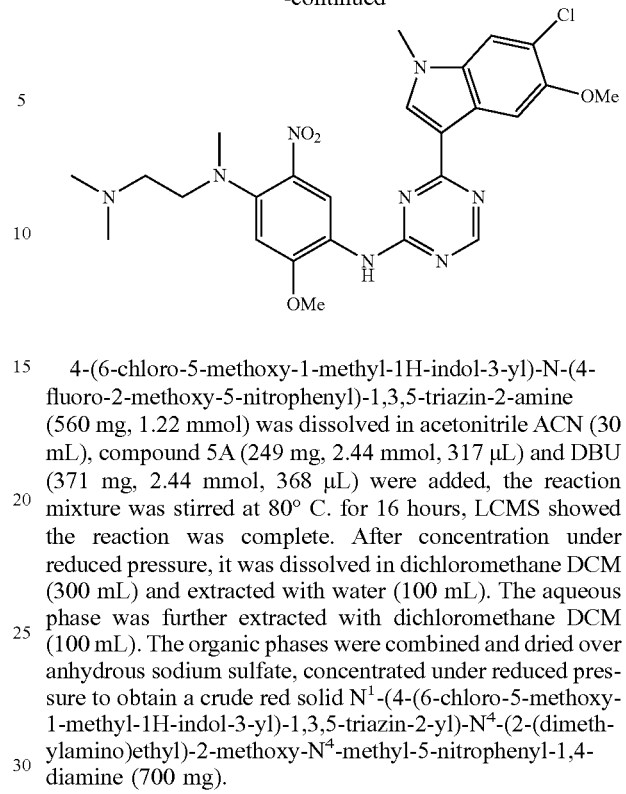

4-(6-chloro-5-methoxy-1-methyl-1H-indol-3-yl)-N-(4-fluoro-2-methoxy-5-nitrophenyl)-1,3,5-triazin-2-amine (560 mg, 1.22 mmol) was dissolved in acetonitrile ACN (30 mL), compound 5A (249 mg, 2.44 mmol, 317 μL) and DBU (371 mg, 2.44 mmol, 368 μL) were added, the reaction mixture was stirred at 80° C. for 16 hours, LCMS showed the reaction was complete. After concentration under reduced pressure, it was dissolved in dichloromethane DCM (300 mL) and extracted with water (100 mL). The aqueous phase was further extracted with dichloromethane DCM (100 mL). The organic phases were combined and dried over anhydrous sodium sulfate, concentrated under reduced pressure to obtain a crude red solid N$^1$-(4-(6-chloro-5-methoxy-1-methyl-1H-indol-3-yl)-1,3,5-triazin-2-yl)-N$^4$-(2-(dimethylamino)ethyl)-2-methoxy-N$^4$-methyl-5-nitrophenyl-1,4-diamine (700 mg).

e. Synthesis of N$^4$-(4-(6-chloro-5-methoxy-1-methyl-1H-indol-3-yl)-1,3,5-triazin-2-yl)-N$^1$-(2-(dimethylamino)ethyl)-5-methoxy-N$^1$-methylphenyl-1,2,4-triamine

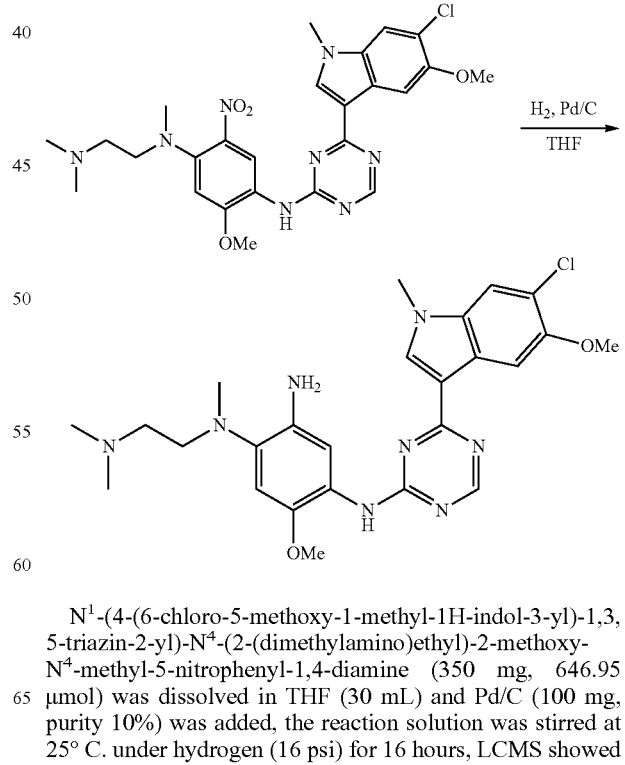

N$^1$-(4-(6-chloro-5-methoxy-1-methyl-1H-indol-3-yl)-1,3,5-triazin-2-yl)-N$^4$-(2-(dimethylamino)ethyl)-2-methoxy-N$^4$-methyl-5-nitrophenyl-1,4-diamine (350 mg, 646.95 μmol) was dissolved in THF (30 mL) and Pd/C (100 mg, purity 10%) was added, the reaction solution was stirred at 25° C. under hydrogen (16 psi) for 16 hours, LCMS showed the reaction was complete. The reaction mixture was filtered through celite, and the filter cake was washed with THF (50 mL). The resulting filtrate was concentrated under reduced pressure and subjected to silica gel column chromatography (DCM:MeOH:NH$_4$OH=10:1:0.1) to obtain a brown solid N$^4$-(4-(6-chloro-5-methoxy-1-methyl-1H-indol-3-yl)-1,3,5-triazin-2-yl)-N$^1$-(2-(dimethylamino)ethyl)-5-methoxy-N$^1$-methylphenyl-1,2,4-triamine (260 mg, 508 μmol yield: 78.6%).

f. Synthesis of N-(5-((4-(6-chloro-5-methoxy-1-methyl-TH-indol-3-yl)-1,3,5-triazin-2-yl)amino)-2-((2-(dimethylamino)ethyl(methyl)amino)-4-methoxyphenyl)acrylamide

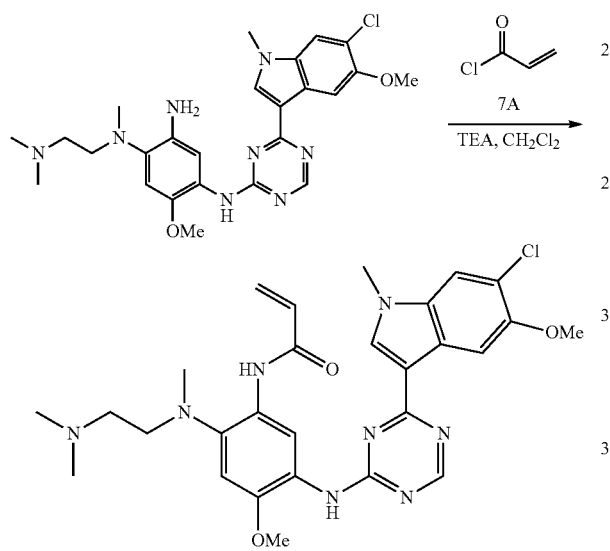

N$^4$-(4-(6-chloro-5-methoxy-1-methyl-TH-indol-3-yl)-1,3,5-triazin-2-yl)-N$^1$-(2-(dimethylamino)ethyl)-5-methoxy-N$^1$-methylphenyl-1,2,4-triamine (260 mg, 508 μmol) and triethylamine (61.8 mg, 610 μmol, 85 μL) were dissolved in dichloromethane DCM (30 mL), compound 7A (55.3 mg, 610 μmol, 85.0 μL) dissolved in dichloromethane DCM (5 mL) was added to the reaction mixture, and the reaction solution was stirred at 20° C. for 3 hours, LCMS showed the reaction was complete. The reaction mixture was added with dichloromethane DCM (30 mL) and extracted with water (30 mL). The resulting aqueous phase was extracted with dichloromethane DCM (20 mL) again. The organic phases were combined and dried over anhydrous sodium sulfate, concentrated under reduced pressure, and subjected to silica gel column chromatography (DCM:MeOH=10:1) to obtain a yellow solid N-(5-((4-(6-chloro-5-methoxy-1-methyl-1H-indol-3-yl)-1,3,5-triazin-2-yl)amino)-2-((2-(dimethylamino)ethyl(methyl)amino)-4-methoxyphenyl)acrylamide (160 mg, 283 μmol, yield: 55.6%).

$^1$H NMR (CDCl$_3$, 400 MHz): δ 10.25 (s, 1H), 9.95 (s, 1H), 9.40 (s, 1H), 8.71 (s, 1H), 8.20 (s, 1H), 7.80 (s, 1H), 7.40 (s, 1H), 6.80 (s, 1H), 6.49-6.37 (m, 2H), 5.75-5.72 (m, 1H), 4.04 (s, 3H), 3.95 (s, 3H), 3.89 (s, 3H), 2.88 (s, 2H), 2.72 (s, 3H), 2.27 (s, 8H).

ESI-MS (m/z): [M+H]$^+$ 565.1.

Example 11

Synthesis of N-(2-((2-(dimethylamino)ethyl(methyl)amino)-5-((4-(5-fluoro-1-methyl-1H-indol-3-yl)-1,3,5-triazin-2-yl)amino)-4-methoxyphenyl)acrylamide (Compound 11)

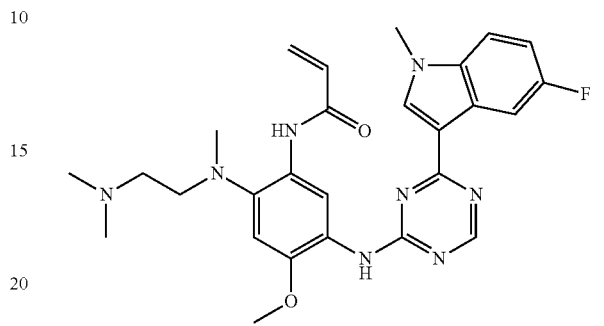

a. Synthesis of 5-fluoro-1-methyl-1H-indole

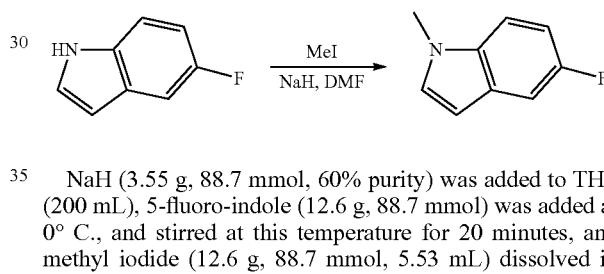

NaH (3.55 g, 88.7 mmol, 60% purity) was added to THF (200 mL), 5-fluoro-indole (12.6 g, 88.7 mmol) was added at 0° C., and stirred at this temperature for 20 minutes, and methyl iodide (12.6 g, 88.7 mmol, 5.53 mL) dissolved in THF (20 mL) was added. After the reaction was stirred at 0-20° C. for 2 hours, LCMS showed that the reaction was complete. The reaction mixture was poured into water (500 mL), the filtered solid was dissolved in acetic ether (300 mL), dried over anhydrous sodium sulfate, and concentrated under reduced pressure. The crude product was purified by silica gel column chromatography (petroleum ether:acetic ether=10:1) to obtain a brown solid 5-fluoro-1-methyl-1H-indole (11.0 g, 73.7 mmol, yield: 90.6%).

$^1$H NMR (CDCl$_3$, 400 MHz): δ 7.29-7.26 (m, 1H), 7.22-7.21 (m, 1H), 7.09 (d, J=2.8 Hz, 1H), 6.98-6.97 (m, 1H), 6.44 (d, J=2.4 Hz, 1H), 3.79 (s, 3H).

b. Synthesis of 3-(4-chloro-1,3,5-triazin-2-yl)-5-fluoro-1-methyl-1H-indole

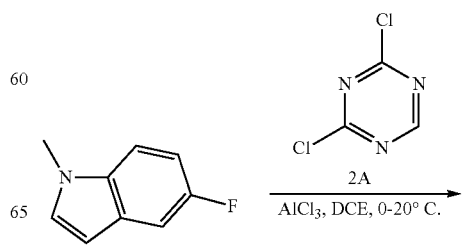

-continued

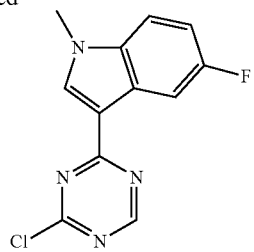

After dissolving compound 2A (5.03 g, 33.5 mmol) in dichloroethane DCE (200 mL), AlCl₃ (4.92 g, 36.8 mmol) was added at 0° C. The reaction solution was stirred at this temperature for 40 minutes and 5-fluoro-1-methyl-1H-indole (5.0 g, 33.5 mmol) dissolved in difluoroethane DCE (40 mL) was added to the reaction mixture in portions within 40 minutes and stirred at 0-20° C. for 3 hours, LCMS showed the reaction was complete. The reaction mixture was poured into ice water (500 mL) and filtered. The resulting solid was dissolved in dichloromethane DCM (500 mL), dried over anhydrous sodium sulfate, concentrated under reduced pressure and subjected to silica gel column chromatography (petroleum ether:acetic ether=2:1) to obtain a light red solid 3-(4-chloro-1,3,5-triazin-2-yl)-5-fluoro-1-methyl-1H-indole (790 mg, 2.62 mmol, yield: 7.81%).

$^1$H NMR (CDCl₃, 400 MHz): δ 8.82 (s, 1H), 8.26-8.23 (m, 2H), 7.33-7.29 (m, 1H), 7.12-7.07 (m, 1H), 3.89 (s, 3H).

c. Synthesis of 4-(5-fluoro-1-methyl-1H-indol-3-yl)-N-(4-fluoro-2-methoxy-5-nitrophenyl)-1,3,5-triazin-2-amine

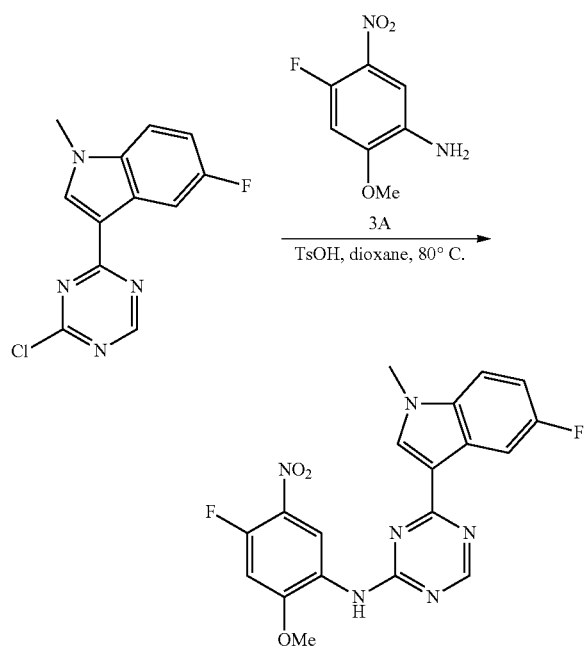

To a solution of 3-(4-chloro-1,3,5-triazin-2-yl)-5-fluoro-1-methyl-1H-indole (790 mg, 3.01 mmol) and compound 3A (672 mg, 3.61 mmol) in 2,4-dioxane (30 mL), TsOH (673 mg, 3.91 mmol) was added, and the reaction solution was stirred at 80° C. for 4 hours. LCMS showed that the reaction was complete. The reaction mixture was poured into ice water (200 mL), the solid was filtered, washed with water (50 mL), and concentrated under reduced pressure to obtain a brown solid 4-(5-fluoro-1-methyl-1H-indol-3-yl)-N-(4-fluoro-2-methoxy-5-nitrophenyl)-1,3,5-triazin-2-amine (1.20 g, 2.24 mmol, yield: 74.5%).

d. Synthesis of N$^1$-(2-(dimethylamino)ethyl)-N$^4$-(4-(5-fluoro-1-methyl-1H-indol-3-yl)-1,3,5-triazine-2-yl)-5-methoxy-N$^1$-methyl-2-nitrophenyl-1,4-diamine

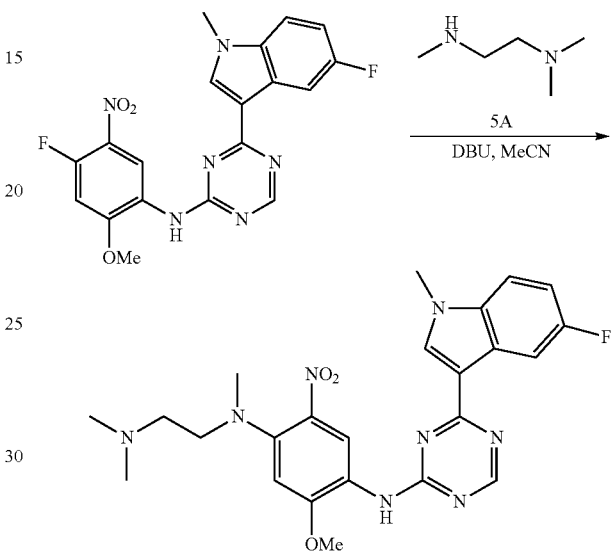

4-(5-fluoro-1-methyl-1H-indol-3-yl)-N-(4-fluoro-2-methoxy-5-nitrophenyl)-1,3,5-triazin-2-amine (1.2 g, 2.91 mmol) was dissolved in acetonitrile ACN (30 mL), compound 5A (595 mg, 5.82 mmol, 756 μL) and DBU (886 mg, 5.82 mmol, 877 μL) were added, and the reaction mixture was stirred at 80° C. for 16 hours, LCMS showed the reaction was complete. After concentration under reduced pressure, it was redissolved in dichloromethane DCM (300 mL) and extracted with water (100 mL). The aqueous phase was further extracted with dichloromethane DCM (100 mL). the organic phases were combined and dried over anhydrous sodium sulfate, concentrated under reduced pressure to obtain a crude red solid N$^1$-(2-(dimethylamino)ethyl)-N$^4$-(4-(5-fluoro-1-methyl-1H-indol-3-yl)-1,3,5-triazine-2-yl)-5-methoxy-N$^1$-methyl-2-nitrophenyl-1,4-diamine (1.5 g).

e. Synthesis of N$^1$-(2-(dimethylamino)ethyl)-N$^4$-(4-(5-fluoro-1-methyl-1H-indol-3-yl)-1,3,5-triazine-2-yl)-5-methoxy-N$^1$-methylphenyl-1,2,4-triamine

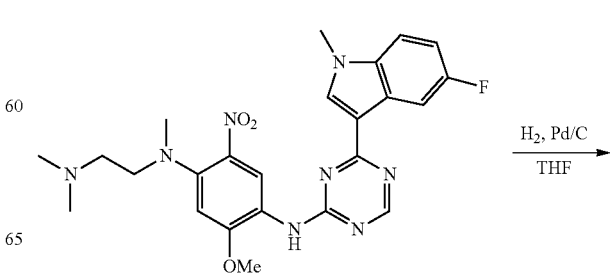

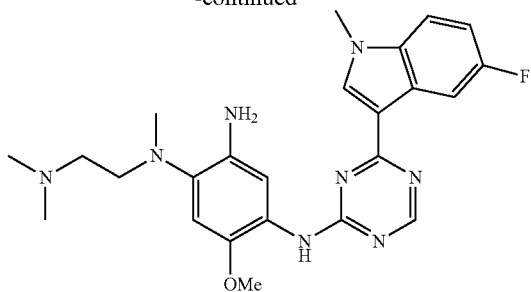

$N^1$-(2-(dimethylamino)ethyl)-$N^4$-(4-(5-fluoro-1-methyl-1H-indol-3-yl)-1,3,5-triazine-2-yl)-5-methoxy-$N^1$-methyl-2-nitrophenyl-1,4-diamine (800 mg, 1.62 mmol) was dissolved in THF (30 mL), and Pd/C (100 mg, purity is 10%) was added, the reaction solution was stirred at 25° C. under hydrogen (16 psi) for 16 hours, LCMS showed the reaction was complete. The reaction mixture was filtered through celite, and the filter cake was washed with THF (50 mL). The resulting filtrate was concentrated under reduced pressure and subjected to silica gel column chromatography (DCM:MeOH:NH$_4$OH=10:1:0.1) to obtain a brown solid $N^1$-(2-(dimethylamino)ethyl)-$N^4$-(4-(5-fluoro-1-methyl-1H-indol-3-yl)-1,3,5-triazine-2-yl)-5-methoxy-$N^1$-methylphenyl-1,2,4-triamine (550 mg, 1.18 mmol yield: 73.2%).

$^1$H NMR (CDCl$_3$, 400 MHz): δ 8.60 (s, 1H), 8.34 (dd, J1=2.8 Hz, J2=10.0 Hz, 1H), 8.15 (s, 1H), 7.97 (s, 1H), 7.64 (s, 1H), 7.30-7.26 (m, 2H), 6.07-7.04 (m, 1H), 6.72 (s, 1H), 3.87 (s, 3H), 3.85 (s, 3H), 3.00 (t, J=6.8 Hz, 2H), 2.69 (s, 3H), 2.46 (t, J=6.8 Hz, 2H), 2.27 (s, 6H).

f. Synthesis of N-(2-((2-(dimethylamino)ethyl (methyl)amino)-5-((4-(5-fluoro-1-methyl-1H-indol-3-yl)-1,3,5-triazin-2-yl)amino)-4-methoxyphenyl) acrylamide

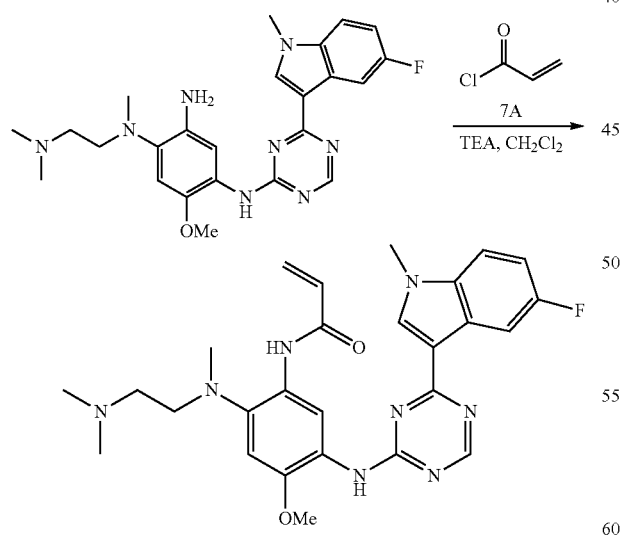

$N^1$-(2-(dimethylamino)ethyl)-$N^4$-(4-(5-fluoro-1-methyl-1H-indol-3-yl)-1,3,5-triazine-2-yl)-5-methoxy-$N^1$-methylphenyl-1,2,4-triamine (500 mg, 1.08 mmol) and triethylamine (131 mg, 1.30 mmol, 180 μL) were dissolved in dichloromethane DCM (30 mL), compound 7A (117 mg, 1.30 mmol, 105.0 μL) previously dissolved in dichloromethane DCM (5 mL) was added to the reaction mixture, the reaction solution was stirred at 20° C. for 3 hours, LCMS showed the reaction was complete. The reaction mixture was added with dichloromethane DCM (50 mL) and extracted with water (30 mL). The resulting aqueous phase was further extracted with dichloromethane DCM (20 mL). The organic phases were combined and dried over anhydrous sodium sulfate, concentrated under reduced pressure, and subjected to silica gel column chromatography (DCM:MeOH=10:1) to obtain a brown solid N-(2-((2-(dimethylamino)ethyl (methyl)amino)-5-((4-(5-fluoro-1-methyl-1H-indol-3-yl)-1, 3,5-triazin-2-yl)amino)-4-methoxyphenyl)acrylamide (380 mg, 732 μmol, yield: 67.8%).

$^1$H NMR (CDCl$_3$, 400 MHz): δ 10.22 (s, 1H), 9.91 (s, 1H), 9.39 (s, 1H), 8.69 (s, 1H), 8.30 (dd, J1=2.4 Hz, J2=10.0 Hz, 1H), 7.78 (s, 3H), 7.29-7.26 (s, 1H), 7.04-6.99 (m, 1H), 6.81 (s, 1H), 6.48-6.37 (m, 2H), 5.73-5.70 (m, 1H), 3.98 (s, 3H), 3.89 (s, 3H), 2.89 (s, 2H), 2.72 (s, 3H), 2.27 (s, 8H).

ESI-MS (m/z): [M+H]$^+$ 519.5.

Example 12

Synthesis of N-(5-((4-(4-chloro-3-methoxyphenoxy)-1,3,5-triazin-2-yl)amino)-2-((2-(dimethylamino)ethyl(methyl)amino)-4-methoxyphenyl)acrylamide (Compound 12)

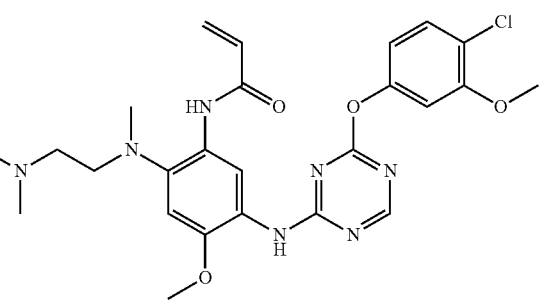

a. Synthesis of 2-chloro-4-(4-chloro-3-methoxyphenolyl)-1,3,5-triazine

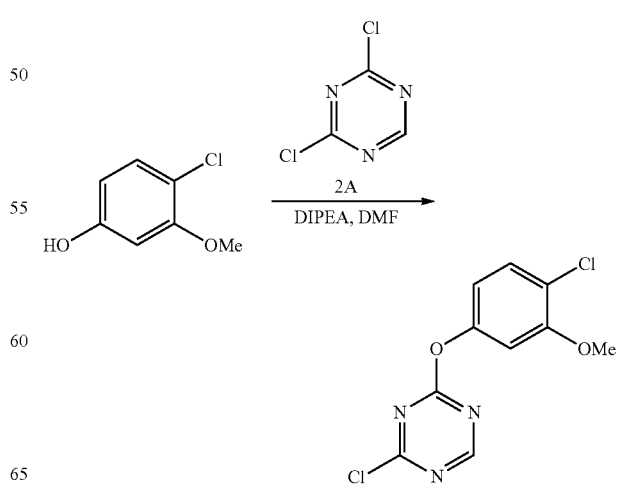

After dissolving compound 2A (3.12 g, 20.8 mmol) in THF (30.0 mL), DIPEA (3.67 g, 28.4 mmol, 4.94 mL) and 4-chloro-3-methoxyphenol (3.00 g, 18.9 mmol) were added and the reaction mixture was stirred at 15° C. for 16 hours, LCMS showed the reaction was complete. The reaction mixture was poured into acetic ether (50.0 mL) and water (100 mL×2) for extraction, the organic phases were combined and dried over anhydrous sodium sulfate, dried under reduced pressure, and the reaction mixture was titrated with acetic ether (50.0 mL) and filtered to obtain a white solid 2-chloro-4-(4-chloro-3-methoxyphenolyl)-1,3,5-triazine (2.70 g, 9.92 mmol, yield: 52.5%).

$^1$H NMR (DMSO-d6, 400 MHz): δ 9.01 (s, 1H), 7.54 (d, J=8.8 Hz, 1H), 7.23 (d, J=2.4 Hz, 1H), 6.95-6.88 (m, 1H), 3.83 (s, 3H).

b. Synthesis of 4-(4-chloro-3-methoxyphenoxy)-N-(4-fluoro-2-methoxy-5-nitrophenyl)-1,3,5-triazin-2-amine

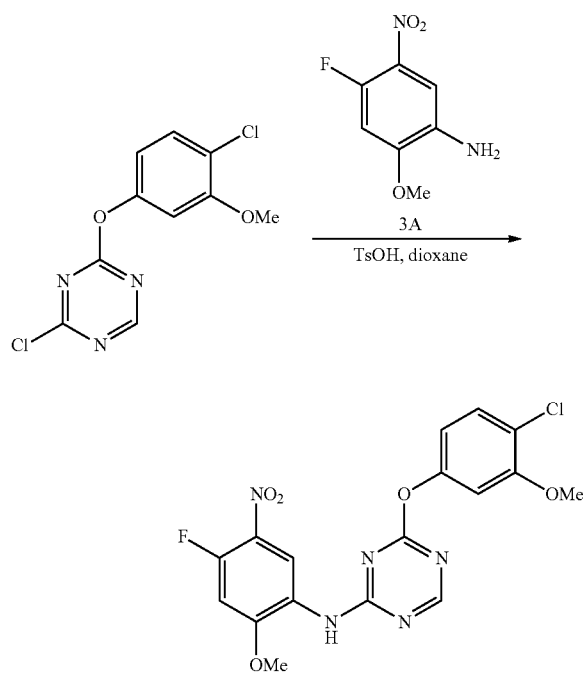

To a solution of 2-chloro-4-(4-chloro-3-methoxyphenolyl)-1,3,5-triazine (700 mg, 2.57 mmol) and compound 3A (575 mg, 3.09 mmol) in 2,4-dioxane (25 mL), TsOH (532 mg, 3.09 mmol) was added, and the reaction solution was stirred at 80° C. for 4 hours. LCMS showed that the reaction was complete. The reaction mixture was poured into water (50 mL), extracted with acetic ether (80 mL×3). The organic phases were combined and dried over anhydrous sodium sulfate, concentrated under reduced pressure and subjected to silica gel column chromatography (petroleum ether:acetic ether=1:2) to obtain a brown solid 4-(4-chloro-3-methoxyphenoxy)-N-(4-fluoro-2-methoxy-5-nitrophenyl)-1,3,5-triazin-2-amine (585 mg, 1.39 mmol, yield: 53.9%).

$^1$H NMR (DMSO-d6, 400 MHz): δ 9.69 (s, 1H), 8.53 (s, 1H), 8.32 (d, J=8.4 Hz, 1H), 7.47-7.31 (m, 2H), 7.09 (s, 1H), 6.83 (d, J=7.6 Hz, 1H), 3.89 (s, 3H), 3.79 (s, 3H).

c. Synthesis of N$^1$-(4-(4-chloro-3-methoxyphenoxy)-1,3,5-triazin-2-yl)-N$^4$-(2-(dimethylamino)ethyl)-2-methoxy-N$^4$-methyl-5-nitrophenyl-1,4-diamine

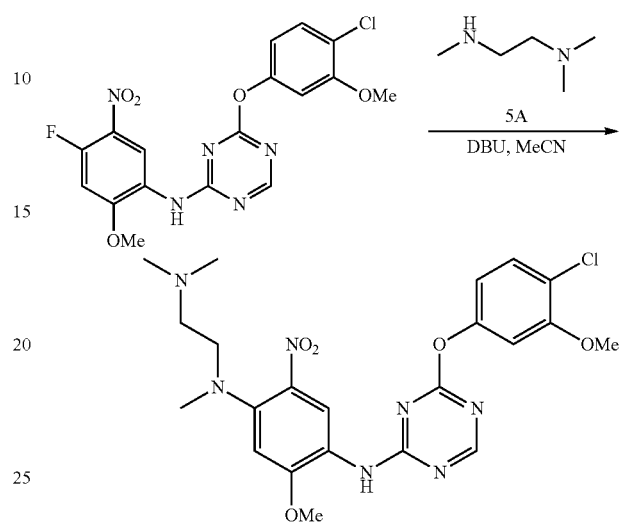

4-(4-chloro-3-methoxyphenoxy)-N-(4-fluoro-2-methoxy-5-nitrophenyl)-1,3,5-triazin-2-amine (585 mg, 1.39 mmol) was dissolved in acetonitrile ACN (10 mL), compound 5A (212 mg, 2.08 mmol, 270 μL) and DBU (317 mg, 2.08 mmol, 313 μL) were added, and the reaction mixture was stirred at 20° C. for 5 hours, LCMS showed the reaction was complete. After concentration under reduced pressure, it was dissolved in dichloromethane DCM (50 mL) and extracted with water (50 mL). The aqueous phase was further extracted with dichloromethane DCM (30 mL). The organic phases were combined and dried over anhydrous sodium sulfate, concentrated by pressure and subjected to silica gel column chromatography (DCM:MeOH=10:1) to obtain yellow oil N$^1$-(4-(4-chloro-3-methoxyphenoxy)-1,3,5-triazin-2-yl)-N$^4$-(2-(dimethylamino)ethyl)-2-methoxy-N$^4$-methyl-5-nitrophenyl-1,4-diamine (425 mg, yield: 60.8%).

$^1$H NMR (CDCl$_3$, 400 MHz): δ 8.62-8.51 (m, 1H), 7.73-7.52 (m, 1H), 7.43-7.40 (m, 1H), 6.78-6.76 (m, 2H), 6.64 (s, 1H), 3.94 (s, 3H), 3.89 (s, 3H), 3.28 (s, 2H), 2.86 (s, 3H), 2.56-2.54 (m, 2H), 2.25 (s, 6H).

d. Synthesis of N$^4$-(4-(4-chloro-3-methoxyphenoxy)-1,3,5-triazin-2-yl)-N$^1$-(2-(dimethylamino)ethyl)-5-methoxy-N$^1$-methylphenyl-1,2,4-triamine

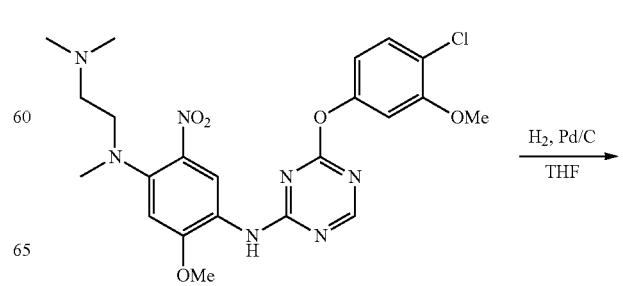

-continued

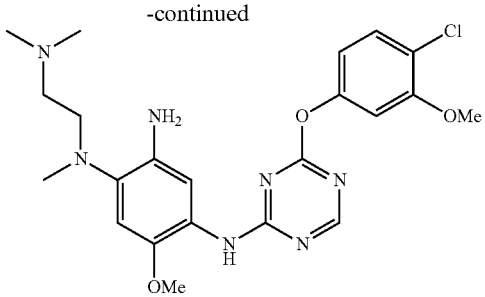

$N^1$-(4-(4-chloro-3-methoxyphenoxy)-1,3,5-triazin-2-yl)-$N^4$-(2-(dimethylamino)ethyl)-2-methoxy-$N^4$-methyl-5-nitrophenyl-1,4-diamine (425 mg, 843 μmol) was dissolved in THF (10 mL), and Pd/C (50 mg, purity 10%) was added, the reaction solution was stirred at 25° C. under hydrogen (16 psi) for 3 hours. LCMS showed that the reaction was complete. The reaction mixture was filtered through celite, and the filter cake was washed with THF (10 mL). The resulting filtrate was concentrated under reduced pressure and subjected to silica gel column chromatography (DCM: MeOH:NH$_4$OH=10:1:0.1) to obtain a brown oily compound $N^4$-(4-(4-chloro-3-methoxyphenoxy)-1,3,5-triazin-2-yl)-$N^1$-(2-(dimethylamino)ethyl)-5-methoxy-$N^1$-methylphenyl-1,2,4-triamine (310 mg, yield: 77.5%).

e. Synthesis of N-(5-((4-(4-chloro-3-methoxyphenoxy)-1,3,5-triazin-2-yl)amino)-2-((2-(dimethylamino)ethyl(methyl)amino)-4-methoxyphenyl)acrylamide

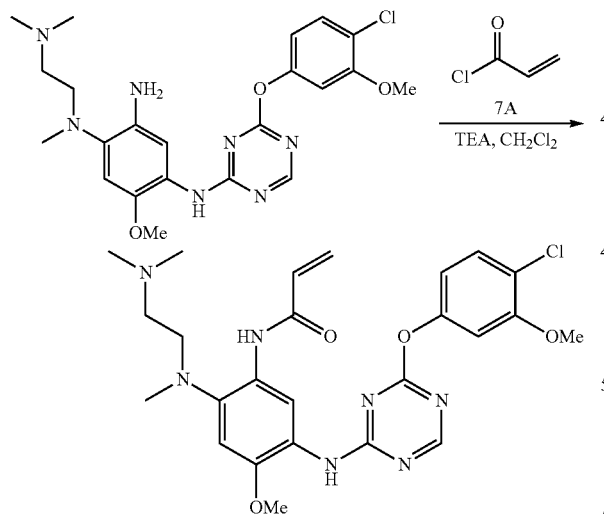

$N^4$-(4-(4-chloro-3-methoxyphenoxy)-1,3,5-triazin-2-yl)-$N^1$-(2-(dimethylamino)ethyl)-5-methoxy-$N^1$-methylphenyl-1,2,4-triamine (435 mg, 0.92 mmol) and triethylamine (185 mg, 1.84 mmol, 255 μL) were dissolved in dichloromethane DCM (30 mL), compound 7A (107 mg, 1.19 mmol, 97.3 μL) previously dissolved in dichloromethane DCM (5 mL) was added to the reaction mixture, the reaction solution was stirred at 20° C. for 5 hours, and LCMS showed that the reaction was complete. The reaction mixture was added with dichloromethane DCM (50 mL) and extracted with water (30 mL). The resulting aqueous phase was further extracted with dichloromethane DCM (20 mL). The organic phases were combined, dried over anhydrous sodium sulfate, concentrated under reduced pressure, and subjected to silica gel column chromatography (DCM:MeOH=10:1) to obtain a yellow solid N-(5-((4-(4-chloro-3-methoxyphenoxy)-1,3,5-triazin-2-yl)amino)-2-((2-(dimethylamino)ethyl(methyl)amino)-4-methoxyphenyl)acrylamide (160 mg, yield: 33.0%).

$^1$H NMR (CDCl$_3$, 400 MHz): δ 10.09 (s, 1H), 9.94-9.02 (m, 1H), 8.67-8.47 (m, 1H), 7.65 (s, 1H), 7.38 (s, 1H), 6.80-6.76 (m, 3H), 6.46-6.42 (m, 2H), 5.73-5.70 (m, 1H), 3.88-3.85 (s, 6H), 2.90 (s, 2H), 2.70 (s, 3H), 2.32 (s, 8H). ESI-MS (m/z): [M+H]$^+$ 528.1.

Example 13

Synthesis of N-(5-((4-(4-chloro-3-methoxyphenoxy)-1,3,5-triazin-2-yl)amino)-4-(difluoromethoxy)-2-((2-(dimethylamino)ethyl(methyl)amino)phenyl)acrylamide (Compound 13)

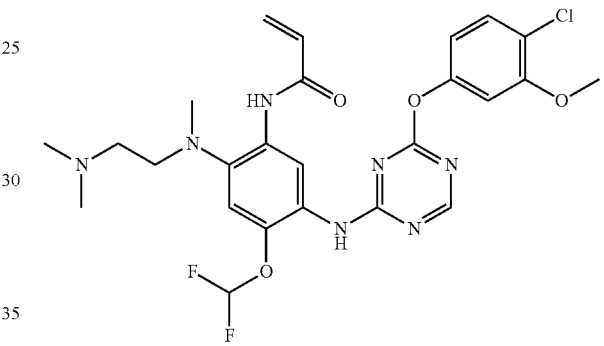

a. Synthesis of 2-(difluoromethoxy)-4-fluoro-1-nitrobenzene

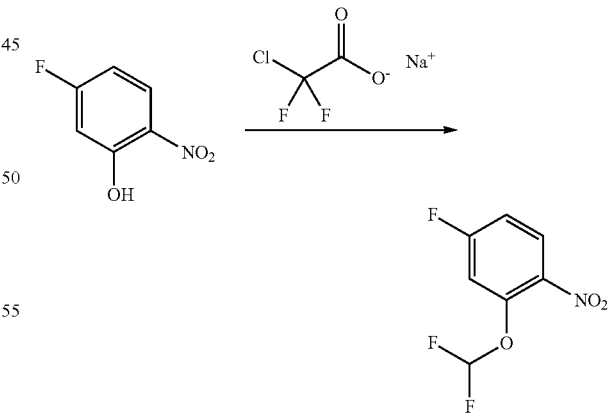

5-Fluoro-2-nitrophenol (5.00 g, 31.83 mmol) and sodium carbonate (10.1 g, 95.5 mmol) were dissolved in DMF (50 mL), and 2-chloro-2,2-sodium difluoroacetate (17.7 g, 116 mmol) was added in portions at 90° C., the reaction mixture was stirred at this temperature for 2 hours, TLC (petroleum ether:acetic ether=5:1) showed the reaction was complete, the reaction mixture was cooled to 25° C. and poured into ice water (400 mL), extract with acetic ether (100 mL×3). the organic phases were combined and washed with water (200 mL×2). The organic phases are dried over anhydrous sodium sulfate, concentrated under reduced pressure and passed through silica gel column chromatography (petroleum ether:acetic ether=10:1) to obtain a yellow oily substance 2-(difluoromethoxy)-4-fluoro-1-nitrobenzene (6.00 g, yield: 91.0%).

¹H NMR (CDCl₃, 400 MHz): δ 8.07-7.96 (m, 1H), 7.15-7.07 (m, 2H), 6.64 (t, J=72.4 Hz, 1H).

b. Synthesis of 2-(difluoromethoxy)-4-fluoroaniline

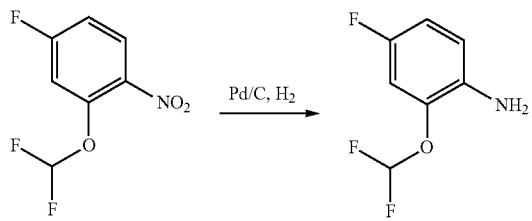 [SMILES: O=[N+]([O-])c1ccc(F)cc1OC(F)F ; Nc1ccc(F)cc1OC(F)F]

2-(Difluoromethoxy)-4-fluoro-1-nitrobenzene (6 g, 28.97 mmol) was dissolved in ethanol (100 mL), Pd/C (600 mg, purity 10%) was added, the reaction solution was stirred at 25° C. under hydrogen (16 psi) for 3 hours. TLC (petroleum ether:acetic ether=3:1) showed that the reaction was complete. The reaction mixture was filtered through celite, and the filter cake was washed with methanol (200 mL) to obtain a crude brown oily compound 2-(difluoromethoxy)-4-fluoroaniline (4.0 g, yield: 77.9%).

¹H NMR (CDCl₃, 400 MHz): δ 6.83-6.76 (m, 1H), 6.75-6.72 (m, 2H), (t, J=74.0 Hz, 1H), 3.71 (s, 2H).

c. Synthesis of 2-(difluoromethoxy)-4-fluoro-5-nitroaniline

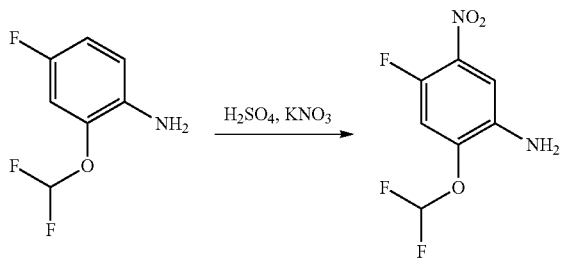 [SMILES: Nc1ccc(F)cc1OC(F)F ; Nc1cc([N+](=O)[O-])c(F)cc1OC(F)F]

2-(Difluoromethoxy)-4-fluoroaniline (4.00 g, 19.3 mmol) was dissolved in concentrated sulfuric acid (50 mL) and KNO₃ (2.15 g, 21.3 mmol) was added at 0° C. The reaction mixture was stirred at 0-20° C. for 2.5 hours, TLC (petroleum ether:acetic ether=5:1) showed that the reaction was complete. The reaction mixture was poured into ice water (500 mL) and extracted with dichloromethane DCM (200 mL×3). The organic phases were combined and washed with water (200 mL×2), dried over anhydrous sodium sulfate, and concentrated under reduced pressure to obtain a yellow solid 2-(difluoromethoxy)-4-fluoro-5-nitroaniline (4.00 g, yield: 93.2%).

¹H NMR (CDCl₃, 400 MHz): δ 7.47 (d, J=6.8 Hz, 1H), 7.01 (d, J=7.2 Hz, 1H), 6.59 (t, J=72.0 Hz, 1H), 4.02 (s, 2H).

d. Synthesis of 4-(4-chloro-3-methoxyphenoxy)-N-(2-(difluoromethoxy)-4-fluoro-5-nitrophenyl)-1,3,5-triazin-2-amine

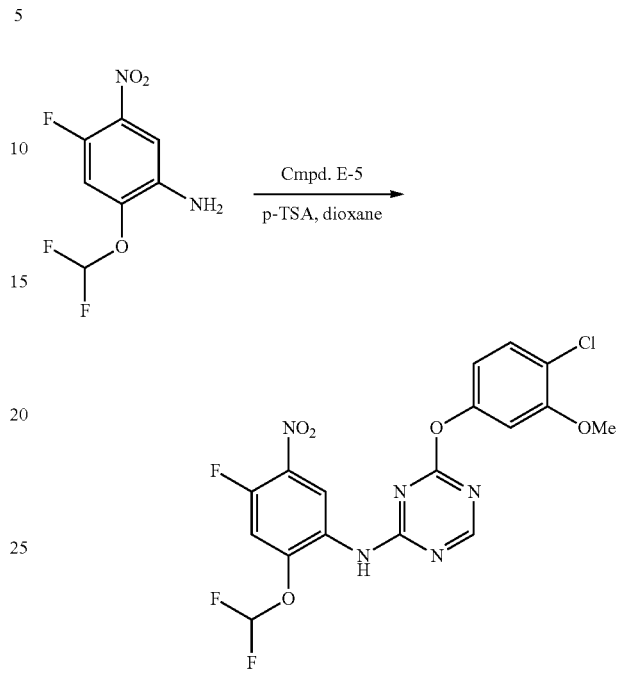

To a solution of (Compound E-5) 2-chloro-4-(4-chloro-3-methoxyphenolyl)-1,3,5-triazine (1.00 g, 3.68 mmol) and 2-(difluoromethoxy))-4-fluoro-5-nitroaniline (979 mg, 4.41 mmol) in 2,4-dioxane (50 mL) was added TsOH (823 mg, 4.78 mmol), the reaction solution was stirred at 20° C. for 5 hours, LCMS showed the reaction was complete. The reaction mixture was poured into water (100 mL), extracted with acetic ether (100 mL×2). The organic phases were combined, dried over anhydrous sodium sulfate, concentrated under reduced pressure and subjected to silica gel column chromatography (petroleum ether:acetic ether=1:1) to give a brown solid 4-(4-chloro-3-methoxyphenoxy)-N-(2-(difluoromethoxy)-4-fluoro-5-nitrophenyl)-1,3,5-triazin-2-amine (700 mg, 1.39 mmol, yield: 41.6%).

e. Synthesis of N¹-(4-(4-chloro-3-methoxyphenoxy)-1,3,5-triazin-2-yl)-2-(difluoromethoxy)-N⁴-(2-(dimethylamino) ethyl)-N⁴-methyl-5-nitrophenyl-1,4-diamine

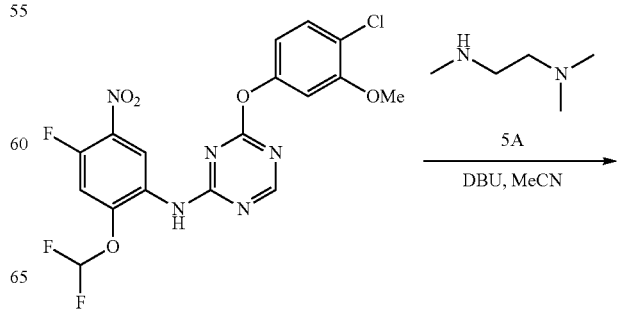

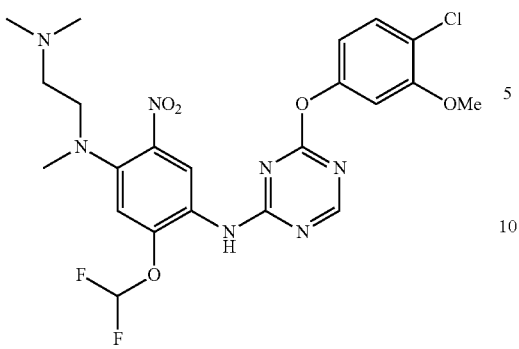

4-(4-chloro-3-methoxyphenoxy)-N-(2-(difluoromethoxy)-4-fluoro-5-nitrophenyl)-1,3,5-triazin-2-amine (700 mg, 1.53 mmol) was dissolved in acetonitrile ACN (30 mL), compound 5A (234 mg, 2.29 mmol, 298 μL) and DBU (349 mg, 2.29 mmol, 345 μL) were added, and the reaction mixture was stirred at 20° C. for 5 hours, LCMS showed that the reaction was complete. After concentration under reduced pressure, it was redissolved in dichloromethane DCM (50 mL) and extracted with water (50 mL×3). The aqueous phase was further extracted with dichloromethane DCM (30 mL). The organic phases were combined, dried over anhydrous sodium sulfate, concentrated under reduced pressure and passed through silica gel column chromatography (DCM:MeOH=10:1) to obtain a yellow oily substance $N^1$-(4-(4-chloro-3-methoxyphenoxy)-1,3,5-triazin-2-yl)-2-(difluoromethoxy)-$N^4$-(2-(dimethylamino) ethyl)-$N^4$-methyl-5-nitrophenyl-1,4-diamine (560 mg, yield: 67.8%).

$^1$H NMR (CDCl$_3$, 400 MHz): δ 8.55 (s, 1H), 7.55-7.52 (m, 2H), 7.41 (d, J=8.4 Hz, 1H), 6.98 (s, 1H), 6.80-6.44 (m, 3H), 3.88 (s, 3H), 3.28-3.25 (m, 2H), 2.83 (s, 3H), 2.54-2.51 (m, 2H), 2.25 (s, 6H).

f. Synthesis of $N^4$-(4-(4-chloro-3-methoxyphenoxy)-1,3,5-triazin-2-yl)-5-(difluoromethoxy)-$N^1$-(2-(dimethylamino) ethyl)-$N^1$-methylphenyl-1,2,4-triamine

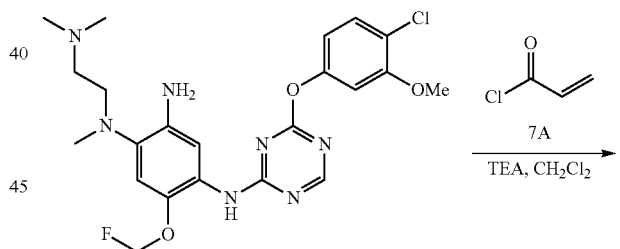

$N^1$-(4-(4-chloro-3-methoxyphenoxy)-1,3,5-triazin-2-yl)-2-(difluoromethoxy)-$N^4$-(2-(dimethylamino) ethyl)-$N^4$-methyl-5-nitrophenyl-1,4-diamine (550 mg, 1.02 mmol) was dissolved in THF (10 mL), and Pd/C (50 mg, purity 10%) was added. The reaction solution was stirred at 25° C. under hydrogen (16 psi) for 2 hours. LCMS showed the reaction was complete. The reaction mixture was filtered through celite, and the filter cake was washed with THF (10 mL). The resulting filtrate was concentrated under reduced pressure and subjected to silica gel column chromatography (DCM:MeOH=10:1) to obtain a pink solid $N^4$-(4-(4-chloro-3-methoxyphenoxy)-1,3,5-triazin-2-yl)-5-(difluoromethoxy)-$N^1$-(2-(dimethylamino) ethyl)-$N^1$-methylphenyl-1,2,4-triamine (445 mg, yield: 85.6%).

g. Synthesis of N-(5-((4-(4-chloro-3-methoxyphenoxy)-1,3,5-triazin-2-yl)amino)-4-(difluoromethoxy)-2-((2-(dimethylamino)ethyl(methyl)amino)phenyl)acrylamide

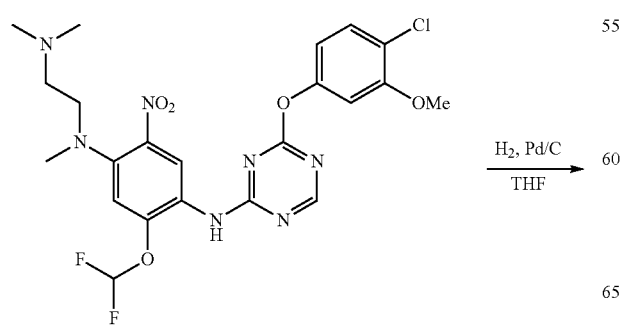

$N^4$-(4-(4-chloro-3-methoxyphenoxy)-1,3,5-triazin-2-yl)-5-(difluoromethoxy)-$N^1$-(2-(dimethylamino) ethyl)-$N^1$-methylphenyl-1,2,4-triamine (435 mg, 0.85 mmol) and triethylamine (172 mg, 1.71 mmol, 237 μL) were dissolved in dichloromethane DCM (30 mL). Compound 7A (115 mg, 1.28 mmol, 104 μL) previously dissolved in dichloromethane DCM (5 mL) was added to the reaction mixture. The reaction solution was stirred at 20° C. for 5 hours. LCMS showed that the reaction was complete. The reaction mixture was added with dichloromethane DCM (50 mL×3) and extracted with water (30 mL). The resulting aqueous phase was further extracted with dichloromethane DCM (20 mL). The organic phases were combined, dried over anhydrous sodium sulfate, and concentrated under reduced pressure, and subjected to silica gel column chromatography (DCM:MeOH=10:1) to obtain a yellow solid N-(5-((4-(4-chloro-3-methoxyphenoxy)-1,3,5-triazin-2-yl)amino)-4-(difluoromethoxy)-2-((2-(dimethylamino)ethyl(methyl)amino)phenyl)acrylamide (300 mg, yield: 62.4%).

$^1$H NMR (CDCl$_3$, 400 MHz): δ 10.30 (s, 1H), 9.40-9.10 (m, 1H), 8.57 (s, 1H), 7.37 (s, 2H), 7.02 (s, 1H), 6.80-6.78 (m, 2H), 6.63 (s, 1H), 6.47-6.43 (m, 2H), 6.33-6.27 (s, 1H), 5.75-5.73 (s, 1H), 3.86 (s, 3H), 2.81 (s, 2H), 2.69 (s, 3H), 2.33 (s, 2H), 2.28 (s, 6H).

ESI-MS (m/z): [M+H]$^+$ 564.1.

Example 14

Synthesis of N-(4-(difluoromethoxy)-2-((2-(dimethylamino)ethyl)(methyl)amino)-5-((4-(5-fluoro-1-methyl-1H-indol-3-yl)-1,3,5-triazin-2-yl)amino)phenyl)acrylamide (Compound 14)

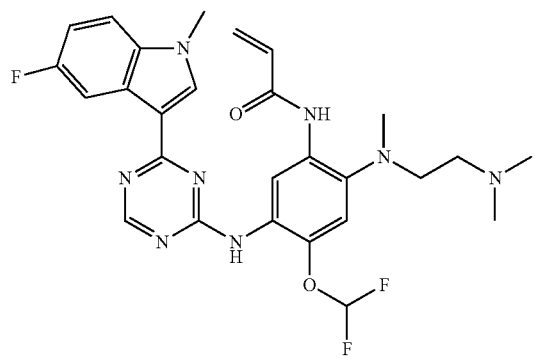 [SMILES: C=CC(=O)Nc1cc(Nc2ncnc(-c3cn(C)c4ccc(F)cc34)n2)c(OC(F)F)cc1N(C)CCN(C)C]

a. Synthesis of N-(2-(difluoromethoxy)-4-fluoro-5-nitrophenyl)-4-(5-fluoro-1-methyl-1H-indol-3-yl)-1,3,5-triazin-2-amine

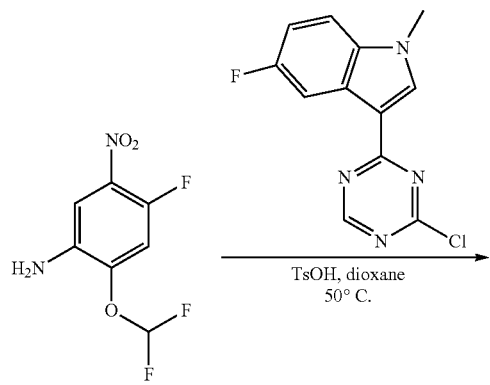

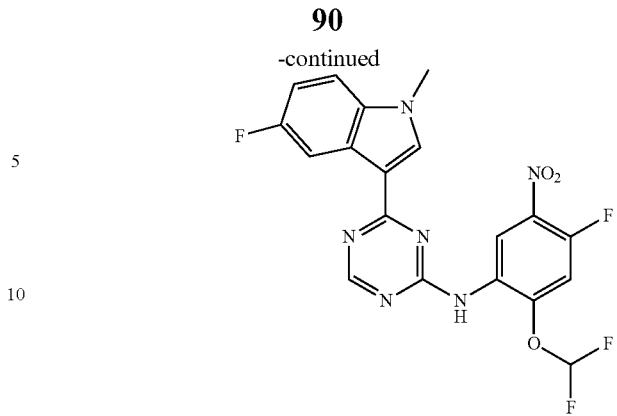

To a solution of 3-(4-chloro-1,3,5-triazin-2-yl)-5-fluoro-1-methyl-1H-indole (130 mg, 0.50 mmol) and 2-(difluoromethoxy)-4-fluoro-5-nitroaniline (132 mg, 0.59 mmol) in 2,4-dioxane (20 mL), TsOH (111 mg, 0.64 mmol) was added, and the reaction solution was stirred at 80° C. for 3 hours, and LCMS showed the reaction was complete. The reaction mixture was poured into water (50 mL), the solid was filtered and washed with water (10 mL), and concentrated under reduced pressure to obtain a brown solid N-(2-(difluoromethoxy)-4-fluoro-5-nitrophenyl)-4-(5-fluoro-1-methyl-1H-indol-3-yl)-1,3,5-triazin-2-amine (220 mg, yield: 98.2%).

b. Synthesis of 2-(difluoromethoxy)-N$^4$-(2-(dimethylamino)ethyl)-N$^1$-(4-(5-fluoro-1-methyl-1H-indol-3-yl)-1,3,5-triazin-2-yl)-N$^4$-methyl-5-nitrophenyl-1,4-diamine

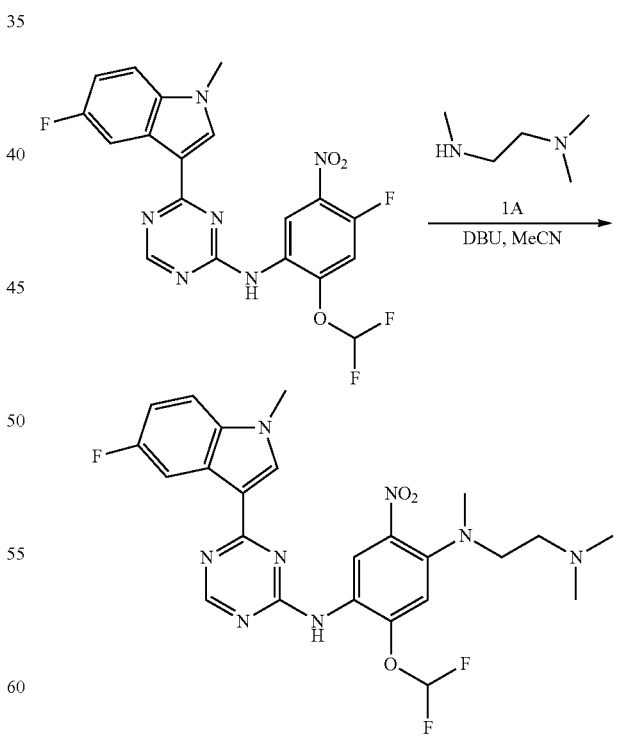

N-(2-(difluoromethoxy)-4-fluoro-5-nitrophenyl)-4-(5-fluoro-1-methyl-1H-indol-3-yl)-1,3,5-triazin-2-amine (220 mg, 0.49 mmol) was dissolved in acetonitrile ACN (30 mL), compound 1A (75.2 mg, 0.74 mmol, 95.7 μL) and DBU (112 mg, 0.74 mmol, 111 μL) were added, and the reaction mixture was stirred at 20° C. for 5 hours, and LCMS showed the reaction was complete. After concentration under reduced pressure, it was redissolved in dichloromethane DCM (50 mL) and extracted with water (40 mL×2). The aqueous phase was further extracted with dichloromethane DCM (30 mL). The organic phases were combined and dried over anhydrous sodium sulfate, concentrated under reduced pressure, and passed through silica gel column chromatography (DCM:MeOH:NH$_4$OH=10:1:0.1) to obtain a yellow solid 2-(difluoromethoxy)-N$^4$-(2-(dimethylamino)ethyl)-N$^1$-(4-(5-fluoro-1-methyl-1H-indol-3-yl)-1,3,5-triazin-2-yl)-N$^4$-methyl-5-nitrophenyl-1,4-diamine (225 mg, yield: 84.5%).

$^1$H NMR (CDCl$_3$, 400 MHz): δ 9.27 (br, 1H), 8.71 (s, 1H), 8.29-8.21 (m, 2H), 7.33-7.27 (m, 2H), 7.08-7.04 (m, 2H), 3.92 (s, 3H), 3.32 (t, J=7.2 Hz, 2H), 2.89 (s, 3H), 2.59 (t, J=6.8 Hz, 2H), 2.28 (s, 6H).

c. Synthesis of 5-(difluoromethoxy)-N$^1$-(2-(dimethylamino)ethyl)-N$^4$-(4-(5-fluoro-1-methyl-1H-indol-3-yl)-1,3,5-triazin-2-yl)-N$^1$-methylphenyl-1,2,4-triamine

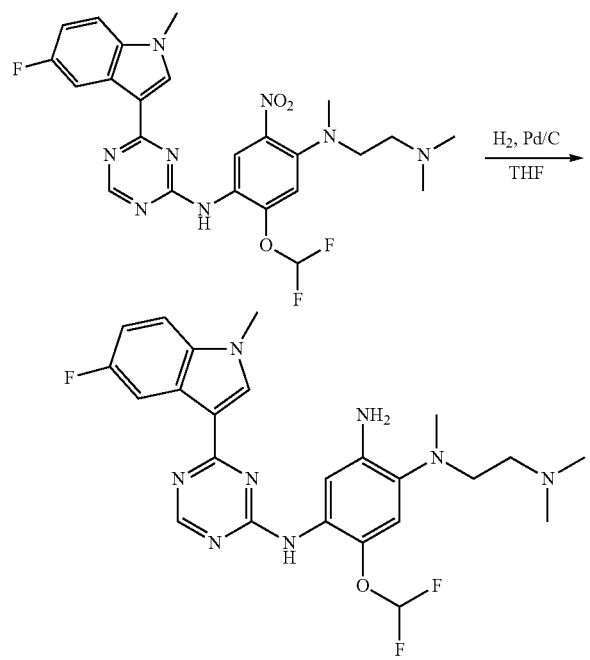

2-(Difluoromethoxy)-N$^4$-(2-(dimethylamino)ethyl)-N$^1$-(4-(5-fluoro-1-methyl-1H-indol-3-yl)-1,3,5-triazin-2-yl)-N$^4$-methyl-5-nitrophenyl-1,4-diamine (220 mg, 0.42 mmol) was dissolved in THF (10 mL) and methanol (3 mL), Pd/C (50 mg, purity 10%) was added, and the reaction solution was stirred at 25° C. under hydrogen (16 psi) for 2 hours. LCMS showed that the reaction was complete. The reaction mixture was filtered through celite, and the filter cake was washed with THF (10 mL). The resulting filtrate was concentrated under reduced pressure to obtain a black solid 5-(difluoromethoxy)-N$^1$-(2-(dimethylamino)ethyl)-N$^4$-(4-(5-fluoro-1-methyl-1H-indol-3-yl)-1,3,5-triazin-2-yl)-N$^1$-methylphenyl-1,2,4-triamine (205 mg, yield: 97.3%).

d. Synthesis of N-(4-(difluoromethoxy)-2-((2-(dimethylamino)ethyl)(methyl)amino)-5-((4-(5-fluoro-1-methyl-1H-indol-3-yl)-1,3,5-triazin-2-yl)amino)phenyl)acrylamide

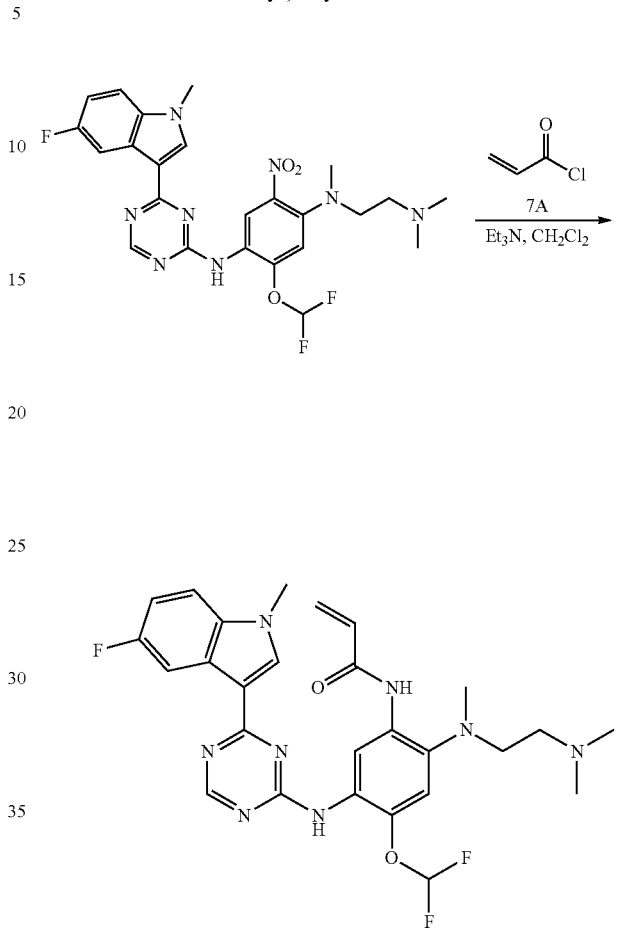

5-(Difluoromethoxy)-N$^1$-(2-(dimethylamino)ethyl)-N$^4$-(4-(5-fluoro-1-methyl-1H-indol-3-yl)-1,3,5-triazin-2-yl)-N$^1$-methylphenyl-1,2,4-triamine (205 mg, 0.41 mmol) and triethylamine (49.7 mg, 0.49 mmol, 40.1 μL) were dissolved in dichloromethane DCM (20 mL), compound 7A (44.5 mg, 0.49 mmol, 40.1 μL) previously dissolved in dichloromethane DCM (2 mL) was added to the reaction mixture, and the reaction solution was stirred at 20° C. for 5 hours. LCMS showed the reaction was complete. The reaction mixture was added with dichloromethane DCM (20 mL) and extracted with water (30 mL). The resulting aqueous phase was further extracted with dichloromethane DCM (20 mL×2). The organic phases were combined, dried over anhydrous sodium sulfate and concentrated under reduced pressure, and subjected to silica gel column chromatography (DCM:MeOH=10:1) to obtain a yellow solid N-(4-(difluoromethoxy)-2-((2-(dimethylamino)ethyl)(methyl)amino)-5-((4-(5-fluoro-1-methyl-1H-indol-3-yl)-1,3,5-triazin-2-yl)amino)phenyl)acrylamide (150 mg, yield: 64.5%).

$^1$H NMR (CDCl$_3$, 400 MHz): δ10.4 (s, 1H), 9.91 (s, 1H), 9.23 (br, 1H), 8.72 (s, 1H), 8.27 (d, J=10.0 Hz, 1H), 7.49 (s, 1H), 7.29-7.27 (m, 1H), 7.08 (s, 1H), 7.05-7.00 (m, 1H), 6.70-6.33 (m, 3H), 5.76 (d, J=11.6 Hz, 1H), 3.96 (s, 3H), 2.88 (s, 2H), 2.71 (s, 3H), 2.29 (m, 8H).

ESI-MS (m/z): [M+H]$^+$ 555.1.

Example 15

Synthesis of N-(2-((2-(dimethylamino)ethyl)(methyl)amino)-5-((4-(5-fluoro-1-methyl-1H-indol-3-yl)-1,3,5-triazin-2-yl)amino)-4-(2,2,2-trifluoroethoxy)phenyl)acrylamide (Compound 15)

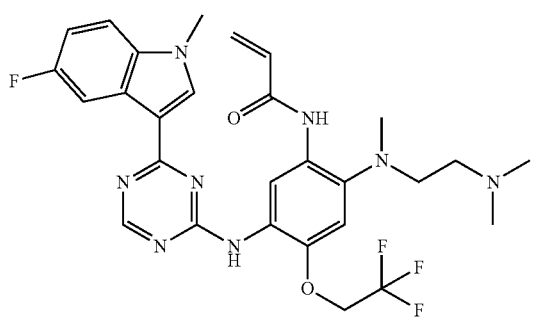 [SMILES: C=CC(=O)Nc1cc(Nc2ncnc(-c3cn(C)c4ccc(F)cc34)n2)c(OCC(F)(F)F)cc1N(C)CCN(C)C]

a. Synthesis of 4-fluoro-1-nitro-2-(2,2,2-trifluoroethoxy)benzene

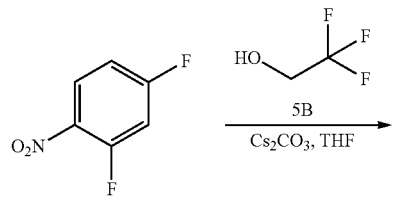

After dissolving 2,4-difluoronitrobenzene (10.0 g, 62.8 mmol) and $Cs_2CO_3$ (20.5 g, 62.8 mmol) in THF (100 mL), compound 5B (6.29 g, 62.8 mmol) was added dropwise, the reaction mixture was stirred at 20° C. for 6 hours, and LCMS showed that the reaction was complete. The reaction mixture was poured into ice water (200 mL) and extracted with acetic ether (150 mL×3). The combined organic phases were washed with saturated brine (300 mL), dried over anhydrous sodium sulfate, filtered and concentrated under reduced pressure, and passed through silica gel column chromatography (petroleum ether:acetic ether=10:1) to obtain a yellow solid 4-fluoro-1-nitro-2-(2,2,2-trifluoroethoxy)benzene (14.0 g, yield: 93.1%).

$^1$H NMR (CDCl$_3$, 400 MHz): δ8.03-7.91 (m, 1H), 6.91-6.82 (m, 2H), 4.54-4.43 (m, 2H).

b. Synthesis of 4-fluoro-2-(2,2,2-trifluoroethoxy)aniline

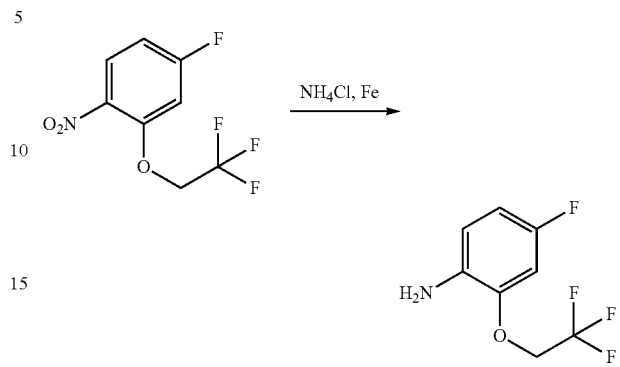

4-Fluoro-1-nitro-2-(2,2,2-trifluoroethoxy) benzene (14.0 g, 58.6 mmol) was dissolved in a mixture of ethanol (40 mL) and water (10 mL), NH$_4$Cl (9.40 g, 175 mmol) was added, iron powder (19.6 g, 351 mmol) was added, and the reaction mixture was stirred at 80° C. for 6 hours. LCMS showed that the reaction was complete. The temperature was cooled to 20° C., and the reaction mixture was filtered through celite. The filtrate was concentrated under reduced pressure and subjected to silica gel column chromatography (petroleum ether:acetic ether=10:1) to obtain a red oily substance 4-fluoro-2-(2,2,2-trifluoroethoxy)aniline (10.0 g, yield: 81.1%).

$^1$H NMR (CDCl$_3$, 400 MHz): δ6.69-6.55 (m, 3H), 4.37-4.31 (m, 2H), 3.69 (br, 2H).

c. Synthesis of 2-(2,2,2-trifluoroethoxy)-4-fluoro-5-nitroaniline

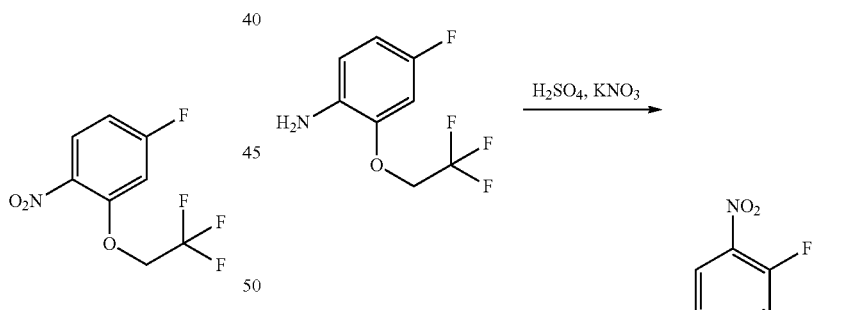

4-Fluoro-2-(2,2,2-trifluoroethoxy) aniline (10.0 g, 47.8 mmol) was dissolved in concentrated sulfuric acid (35 mL) and KNO$_3$ (5.80 g, 57.4 mmol) was added at 0° C., and the reaction mixture was stirred at 0-20° C. for 2.5 hours. TLC (petroleum ether:acetic ether=5:1) showed that the reaction was complete. The reaction mixture was poured into ice water (500 mL) and extracted with dichloromethane DCM (50 mL×10). The organic phases were combined and washed with saturated brine (200 mL), dried over anhydrous sodium sulfate, and concentrated under reduced pressure and subjected to silica gel column chromatography (petroleum ether:acetic ether=8:1) to obtain a yellow solid 2-(2,2,2-trifluoroethoxy)-4-fluoro-5-nitroaniline (8.20 g, yield: 64.8%).

$^1$H NMR (CDCl$_3$, 400 MHz): δ7.43 (d, J=7.6 Hz, 1H), 6.65 (d, J=11.6 Hz, 1H), 4.48-4.42 (m, 2H), 3.99 (br, 2H).

d. Synthesis of 4-(5-fluoro-1-methyl-1H-indol-3-yl)-N-(4-fluoro-5-nitro-2-(2,2,2-trifluoroethoxy)phenyl)-1,3,5-triaz in-2-amine

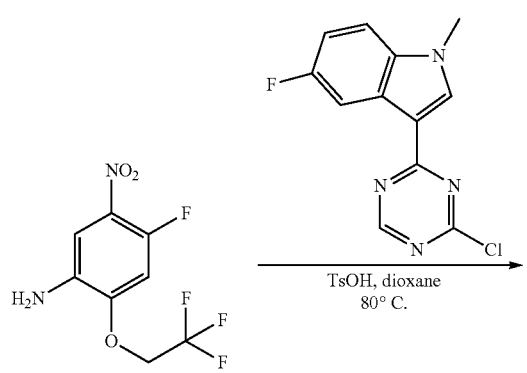

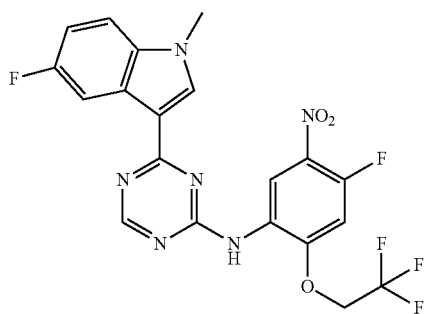

To a solution of 3-(4-chloro-1,3,5-triazin-2-yl)-5-fluoro-1-methyl-1H-indole (300 mg, 1.14 mmol) and 2-(2,2,2-trifluoroethoxy)-4-fluoro-5-nitroaniline (348 mg, 1.37 mmol) in 2,4-dioxane (20 mL), TsOH (256 mg, 1.48 mmol) was added, and the reaction solution was stirred at 80° C. for 3 hours. LCMS showed that the reaction was complete. The reaction mixture was poured into water (50 mL), the solid was filtered and washed with water (10 mL), and concentrated under reduced pressure to obtain a yellow solid 4-(5-fluoro-1-methyl-1H-indol-3-yl)-N-(4-fluoro-5-nitro-2-(2,2,2-trifluoroethoxy)phenyl)-1,3,5-triaz in-2-amine (549 mg, Yield: 98.1%).

$^1$H NMR (CDCl$_3$, 400 MHz): δ9.56 (s, 1H), 8.62 (s, 1H), 8.53 (d, J=7.6 Hz, 1H), 8.37 (s, 1H), 7.63-7.54 (m, 2H), 7.12-7.08 (m, 1H), 5.01-4.95 (m, 2H), 3.89 (s, 3H).

e. Synthesis of N$^1$-(2-(dimethylamino)ethyl)-N$^4$-(4-(5-fluoro-1-methyl-1H-indol-3-yl)-1,3,5-triazin-2-yl)-N$^1$-methyl-2-nitro-5-(2,2,2-trifluoroethoxy)phenyl-1,4-diamine

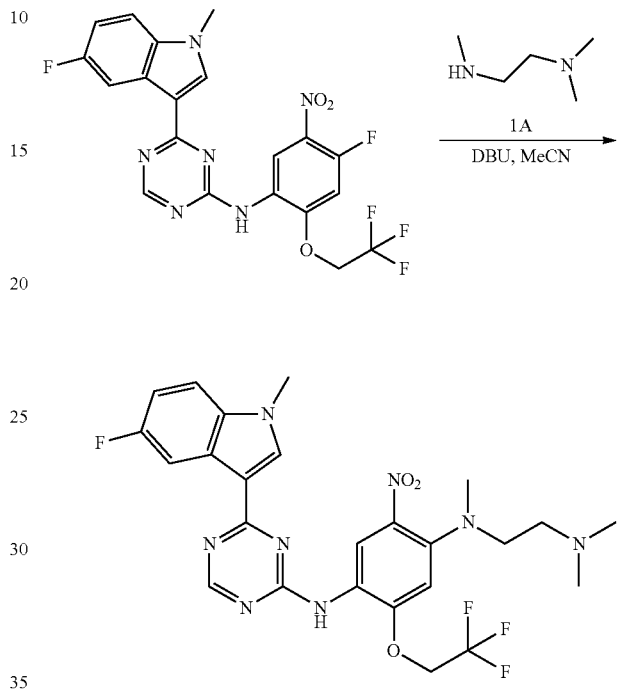

4-(5-fluoro-1-methyl-1H-indol-3-yl)-N-(4-fluoro-5-nitro-2-(2,2,2-trifluoroethoxy)phenyl)-1,3,5-triaz in-2-amine (519 mg, 1.08 mmol) was dissolved in acetonitrile ACN (30 mL), compound 1A (166 mg, 1.62 mmol) and DBU (247 mg, 1.62 mmol) were added, The reaction mixture was stirred at 80° C. for hours, and LCMS showed that the reaction was complete. After concentration under reduced pressure, it was redissolved in dichloromethane DCM (100 mL) and extracted with water (40 mL×2). The aqueous phase was further extracted with dichloromethane DCM (30 mL). The organic phases were combined, dried over anhydrous sodium sulfate, concentrated under reduced pressure and subjected to silica gel column chromatography (DCM: MeOH:NH$_4$OH=10:1:0.1) to obtain a yellow solid N$^1$-(2-(dimethylamino)ethyl)-N$^4$-(4-(5-fluoro-1-methyl-TH-indol-3-yl)-1,3,5-triazin-2-yl)-N$^1$-methyl-2-nitro-5-(2,2,2-trifluoroethoxy)phenyl-1,4-diamine (600 mg, yield: 98.7%).

$^1$H NMR (CDCl$_3$, 400 MHz): δ10.6 (br, 1H), 9.38 (s, 1H), 8.56 (s, 1H), 8.36 (s, 1H), 8.15 (s, 1H), 7.56-7.53 (m, 1H), 7.10 (s, 2H), 4.96 (d, J=8.0 Hz, 2H), 3.89 (s, 3H), 3.65 (s, 2H), 3.56-3.45 (m, 1H), 2.86 (s, 3H), 2.75 (s, 6H), 2.55-2.33 (m, 1H), 1.94-1.89 (s, 0.5H), 1.67-1.61 (m, 1.5H).

f. Synthesis of N¹-(2-(dimethylamino)ethyl)-N⁴-(4-(5-fluoro-1-methyl-TH-indol-3-yl)-1,3,5-triazin-2-yl)-N¹-methyl-5-(2,2,2-trifluoroethoxy)phenyl-1,2,4-triamine

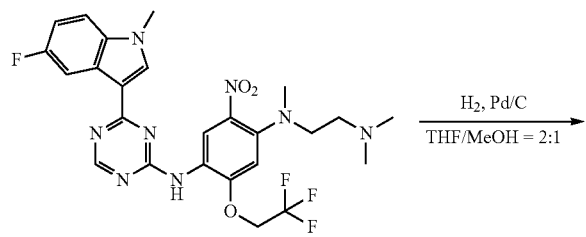

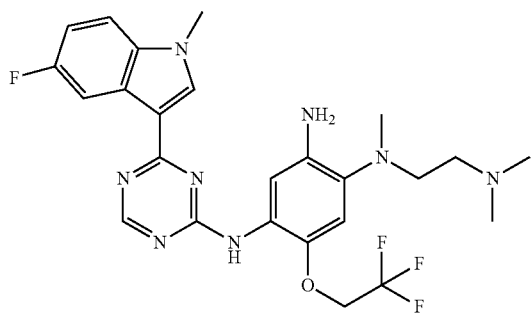

N¹-(2-(dimethylamino)ethyl)-N⁴-(4-(5-fluoro-1-methyl-TH-indol-3-yl)-1,3,5-triazin-2-yl)-N¹-methyl-2-nitro-5-(2,2,2-trifluoroethoxy)phenyl-1,4-diamine (250 mg, 0.44 mmol) was dissolved in THF (20 mL) and methanol (10 mL), Pd/C (50 mg, purity 10%) was added, and the reaction solution was stirred at 25° C. under hydrogen (16 psi) for 2 hours. LCMS showed the reaction was complete. The reaction mixture was filtered through celite, and the filter cake was washed with THF (10 mL). The resulting filtrate was concentrated under reduced pressure to obtain a black solid N¹-(2-(dimethylamino)ethyl)-N⁴-(4-(5-fluoro-1-methyl-TH-indol-3-yl)-1,3,5-triazin-2-yl)-N¹-methyl-5-(2,2,2-trifluoroethoxy)phenyl-1,2,4-triamine (230 mg, yield: 96.4%).

g. Synthesis of N-(2-((2-(dimethylamino)ethyl)(methyl)amino)-5-((4-(5-fluoro-1-methyl-1H-indole-3-yl))-1,3,5-triazin-2-yl)amino)-4-(2,2,2-trifluoroethoxy)phenyl)acrylamide

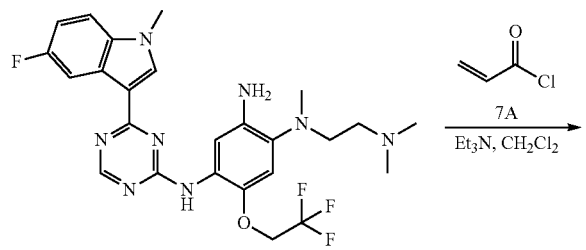

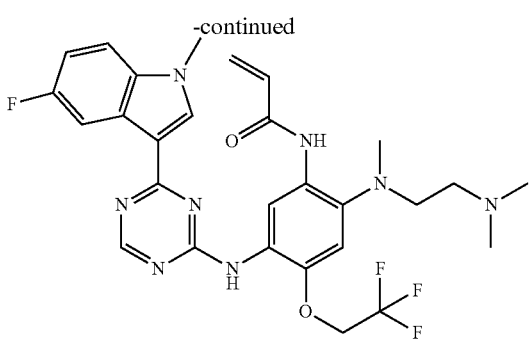

N¹-(2-(dimethylamino)ethyl)-N⁴-(4-(5-fluoro-1-methyl-1H-indol-3-yl)-1,3,5-triazin-2-yl)-N¹-methyl-5-(2,2,2-trifluoroethoxy)phenyl-1,2,4-triamine (230 mg, 0.43 mmol) and triethylamine (52.4 mg, 0.52 mmol, 40.1 μL) was dissolved in dichloromethane DCM (20 mL). Compound 7A (46.9 mg, 0.52 mmol, 40.1 μL) previously dissolved in dichloromethane DCM (2 mL) was added to the reaction mixture. The reaction was stirred at 20° C. for 5 hours, LCMS showed that the reaction was complete. The reaction mixture was added with dichloromethane DCM (20 mL), and extracted with water (30 mL). The resulting aqueous phase was further extracted with dichloromethane DCM (20 mL×2), and the organic phases were combined, washed with saturated brine (50 mL), dried over anhydrous sodium sulfate, concentrated under reduced pressure and subjected to silica gel column chromatography (DCM:MeOH=10:1) to obtain a yellow solid N-(2-((2-(dimethylamino)ethyl)(methyl)amino)-5-((4-(5-fluoro-1-methyl-1H-indol-3-yl)-1,3,5-triazin-2-yl)amino)-4-(2,2,2-trifluoroethoxy)phenyl)acrylamide (140 mg, yield: 53.9%).

¹H NMR (CDCl₃, 400 MHz): δ10.2 (s, 1H), 9.92 (br, 1H), 9.30 (br, 1H), 8.72 (s, 1H), 8.27 (dd, $J_1$=2.0 Hz, $J_2$=10.0 Hz, 1H), 7.61 (s, 1H), 7.29-7.27 (m, 1H), 7.04-6.99 (m, 1H), 6.84 (s, 1H), 6.46-6.42 (m, 2H), 5.76-5.71 (m, 1H), 4.49-4.37 (m, 2H), 3.97 (s, 3H), 2.91-2.88 (m, 2H), 2.71 (s, 3H), 2.36 (s, 2H), 2.31 (s, 6H).

ESI-MS (m/z): [M+H]⁺ 587.1.

Example 16

The compound of formula (II) according to the first aspect of the present invention, the chemical synthesis and preparation of which can refer to an article published in Journal of Medicinal Chemistry, 2015, 58, 8200-8215 by Zeng, Q B, and the patents WO2018/210246(A1), CN105461695A, CN201410365911A, CN201610126987A, CN109761960 and CN106928200A, which is selected from the following compounds: N-(2-((2-(dimethylamino)ethyl(methyl)amino)-4-methoxy-5-((4-(1-methyl-1H-indol-3-yl)-1,3,5-triazin-2-yl)amino)phenyl)acrylamide (Compound 16);

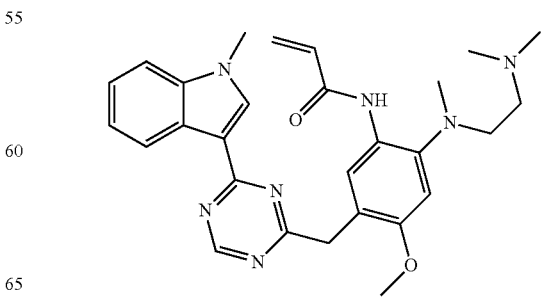

N-(5-((4-(3,3-dimethyl-2,3-dihydro-1H-pyrrolo[3,2-b]pyridin-1-yl)-1,3,5-triazin-2-yl)amino)-2-((2-(dimethylamino)ethyl)(methyl)amino)-4-methoxyphenyl)acrylamide (Compound 17);

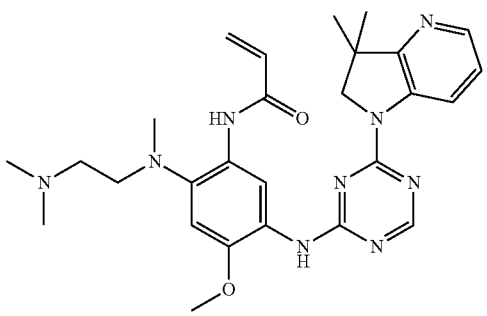 [SMILES: C=CC(=O)Nc1cc(Nc2ncnc(N3CC(C)(C)c4ncccc43)n2)c(OC)cc1N(C)CCN(C)C]

N-(2-((2-(dimethylamino)ethyl)(methyl)amino)-4-methoxy-5-((4-(3-methyl-1H-pyrrolo[3,2-c]pyridin-1-yl)-1,3,5-triazin-2-yl)amino)phenyl)acrylamide (Compound 18);

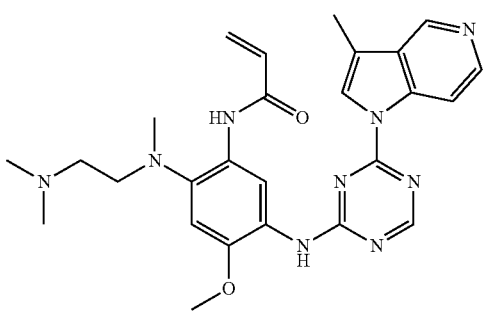 [SMILES: C=CC(=O)Nc1cc(Nc2ncnc(-n3cc(C)c4cnccc43)n2)c(OC)cc1N(C)CCN(C)C]

N-(2-((2-(dimethylamino)ethyl)(methyl)amino)-4-methoxy-5-((4-(8-methylimidazole[1,2-a]pyridin-3-yl)-1,3,5-triazin-2-yl)amino)phenyl)acrylamide (Compound 19);

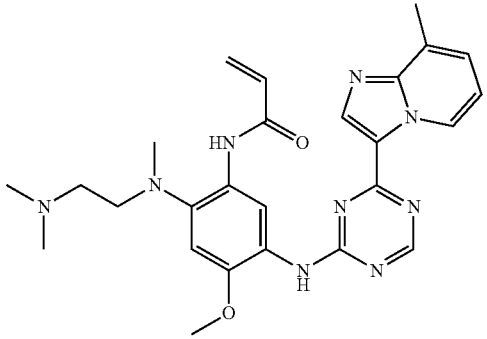 [SMILES: C=CC(=O)Nc1cc(Nc2ncnc(-c3cnc4c(C)cccn34)n2)c(OC)cc1N(C)CCN(C)C]

N-(4-(difluoromethoxy)-5-((4-(5-fluoro-1-methyl-1H-indol-3-yl)pyrimidin-2-yl)amino)-2-(methyl(2-(methylamino)ethyl)amino)phenyl)acrylamide (Compound 20);

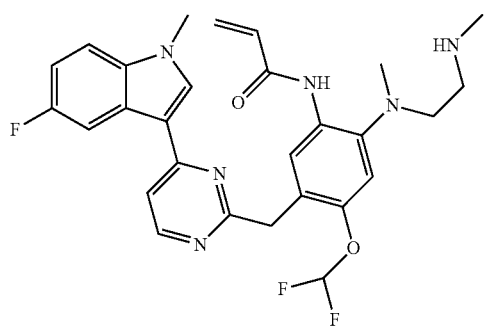 [SMILES: C=CC(=O)Nc1cc(Cc2nccc(-c3cn(C)c4ccc(F)cc34)n2)c(OC(F)F)cc1N(C)CCNC]

N-(2-((2-(dimethylamino)ethyl)(methyl)amino)-5-((4-(5-fluoro-1-methyl-1H-indol-3-yl)pyrimidin-2-yl)amino)-4-methoxyphenyl)acrylamide (Compound 21);

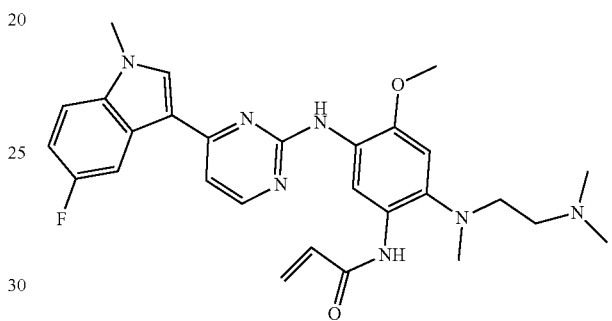

N-(2-((2-(dimethylamino)ethyl)(methyl)amino)-4-ethoxy-5-((4-(5-fluoro-1-methyl-1H-indol-3-yl)pyrimidin-2-yl)amino)phenyl)acrylamide (Compound 22);

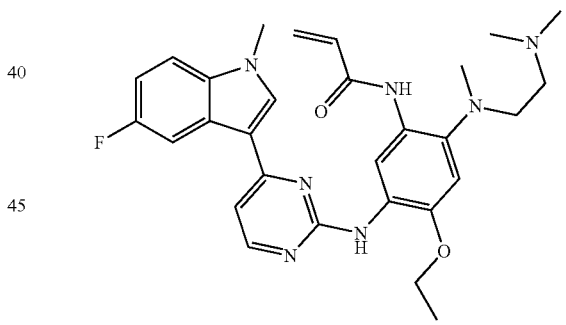

N-(2-((2-(dimethylamino)ethyl)(methyl)amino)-4-ethoxy-5-((4-(1-methyl-1H-indole-3-yl)pyrimidin-2-yl)amino)phenyl)acrylamide (Compound 23);

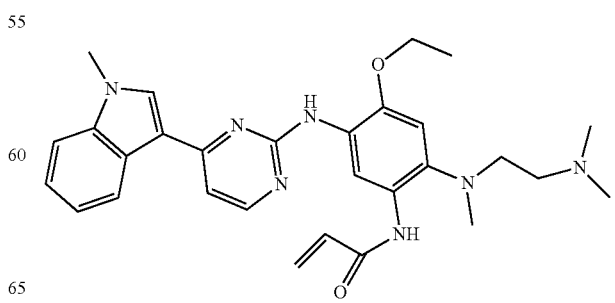

N-(4-ethoxy-2-(methyl(2-(methylamino)ethyl)amino)-5-((4-(1-methyl-1H-indol-3-yl)pyrimidine-2-yl) amino) phenyl) acrylamide (Compound 24);

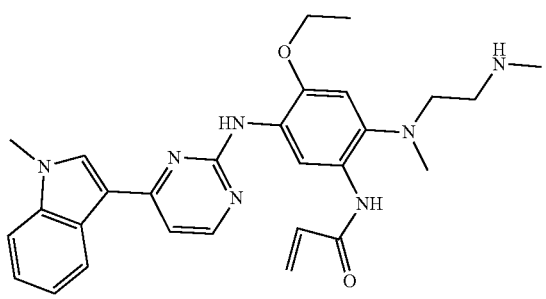 [SMILES: C=CC(=O)Nc1cc(Nc2nccc(-c3cn(C)c4ccccc34)n2)c(OCC)cc1N(C)CCNC]

N-(5-((4-(5-fluoro-1-methyl-1H-indol-3-yl)pyrimidin-2-yl)amino)-4-methoxy-2-(methyl(2-(methylamino)ethyl)amino)phenyl)acrylamide (Compound 25);

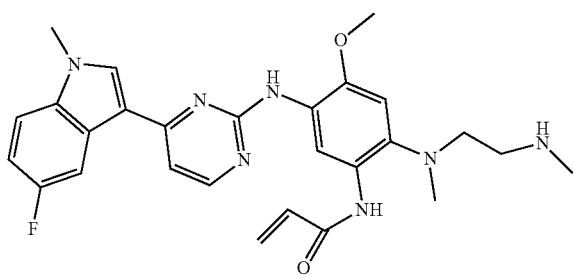 [SMILES: C=CC(=O)Nc1cc(Nc2nccc(-c3cn(C)c4ccc(F)cc34)n2)c(OC)cc1N(C)CCNC]

N-(4-(difluoromethoxy)-2-(methyl(2-(methylamino)ethyl)amino)-5-((4-(1-methyl-1H-indole-3-yl)pyrimidin-2-yl)amino)phenyl)acrylamide (Compound 26);

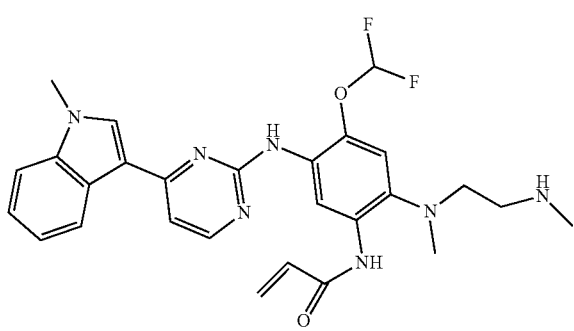 [SMILES: C=CC(=O)Nc1cc(Nc2nccc(-c3cn(C)c4ccccc34)n2)c(OC(F)F)cc1N(C)CCNC]

N-(4-ethoxy-5-((4-(5-fluoro-1-methyl-1H-indol-3-yl)pyrimidin-2-yl)amino)-2-(methyl(2-(methylamino)ethyl)amino)phenyl)acrylamide (Compound 27);

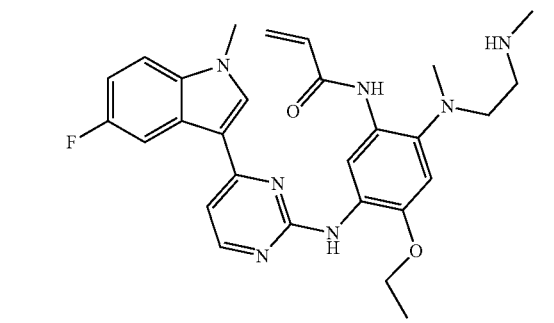 [SMILES: C=CC(=O)Nc1cc(Nc2nccc(-c3cn(C)c4ccc(F)cc34)n2)c(OCC)cc1N(C)CCNC]

N-(5-((4-(1-cyclopropyl-1H-indole)pyrimidin-2-yl)-2-((2-(dimethylamino)ethyl(methyl)amine)-4-methoxyphenyl) acrylamide hydrochloride (Compound 28);

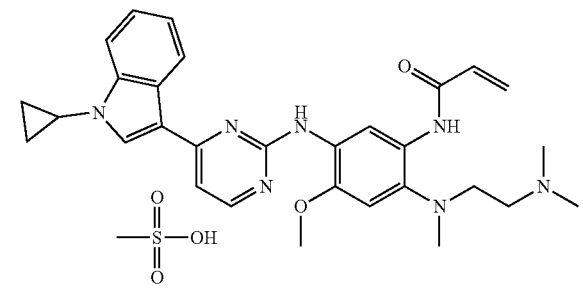

wherein, Compound 28 can be purchased from MedChemExpress under the article number HY-112823B.

N-(5-((4-(1-cyclopropyl-1H-indole)pyrimidin-2-yl)-2-((2-(dimethylamino)ethyl(methyl)amine)-4-methoxyphenyl) acrylamide methanesulfonate (Compound 29);

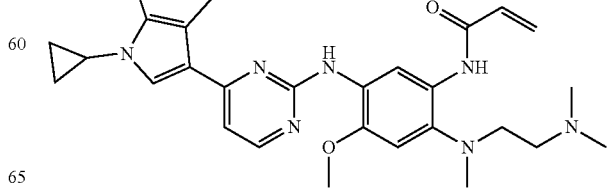

N-(5-((4-(1-cyclopropyl-1H-indole)pyrimidin-2-yl)-2-((2-(dimethylamino)ethyl(methyl)amine)-4-methoxyphenyl) acrylamide (Compound 30);

wherein, compound 30 can be purchased from Selleck-chem under the article number S-8817.

N-(2-((2-(dimethylamino)ethyl(methyl)amine)-5-((4-(1-methyl-1H-indol-3-yl)pyrimidine-2-yl)amino)-6-(2,2,2-trifluoroethoxy)pyridin-3-yl)acrylamide methane-sulfonate (Compound 31);

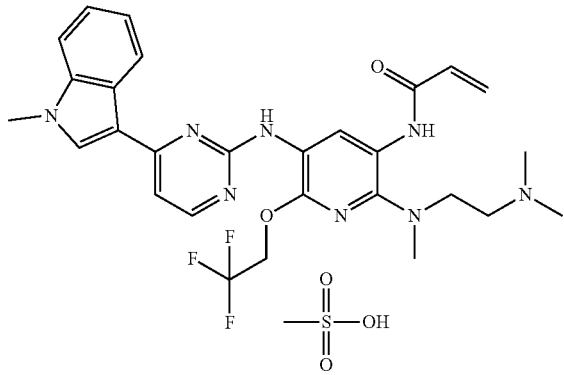

wherein, compound 31 can be purchased from MedChem-Express under the article number HY-112870A.

N-(2-((2-(dimethylamino)ethyl(methyl)amine)-5-((4-(1-methyl-1H-indol-3-yl)pyrimidine-2-yl)amino)-6-(2,2,2-trifluoroethoxy)pyridin-3-yl)acrylamide hydrochloride (Compound 32);

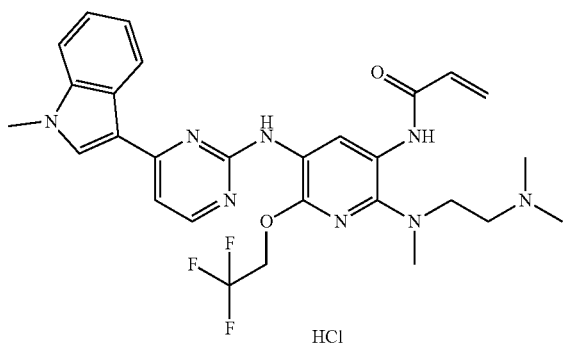

N-(2-((2-(dimethylamine)ethyl(methyl)amine)-5-((4-(1-methyl-1H-indol-3-yl)pyrimidine-2-yl)amino)-6-(2,2,2-trifluoroethoxy)pyridin-3-yl) acrylamide (Compound 33)

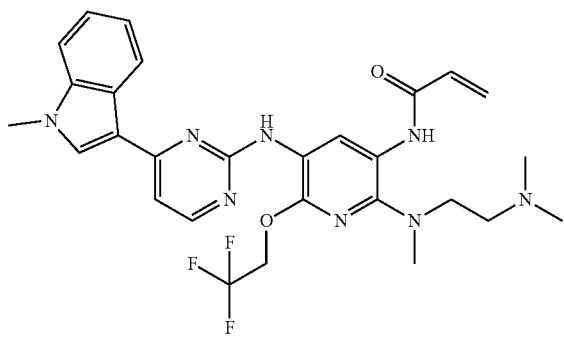

wherein, compound 33 can be purchased from ProbeChem under the article number PC-35640.

N-(5-((4-(4-((dimethylamine)methyl)-3-phenyl-1H-pyrazol-1-yl)pyrimidin-2-yl)amine)-4-methoxy-2-morpholi-nylphenyl)acrylamide (Compound 34);

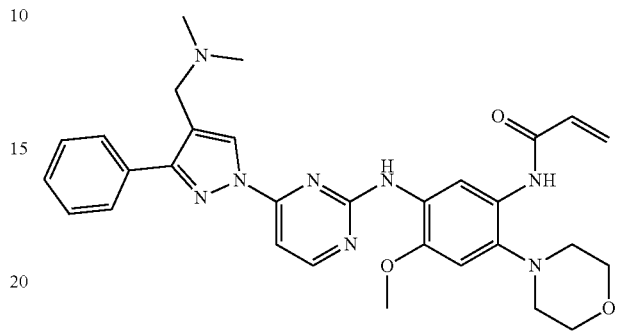

wherein, compound 34 can be purchased from MedChem-Express under the article number HY-109061.

The compound of formula (II) according to the second aspect of the present invention, the chemical synthesis and preparation of which can refer to an article published in Journal of Medicinal Chemistry, 2018, 61, 4290-4300, by Chen, L F, et al. and its references, which is selected from the following compounds:

N-(3-((2-((3-fluoro-4-(4-methylpiperazin-1-yl)phenyl)amine)-7H-pyrazole[2,3-d]pyrimidine-4-yl)ox o)phenyl)acrylamide (Compound 35);

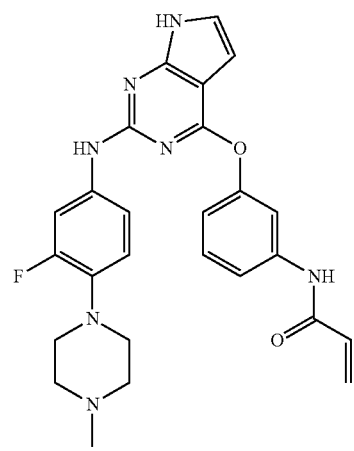

wherein, compound 35 can be purchased from AdooQ Bioscience under the article number A16826.

N-(3-((2-((4-(4-methylpiperazin-1-yl)phenyl)amine)thieno[3,2-d]pyrimidin-4-yl)oxo)phenyl)acrylamide (Compound 36);

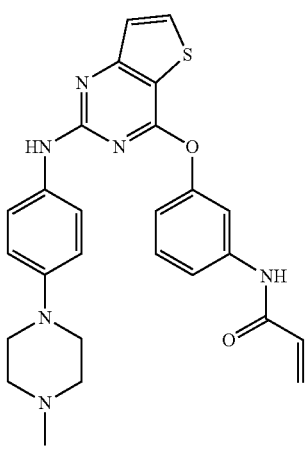

wherein, compound 36 can be purchased from MedChemExpress under the article number HY-19730.

N-(3-((2-((4-(4-acetylpiperazin-1-yl)-2-methoxyphenyl)amine)-6-(trifluoromethoxy)pyrimidine-4-yl) amine)phenyl)acrylamide (Compound 37);

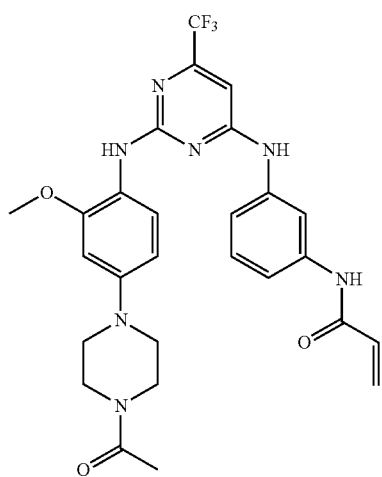

wherein, compound 37 can be purchased from MedChemExpress under the article number HY-15729.

The compound of formula (IV) according to the second aspect of the present invention, the chemical synthesis of which can refer to articles published in Journal of Medicinal Chemistry, 2015, 58, 8200-8215 by Zeng, Q B, et al., which is selected from the following compounds: (R)-4-((3-chloro-2-fluorophenyl)amine)amine)-7-methoxyquinazolin-6-yl-2,4-dimethylpiperazinyl-1-carboxylic acid ester (Compound 38);

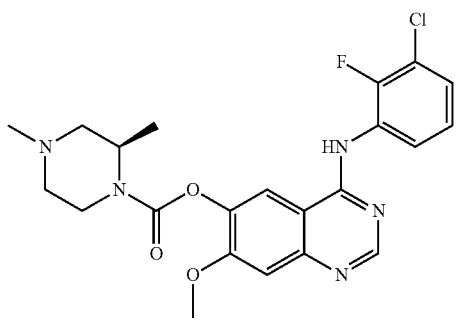

wherein, compound 38 can be purchased from MedChemExpress under the article number HY-18750.

The compound of formula (V) according to the second aspect of the present invention, the chemical synthesis of which can refer to an article published in Journal of Medicinal Chemistry, 2016, 59, 6671-6689 by Lelais, Q et al., which is selected from the following compounds: (R,E)-N-(7-chloro-1-(1-(4-(dimethylamine)-2-butenoyl)azepane-3-yl)-1H-benzo[d]imidazol-2-yl)-2-methylisonicotinamide (Compound 39);

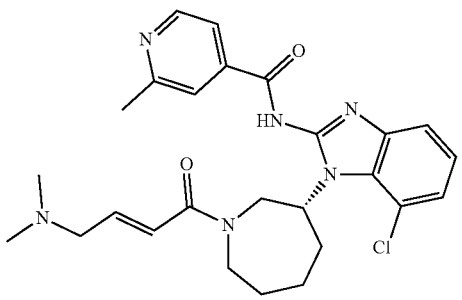

wherein, compound 39 can be purchased from MedChemExpress under the article number HY-12872.

Test 1: EGFR L858R/T790M (EGFR Double Mutant) Cell Proliferation Test

The human lung cell line NCI-H1975 (EGFR L858R/T790M double mutant) was obtained from the American Type Culture Collection. NCI-H1975 cells were cultured in RPMI1640 medium containing 10% fetal bovine serum and 2 mM glutamine. The cells were grown at 37° C. in a humidified incubator with 5% $CO_2$.

The number of viable cells in the culture was measured according to the protocol described in Promega's Cell Titer-Glo Luminescent cell Viability Assay (Promega catalog number #G7570). 90 µl of cells (8,000 cells/well) were cultured in growth medium in a Corning black transparent bottom 96-well plate, and cultured in a 5% $CO_2$ humidified incubator at 37° C. overnight. The compound serially diluted in 100% DMSO was added to the cells using a pipette, and the cells were incubated for another 72 hours. 100 µl of the mixed Cell Titer-Glo reagent was added to the cells in the 96-well culture plate to lyse the cells and mix gently. Subsequently, the autofluorescence was detected on the Envision microplate detector to obtain the data of each compound. Finally, the data was input into a suitable software package (such as Prism) for curve fitting analysis. Based on this data and by calculating the compound concentration required to obtain a 50% inhibitory effect, the $IC_{50}$ value was determined.

Table 1 below showed the $IC_{50}$ values of the compounds in Examples 1-15 herein in the above EGFR L858R/T790M (EGFR double mutant) cell proliferation test.

TABLE 1

| Example number | Test 1 - $IC_{50}$ (nM) |
| --- | --- |
| 1 | 19.82 |
| 2 | 129.6 |
| 3 | 56.97 |
| 4 | 66.70 |
| 5 | 19.50 |
| 6 | 91.04 |
| 7 | 56.97 |

TABLE 1-continued

| Example number | Test 1 - $IC_{50}$ (nM) |
|---|---|
| 8 | 39.6 |
| 9 | 15.3 |
| 10 | 182.7 |
| 11 | 13.5 |
| 12 | 66.3 |
| 13 | 42.1 |
| 14 | 16.8 |
| 15 | 12.7 |
| Osimertinib (AZD9291) | 18.23 |

* Osimertinib (AZD9291) is the third-generation EGFR inhibitor developed by AstraZeneca for the treatment of non-small cell lung cancer, the same below.

Test 2: BaF3 (EGFR-D770insSVD) Cell Proliferation Test

The engineered cell line BaF3 (EGFR-D770insSVD) was constructed by the inventor himself (for the method of cell line construction, see Jingrui Jiang et al., Cancer Res. 2005 Oct. 1; 65 (19): 8964-74; Jacqulyne P. Robichaux et al., Nat Med. 2018 May; 24 (5): 638-646). BaF3 (EGFR-D770insSVD) was cultured in RPMI1640 medium containing 10% fetal bovine serum and 2 mM glutamine. The cells were grown at 37° C. in a humidified incubator with 5% $CO_2$.

The number of viable cells in the culture was measured according to the protocol described in Promega's Cell Titer-Glo Luminescent cell Viability Assay (Promega catalog number #G7570). 90 μl of cells (3,000 cells/well) were cultured in growth medium in a Corning black transparent bottom 96-well plate, and cultured in a 5% $CO_2$ humidified incubator at 37° C. overnight. The compound serially diluted in 100% DMSO was added to the cells using a pipette, and the cells were incubated for another 72 hours. 100 μl of the mixed Cell Titer-Glo reagent was added to the cells in the 96-well culture plate to lyse the cells and mix gently. Subsequently, the autofluorescence was detected on the Envision microplate detector to obtain the data of each compound. Finally, the data was input into a suitable software package (such as Prism) for curve fitting analysis. Based on this data and by calculating the compound concentration required to obtain a 50% inhibitory effect, the $IC_{50}$ value was determined.

Table 2 below showed the $IC_{50}$ values of the compounds in Examples 1, 4-6, 8-15 herein in the above BaF3 (EGFR-D770insSVD) cell proliferation test.

TABLE 2

| Example number | Test 2 - $IC_{50}$ (nM) |
|---|---|
| 1 | 412 |
| 4 | 592.2 |
| 5 | 144.4 |
| 6 | 518.1 |
| 8 | 30.04 |
| 9 | 48.69 |
| 10 | 565.7 |
| 11 | 22.3 |
| 12 | 183.1 |
| 13 | 88.65 |
| 14 | 16.36 |
| 15 | 24.39 |
| Osimertinib (AZD9291) | 305 |

Test 3: BaF3 (EGFR-A763insFOEA) Cell Proliferation Test

The engineered cell line BaF3 (EGFR-A763insFQEA) was constructed by the inventor himself (for the method of cell line construction, see Jingrui Jiang et al., Cancer Res. 2005 Oct. 1; 65 (19): 8964-74; Jacqulyne P. Robichaux et al., Nat Med. 2018 May; 24 (5): 638-646). BaF3 (EGFR-A763insFQEA) was cultured in RPMI1640 medium containing 10% fetal bovine serum and 2 mM glutamine. The cells were grown at 37° C. in a humidified incubator with 5% $CO_2$.

The number of viable cells in the culture was measured according to the protocol described in Promega's Cell Titer-Glo Luminescent cell Viability Assay (Promega catalog number #G7570). 90 μl of cells (3,000 cells/well) were cultured in growth medium in a Corning black transparent bottom 96-well plate, and cultured in a 5% $CO_2$ humidified incubator at 37° C. overnight. The compound serially diluted in 100% DMSO was added to the cells using a pipette, and the cells were incubated for another 72 hours. 100 μl of the mixed Cell Titer-Glo reagent was added to the cells in the 96-well culture plate to lyse the cells and mix gently. Subsequently, the autofluorescence was detected on the Envision microplate detector to obtain the data of each compound. Finally, the data was input into a suitable software package (such as Prism) for curve fitting analysis. Based on this data and by calculating the compound concentration required to obtain a 50% inhibitory effect, the $IC_{50}$ value was determined.

Table 3 below showed the $IC_{50}$ values of the compounds in Examples 1, 4-6, 8-15 herein in the above BaF3 (EGFR-A763insFQEA) cell proliferation test.

TABLE 3

| Example number | Test 3 - $IC_{50}$ (nM) |
|---|---|
| 1 | 279.8 |
| 4 | 312.6 |
| 5 | 42.61 |
| 6 | 277.1 |
| 8 | 16.57 |
| 9 | 14.33 |
| 10 | 182.7 |
| 11 | 9.45 |
| 12 | 57.28 |
| 13 | 43.12 |
| 14 | 7.60 |
| 15 | 14.04 |
| Osimertinib (AZD9291) | 118.6 |

Test 4: BaF3 (EGFR-V769insASV) Cell Proliferation Test

The engineered cell line BaF3 (EGFR-V769insASV) was constructed by the inventor himself (for the method of cell line construction, see Jingrui Jiang et al., Cancer Res. 2005 Oct. 1; 65 (19): 8964-74; Jacqulyne P. Robichaux et al., Nat Med. 2018 May; 24 (5): 638-646). BaF3 (EGFR-V769insASV) was cultured in RPMI1640 medium containing 10% fetal bovine serum and 2 mM glutamine. The cells were grown at 37° C. in a humidified incubator with 5% $CO_2$.

The number of viable cells in the culture was measured according to the protocol described in Promega's Cell Titer-Glo Luminescent cell Viability Assay (Promega catalog number #G7570). 90 μl of cells (3,000 cells/well) were cultured in growth medium in a Corning black transparent bottom 96-well plate, and cultured in a 5% $CO_2$ humidified incubator at 37° C. overnight. The compound serially diluted in 100% DMSO was added to the cells using a pipette, and the cells were incubated for another 72 hours. 100 μl of the mixed Cell Titer-Glo reagent was added to the cells in the 96-well culture plate to lyse the cells and mix gently. Subsequently, the autofluorescence was detected on the Envision microplate detector to obtain the data of each compound. Finally, the data was input into a suitable software package (such as Prism) for curve fitting analysis.

Based on this data and by calculating the compound concentration required to obtain a 50% inhibitory effect, the $IC_{50}$ value was determined.

Table 4 below showed the $IC_{50}$ values of the compounds in Examples 1, 4-6, and 8-15 herein in the above BaF3 (EGFR-V769insASV) cell proliferation test.

TABLE 4

| Example number | Test 4 - $IC_{50}$ (nM) |
| --- | --- |
| 1 | 385.8 |
| 4 | 470 |
| 5 | 147.7 |
| 6 | 476.6 |
| 8 | 57.6 |
| 9 | 45.51 |
| 10 | 465.5 |
| 11 | 47.86 |
| 12 | 121.5 |
| 13 | 88.62 |
| 14 | 25.88 |
| 15 | 45 |
| Osimertinib (AZD9291) | 307.1 |

Test 5: BaF3 (EGFR-N771insH) Cell Proliferation Test

The engineered cell line BaF3 (EGFR-N771insH) was constructed by the inventor himself (for the method of cell line construction, see Jingrui Jiang et al., Cancer Res. 2005 Oct. 1; 65 (19): 8964-74; Jacqulyne P. Robichaux et al., Nat Med. 2018 May; 24 (5): 638-646). BaF3 (EGFR-N771insH) was cultured in RPMI1640 medium containing 10% fetal bovine serum and 2 mM glutamine. The cells were grown at 37° C. in a humidified incubator with 5% $CO_2$.

The number of viable cells in the culture was measured according to the protocol described in Promega's Cell Titer-Glo Luminescent cell Viability Assay (Promega catalog number #G7570). 90 μl of cells (3,000 cells/well) were cultured in growth medium in a Corning black transparent bottom 96-well plate, and cultured in a 5% $CO_2$ humidified incubator at 37° C. overnight. The compound serially diluted in 100% DMSO was added to the cells using a pipette, and the cells were incubated for another 72 hours. 100 μl of the mixed Cell Titer-Glo reagent was added to the cells in the 96-well culture plate to lyse the cells and mix gently. Subsequently, the autofluorescence was detected on the Envision microplate detector to obtain the data of each compound. Finally, the data was input into a suitable software package (such as Prism) for curve fitting analysis. Based on this data and by calculating the compound concentration required to obtain a 50% inhibitory effect, the $IC_{50}$ value wasdetermined.

Table 5 below showed the $IC_{50}$ values of the compounds of Examples 8-15 herein in the above BaF3 (EGFR-N771insH) cell proliferation test.

TABLE 5

| Example number | Test 5 - $IC_{50}$ (nM) |
| --- | --- |
| 8 | 18.21 |
| 9 | 15.33 |
| 10 | 145.7 |
| 11 | 9.19 |
| 12 | 82.5 |
| 13 | 35.6 |
| 14 | 9.21 |
| 15 | 7.66 |
| Osimertinib (AZD9291) | 33.53 |

Test 6: BaF3 (EGFR-D770insNPG) Cell Proliferation Test

The engineered cell line BaF3 (EGFR-D770insNPG) was constructed by the inventor himself (for the method of cell line construction, see Jingrui Jiang et al., Cancer Res. 2005 Oct. 1; 65 (19): 8964-74; Jacqulyne P. Robichaux et al., Nat Med. 2018 May; 24 (5): 638-646). BaF3 (EGFR-D770insNPG) was cultured in RPMI1640 medium containing 10% fetal bovine serum and 2 mM glutamine. The cells were grown at 37° C. in a humidified incubator with 5% $CO_2$.

The number of viable cells in the culture was measured according to the protocol described in Promega's Cell Titer-Glo Luminescent cell Viability Assay (Promega catalog number #G7570). 90 μl of cells (3,000 cells/well) were cultured in growth medium in a Corning black transparent bottom 96-well plate, and cultured in a 5% $CO_2$ humidified incubator at 37° C. overnight. The compound serially diluted in 100% DMSO was added to the cells using a pipette, and the cells were incubated for another 72 hours. 100 μl of the mixed Cell Titer-Glo reagent was added to the cells in the 96-well culture plate to lyse the cells and mix gently. Subsequently, the autofluorescence was detected on the Envision microplate detector to obtain the data of each compound. Finally, the data was input into a suitable software package (such as Prism) for curve fitting analysis. Based on this data and by calculating the compound concentration required to obtain a 50% inhibitory effect, the $IC_{50}$ value was determined.

Table 6 below showed the $IC_{50}$ values of the compounds in Examples 8-15 herein in the above BaF3 (EGFR-D770insNPG) cell proliferation test.

TABLE 6

| Example number | Test 6 - $IC_{50}$ (nM) |
| --- | --- |
| 8 | 22.76 |
| 9 | 12.76 |
| 10 | 180.5 |
| 11 | 10.24 |
| 12 | 75.3 |
| 13 | 40.9 |
| 14 | 10.02 |
| 15 | 8.87 |
| Osimertinib (AZD9291) | 31.68 |

Test 7: BaF3 (EGFR-S768I) Cell Proliferation Test

The engineered cell line BaF3 (EGFR-S768I) was constructed by the inventor himself (for the method of cell line construction, see Jingrui Jiang et al., Cancer Res. 2005 Oct. 1; 65 (19): 8964-74; Jacqulyne P. Robichaux et al., Nat Med. 2018 May; 24 (5): 638-646). BaF3 (EGFR-S768I) was cultured in RPMI1640 medium containing 10% fetal bovine serum and 2 mM glutamine. The cells were grown at 37° C. in a humidified incubator with 5% $CO_2$.

The number of viable cells in the culture was measured according to the protocol described in Promega's Cell Titer-Glo Luminescent cell Viability Assay (Promega catalog number #G7570). 90 μl of cells (3,000 cells/well) were cultured in growth medium in a Corning black transparent bottom 96-well plate, and cultured in a 5% $CO_2$ humidified incubator at 37° C. overnight. The compound serially diluted in 100% DMSO was added to the cells using a pipette, and the cells were incubated for another 72 hours. 100 μl of the mixed Cell Titer-Glo reagent was added to the cells in the 96-well culture plate to lyse the cells and mix gently. Subsequently, the autofluorescence was detected on the Envision microplate detector to obtain the data of each compound. Finally, the data was input into a suitable software package (such as Prism) for curve fitting analysis.

Based on this data and by calculating the compound concentration required to obtain a 50% inhibitory effect, the $IC_{50}$ value was determined.

Table 7 below showed the $IC_{50}$ values of the compounds of Examples 8-15 herein in the above BaF3 (EGFR-S768I) cell proliferation test.

TABLE 7

| Example number | Test 7 - $IC_{50}$ (nM) |
| --- | --- |
| 8 | 7.82 |
| 9 | 9.17 |
| 10 | 44.5 |
| 11 | 38.1 |
| 12 | 29.4 |
| 13 | 13.6 |
| 14 | 8.91 |
| 15 | 7.41 |
| Osimertinib (AZD9291) | 37.15 |

Test 8: BaF3 (EGFR-L8610) Cell Proliferation Test

The engineered cell line BaF3 (EGFR-L861Q) was constructed by the inventor himself (see Jingrui Jiang et al., Cancer Res. 2005 Oct. 1; 65 (19): 8964-74 for the cell line construction method; Jacqulyne P. Robichaux et al., Nat Med. 2018 May; 24 (5): 638-646). BaF3 (EGFR-L861Q) was cultured in RPMI1640 medium containing 10% fetal bovine serum and 2 mM glutamine. The cells were grown at 37° C. in a humidified incubator with 5% $CO_2$.

The number of viable cells in the culture was measured according to the protocol described in Promega's Cell Titer-Glo Luminescent cell Viability Assay (Promega catalog number #G7570). 90 µl of cells (3,000 cells/well) were cultured in growth medium in a Corning black transparent bottom 96-well plate, and cultured in a 5% $CO_2$ humidified incubator at 37° C. overnight. The compound serially diluted in 100% DMSO was added to the cells using a pipette, and the cells were incubated for another 72 hours. 100 µl of the mixed Cell Titer-Glo reagent was added to the cells in the 96-well culture plate to lyse the cells and mix gently. Subsequently, the autofluorescence was detected on the Envision microplate detector to obtain the data of each compound. Finally, the data was input into a suitable software package (such as Prism) for curve fitting analysis. Based on this data and by calculating the compound concentration required to obtain a 50% inhibitory effect, the $IC_{50}$ value was determined.

Table 8 below showed the $IC_{50}$ values of the compounds of Examples 8-15 herein in the above BaF3 (EGFR-L861Q) cell proliferation test.

TABLE 8

| Example number | Test 8 - $IC_{50}$ (nM) |
| --- | --- |
| 8 | 5.82 |
| 9 | 5.01 |
| 10 | 36.1 |
| 11 | 22.5 |
| 12 | 17.2 |
| 13 | 10.8 |
| 14 | 4.58 |
| 15 | 3.87 |
| Osimertinib (AZD9291) | 11.58 |

Test 9: BaF3 (HER2-A775insYVMA) Cell Proliferation Test

The engineered cell line BaF3 (HER2-A775insYVMA) was constructed by the inventor himself (for the method of cell line construction, see Jingrui Jiang et al., Cancer Res. 2005 Oct. 1; 65 (19): 8964-74; Jacqulyne P. Robichaux et al., Nat Med. 2018 May; 24 (5): 638-646). BaF3 (HER2-A775insYVMA) was cultured in RPMI1640 medium containing 10% fetal bovine serum and 2 mM glutamine. The cells were grown at 37° C. in a humidified incubator with 5% $CO_2$.

The number of viable cells in the culture was measured according to the protocol described in Promega's Cell Titer-Glo Luminescent cell Viability Assay (Promega catalog number #G7570). 90 µl of cells (3,000 cells/well) were cultured in growth medium in a Corning black transparent bottom 96-well plate, and cultured in a 5% $CO_2$ humidified incubator at 37° C. overnight. The compound serially diluted in 100% DMSO was added to the cells using a pipette, and the cells were incubated for another 72 hours. 100 µl of the mixed Cell Titer-Glo reagent was added to the cells in the 96-well culture plate to lyse the cells and mix gently. Subsequently, the autofluorescence was detected on the Envision microplate detector to obtain the data of each compound. Finally, the data was input into a suitable software package (such as Prism) for curve fitting analysis. Based on this data and by calculating the compound concentration required to obtain a 50% inhibitory effect, the $IC_{50}$ value was determined.

Table 9 below showed the $IC_{50}$ values of the compounds of Examples 8-15 herein in the above BaF3 (HER2-A775insYVMA) cell proliferation test.

TABLE 9

| Example number | Test 9 - $IC_{50}$ (nM) |
| --- | --- |
| 8 | 21.8 |
| 9 | 13.9 |
| 10 | 45.2 |
| 11 | 14.2 |
| 12 | 98.2 |
| 13 | 85.2 |
| 14 | 12.44 |
| 15 | 10.78 |
| Osimertinib (AZD9291) | 61.19 |

Test 10: BaF3 (HER2-P780insGSP) Cell Proliferation Test

The engineered cell line BaF3 (HER2-P780insGSP) was constructed by the inventor himself (for the method of cell line construction, see Jingrui Jiang et al., Cancer Res. 2005 Oct. 1; 65 (19): 8964-74; Jacqulyne P. Robichaux et al., Nat Med. 2018 May; 24 (5): 638-646). BaF3 (HER2-P780insGSP) was cultured in RPMI1640 medium containing 10% fetal bovine serum and 2 mM glutamine. The cells were grown at 37° C. in a humidified incubator with 5% $CO_2$.

The number of viable cells in the culture was measured according to the protocol described in Promega's Cell Titer-Glo Luminescent cell Viability Assay (Promega catalog number #G7570). 90 µl of cells (3,000 cells/well) were cultured in growth medium in a Corning black transparent bottom 96-well plate, and cultured in a 5% $CO_2$ humidified incubator at 37° C. overnight. The compound serially diluted in 100% DMSO was added to the cells using a pipette, and the cells were incubated for another 72 hours. 100 µl of the mixed Cell Titer-Glo reagent was added to the cells in the 96-well culture plate to lyse the cells and mix gently. Subsequently, the autofluorescence was detected on the Envision microplate detector to obtain the data of each compound. Finally, the data was input into a suitable software package (such as Prism) for curve fitting analysis.

Based on this data and by calculating the compound concentration required to obtain a 50% inhibitory effect, the $IC_{50}$ value was determined.

Table 10 below showed the $IC_{50}$ values of the compounds in Examples 8-15 herein in the above BaF3 (HER2-P780insGSP) cell proliferation test.

TABLE 10

| Example number | Test 10 - $IC_{50}$ (nM) |
| --- | --- |
| 8 | 11.6 |
| 9 | 7.59 |
| 10 | 32.6 |
| 11 | 8.76 |
| 12 | 47.8 |
| 13 | 29.6 |
| 14 | 6.92 |
| 15 | 6.58 |
| Osimertinib (AZD9291) | 32.15 |

Test 11: BaF3 (HER2-G776insVC) Cell Proliferation Test

The engineered cell line BaF3 (HER2-G776insVC) was constructed by the inventor himself (for the method of cell line construction, see Jingrui Jiang et al., Cancer Res. 2005 Oct. 1; 65 (19): 8964-74; Jacqulyne P. Robichaux et al., Nat Med. 2018 May; 24 (5): 638-646). BaF3 (HER2-G776insVC) was cultured in RPMI1640 medium containing 10% fetal bovine serum and 2 mM glutamine. The cells were grown at 37° C. in a humidified incubator with 5% $CO_2$.

The number of viable cells in the culture was measured according to the protocol described in Promega's Cell Titer-Glo Luminescent cell Viability Assay (Promega catalog number #G7570). 90 µl of cells (3,000 cells/well) were cultured in growth medium in a Corning black transparent bottom 96-well plate, and cultured in a 5% $CO_2$ humidified incubator at 37° C. overnight. The compound serially diluted in 100% DMSO was added to the cells using a pipette, and the cells were incubated for another 72 hours. 100 µl of the mixed Cell Titer-Glo reagent was added to the cells in the 96-well culture plate to lyse the cells and mix gently. Subsequently, the autofluorescence was detected on the Envision microplate detector to obtain the data of each compound. Finally, the data was input into a suitable software package (such as Prism) for curve fitting analysis. Based on this data and by calculating the compound concentration required to obtain a 50% inhibitory effect, the $IC_{50}$ value was determined.

Table 11 below showed the $IC_{50}$ values of the compounds of Examples 8-15 herein in the above BaF3 (HER2-G776insVC) cell proliferation test.

TABLE 11

| Example number | Test 11 - $IC_{50}$ (nM) |
| --- | --- |
| 8 | 2.73 |
| 9 | 1.80 |
| 10 | 9.56 |
| 11 | 1.07 |
| 12 | 11.4 |
| 13 | 8.36 |
| 14 | 1.95 |
| 15 | 1.83 |
| Osimertinib (AZD9291) | 21.53 |

Test 12: HER4 Kinase Screening Test

Most kinase activity tests were carried out by T7 phage expressing kinase expressed in *E. coli* system. After *E. coli* grew to the logarithmic phase, *E. coli* was infected with T7 bacteriophage (moi=0.4) and cultured with shaking at 32° C. until lysis (90-150 minutes). The lysate was filtered with a centrifuge (6,000 g) and filtration membrane (0.2 µm) to remove cell debris. Other individual kinases to be tested were expressed by HEK-293 cells and labeled with DNA for qPCR detection.

The detection method was as follows: at room temperature, avidin-coated magnetic beads were treated with a biotinylated small molecule ligand for 30 minutes to generate an affinity resin for kinase assay. Next, the ligand magnetic beads were blocked with excess biotin and washed with blocking buffer (SeaBlock (Pierce), 1% BSA, 0.05% Tween-20, 1 mm DTT) to remove unbound ligand and reduce non-specific binding of phages. The next binding reaction was performed by binding kinase, ligand affinity beads and test compound in 1× binding buffer (20% Sea-Block, 0.17×PBS, 0.05% Tween-20, 6 mM DTT). 100% DMSO was used to prepare the test compound at a concentration of 40×, which was directly diluted into the reaction system. All reactions were carried out on a polypropylene 384-well plate, and the final volume of the reaction system was 0.02 ml. After the test plate was incubated at room temperature with shaking for 1 hour, the affinity beads were washed with wash buffer (1×PBS, 0.05% Tween-20). The beads were then resuspended in elution buffer (1×PBS, 0.05% Tween-20, 0.5 µM non-biotinylated affinity ligand), and incubated at room temperature for 30 minutes with shaking, and then the kinase concentration in the eluate was measured by qPCR method.

Table 12 below showed the inhibition rates of the compounds of Examples 11, 14 and 15 herein at concentrations of 1 µM and 10 µM against HER4 kinase.

TABLE 12

| Example number | 1 µM Inhibition rate (%) | 10 µM Inhibition rate (%) |
| --- | --- | --- |
| 11 | >95% | >95% |
| 14 | >98% | >98% |
| 15 | >98% | >98% |

Through the cell proliferation test of EGFR and HER2, it is found that the $IC_{50}$ value of the compound of formula (I) herein is relatively small, which indicates that the compound herein can inhibit the proliferation of EGFR and HER2 cells at the same time. At the same time, compared with the control compound Osimertinib (AZD9291), the $IC_{50}$ value of most of the compounds is much lower than that of Osimertinib (AZD9291), indicating that the inhibitory effect of the compounds herein on EGFR and HER2 is greatly improved. In addition, the compounds herein also have a significant inhibitory effect on the protein activity of HER4.

Test 13: EGFR Exon 20 Inserted D770insSVD Cell Proliferation Test

The human lung cell line BaF3 (EGFR/D770insSVD) was constructed by the applicant himself (for the method of cell line construction, see Jingrui Jiang et al., Cancer Res. 2005 Oct. 1; 65 (19): 8964-74; Jacqulyne P. Robichaux et al., Nat Med. 2018 May; 24 (5): 638-646). BaF3 (EGFR/D770insSVD) cells were cultured in RPMI 1640 medium containing 10% fetal bovine serum and 2 mM glutamine, and the cells were grown at 37° C. in a humidified incubator with 5% $CO_2$.

The number of viable cells in the culture was measured according to the protocol described in Promega's Cell Titer-Glo Luminescent cell Viability Assay (Promega catalog number #G7570). 90 µl of cells (3,000 cells/well) were cultured in growth medium in a Corning black transparent bottom 96-well plate, and cultured in a 5% $CO_2$ humidified incubator at 37° C. overnight. The compound serially diluted in 100% DMSO was added to the cells using a pipette, and the cells were incubated for another 72 hours. 100 µl of the mixed Cell Titer-Glo reagent was added to the cells in the 96-well culture plate to lyse the cells and mix gently. Subsequently, the autofluorescence was detected on the Envision microplate detector to obtain the data of each compound. Finally, the data was input into a suitable software package (such as Prism) for curve fitting analysis. Based on this data and by calculating the compound concentration required to obtain a 50% inhibitory effect, the $IC_{50}$ value was determined.

Test 14: EGFR Exon 20 Inserted A763insFQEA Cell Proliferation Test

The human lung cell line BaF3 (EGFR/A763insFQEA) was constructed by the applicant himself (for the method of cell line construction, see Jingrui Jiang et al., Cancer Res. 2005 Oct. 1; 65 (19): 8964-74; Jacqulyne P. Robichaux et al. Nat Med. 2018 May; 24 (5): 638-646). BaF3 (EGFR/A763insFQEA) cells were cultured in RPMI 1640 medium containing 10% fetal bovine serum and 2 mM glutamine, and the cells were grown at 37° C. in a humidified incubator with 5% $CO_2$.

The number of viable cells in the culture was measured according to the protocol described in Promega's Cell Titer-Glo Luminescent cell Viability Assay (Promega catalog number #G7570). 90 µl of cells (3,000 cells/well) were cultured in growth medium in a Corning black transparent bottom 96-well plate, and cultured in a 5% $CO_2$ humidified incubator at 37° C. overnight. The compound serially diluted in 100% DMSO was added to the cells using a pipette, and the cells were incubated for another 72 hours. 100 µl of the mixed Cell Titer-Glo reagent was added to the cells in the 96-well culture plate to lyse the cells and mix gently. Subsequently, the autofluorescence was detected on the Envision microplate detector to obtain the data of each compound. Finally, the data was input into a suitable software package (such as Prism) for curve fitting analysis. Based on this data and by calculating the compound concentration required to obtain a 50% inhibitory effect, the $IC_{50}$ value was determined.

Test 15: EGFR Exon 20 Inserted V769insASV Cell Proliferation Test

The human lung cell line BaF3 (EGFR/V769insASV) was constructed by the applicant himself (for the method of cell line construction, see Jingrui Jiang et al., Cancer Res. 2005 Oct. 1; 65 (19): 8964-74; Jacqulyne P. Robichaux et al., Nat Med. 2018 May; 24 (5): 638-646). BaF3 (EGFR/V769insASV) cells were cultured in RPMI 1640 medium containing 10% fetal bovine serum and 2 mM glutamine, and the cells were grown at 37° C. in a humidified incubator with 5% $CO_2$.

The number of viable cells in the culture was measured according to the protocol described in Promega's Cell Titer-Glo Luminescent cell Viability Assay (Promega catalog number #G7570). 90 µl of cells (3000 cells/well) were cultured in growth medium in a Corning black transparent bottom 96-well plate, and cultured in a 5% $CO_2$ humidified incubator at 37° C. overnight. The compound serially diluted in 100% DMSO was added to the cells using a pipette, and the cells were incubated for another 72 hours. 100 µl of the mixed Cell Titer-Glo reagent was added to the cells in the 96-well culture plate to lyse the cells and mix gently. Subsequently, the autofluorescence was detected on the Envision microplate detector to obtain the data of each compound. Finally, the data was input into a suitable software package (such as Prism) for curve fitting analysis. Based on this data and by calculating the compound concentration required to obtain a 50% inhibitory effect, the $IC_{50}$ value was determined.

Test 16: EGFR Exon 20 Inserted N771insH Cell Proliferation Test

The engineered cell line BaF3 (EGFR/N771insH) was constructed by the inventor himself (for the method of cell line construction, see Jingrui Jiang et al., Cancer Res. 2005 Oct. 1; 65 (19): 8964-74; Jacqulyne P. Robichaux et al., Nat Med. 2018 May; 24 (5): 638-646). BaF3 (EGFR/N771insH) was cultured in RPMI 1640 medium containing 10% fetal bovine serum and 2 mM glutamine, and the cells were grown at 37° C. in a humidified incubator with 5% $CO_2$.

The number of viable cells in the culture was measured according to the protocol described in Promega's Cell Titer-Glo Luminescent cell Viability Assay (Promega catalog number #G7570). 90 µl of cells (3,000 cells/well) were cultured in growth medium in a Corning black transparent bottom 96-well plate, and cultured in a 5% $CO_2$ humidified incubator at 37° C. overnight. The compound serially diluted in 100% DMSO was added to the cells using a pipette, and the cells were incubated for another 72 hours. 100 µl of the mixed Cell Titer-Glo reagent was added to the cells in the 96-well culture plate to lyse the cells and mix gently. Subsequently, the autofluorescence was detected on the Envision microplate detector to obtain the data of each compound. Finally, the data was input into a suitable software package (such as Prism) for curve fitting analysis. Based on this data and by calculating the compound concentration required to obtain a 50% inhibitory effect, the $IC_{50}$ value was determined.

Test 17: EGFR Exon 20 Inserted D770insNPG Cell Proliferation Test

The engineered cell line BaF3 (EGFR/D770insNPG) was constructed by the inventor himself (for the method of cell line construction, see Jingrui Jiang et al., Cancer Res. 2005 Oct. 1; 65 (19): 8964-74; Jacqulyne P. Robichaux et al., Nat Med. 2018 May; 24 (5): 638-646). BaF3 (EGFR/D770insNPG) was cultured in RPMI 1640 medium containing 10% fetal bovine serum and 2 mM glutamine, and cells were grown at 37° C. in a humidified incubator with 5% $CO_2$.

The number of viable cells in the culture was measured according to the protocol described in Promega's Cell Titer-Glo Luminescent cell Viability Assay (Promega catalog number #G7570). 90 µl of cells (3,000 cells/well) were cultured in growth medium in a Corning black transparent bottom 96-well plate, and cultured in a 5% $CO_2$ humidified incubator at 37° C. overnight. The compound serially diluted in 100% DMSO was added to the cells using a pipette, and the cells were incubated for another 72 hours. 100 µl of the mixed Cell Titer-Glo reagent was added to the cells in the 96-well culture plate to lyse the cells and mix gently. Subsequently, the autofluorescence was detected on the Envision microplate detector to obtain the data of each compound. Finally, the data was input into a suitable software package (such as Prism) for curve fitting analysis. Based on this data and by calculating the compound concentration required to obtain a 50% inhibitory effect, the $IC_{50}$ value was determined.

Test 18: EGFR Exon 20 Inserted V774insHV Cell Proliferation Test

The engineered cell line BaF3 (EGFR/V774insHV) was constructed by the inventor himself (for the method of cell line construction, see Jingrui Jiang et al., Cancer Res. 2005 Oct. 1; 65 (19): 8964-74; Jacqulyne P. Robichaux et al., Nat Med. 2018 May; 24 (5): 638-646). BaF3 (EGFR/V774insHV) was cultured in RPMI 1640 medium containing 10% fetal bovine serum and 2 mM glutamine, and cells were grown at 37° C. in a humidified incubator with 5% $CO_2$.

The number of viable cells in the culture was measured according to the protocol described in Promega's Cell Titer-Glo Luminescent cell Viability Assay (Promega catalog number #G7570). 90 μl of cells (3,000 cells/well) were cultured in growth medium in a Corning black transparent bottom 96-well plate, and cultured in a 5% $CO_2$ humidified incubator at 37° C. overnight. The compound serially diluted in 100% DMSO was added to the cells using a pipette, and the cells were incubated for another 72 hours. 100 μl of the mixed Cell Titer-Glo reagent was added to the cells in the 96-well culture plate to lyse the cells and mix gently. Subsequently, the autofluorescence was detected on the Envision microplate detector to obtain the data of each compound. Finally, the data was input into a suitable software package (such as Prism) for curve fitting analysis. Based on this data and by calculating the compound concentration required to obtain a 50% inhibitory effect, the $IC_{50}$ value was determined.

Test 19: EGFR/S768I Mutant Cell Line Proliferation Test

Human lung cell line BaF3 (EGFR/S768I) was established by the applicant (for the method of cell line construction, see Jingrui Jiang et al., Cancer Res. 2005 Oct. 1; 65 (19): 8964-74; Jacqulyne P. Robichaux et al., Nat Med. 2018 May; 24 (5): 638-646). BaF3 (EGFR-S768I) cells were cultured in RPMI 1640 medium containing 10% fetal bovine serum and 2 mM glutamine, and the cells were grown at 37° C. in a humidified incubator with 5% $CO_2$.

The number of viable cells in the culture was measured according to the protocol described in Promega's Cell Titer-Glo Luminescent cell Viability Assay (Promega catalog number #G7570). 90 μl of cells (3,000 cells/well) were cultured in growth medium in a Corning black transparent bottom 96-well plate, and cultured in a 5% $CO_2$ humidified incubator at 37° C. overnight. The compound serially diluted in 100% DMSO was added to the cells using a pipette, and the cells were incubated for another 72 hours. 100 μl of the mixed Cell Titer-Glo reagent was added to the cells in the 96-well culture plate to lyse the cells and mix gently. Subsequently, the autofluorescence was detected on the Envision microplate detector to obtain the data of each compound. Finally, the data was input into a suitable software package (such as Prism) for curve fitting analysis. Based on this data and by calculating the compound concentration required to obtain a 50% inhibitory effect, the $IC_{50}$ value was determined.

Test 20: EGFR/L861Q Mutant Cell Line Proliferation Test

The engineered cell line BaF3 (EGFR/L861Q) was constructed by the inventor himself (for the method of cell line construction, see Jingrui Jiang et al., Cancer Res. 2005 Oct. 1; 65 (19): 8964-74; Jacqulyne P. Robichaux et al., Nat Med. 2018 May; 24 (5): 638-646). BaF3 (EGFR/L861Q) cells were cultured in RPMI 1640 medium containing 10% fetal bovine serum and 2 mM glutamine, and the cells were grown at 37° C. in a humidified incubator with 5% $CO_2$.

The number of viable cells in the culture was measured according to the protocol described in Promega's Cell Titer-Glo Luminescent cell Viability Assay (Promega catalog number #G7570). 90 μl of cells (3,000 cells/well) were cultured in growth medium in a Corning black transparent bottom 96-well plate, and cultured in a 5% $CO_2$ humidified incubator at 37° C. overnight. The compound serially diluted in 10000 DMSO was added to the cells using a pipette, and the cells were incubated for another 72 hours. 100 μl of the mixed Cell Titer-Glo reagent was added to the cells in the 96-well culture plate to lyse the cells and mix gently. Subsequently, the autofluorescence was detected on the Envision microplate detector to obtain the data of each compound. Finally, the data was input into a suitable software package (such as Prism) for curve fitting analysis. Based on this data and by calculating the compound concentration required to obtain a 50% inhibitory effect, the $IC_{50}$ value was determined.

Table 13 below showed the $IC_{50}$ values of the compounds in Example 16 herein in the above cell proliferation tests 13-20, wherein only compound 16 was tested in tests 16-20.

TABLE 13

| Compound Number | Test 13 $IC_{50}$ (nM) | Test 14 $IC_{50}$ (nM) | Test 15 $IC_{50}$ (nM) | Test 16 $IC_{50}$ (nM) | Test 17 $IC_{50}$ (nM) | Test 18 $IC_{50}$ (nM) | Test 19 $IC_{50}$ (nM) | Test 20 $IC_{50}$ (nM) |
|---|---|---|---|---|---|---|---|---|
| 16 | 35.85 | 12.82 | 24.85 | 8.67 | 4.69 | 7.59 | 8.63 | 21.59 |
| 17 | 58.04 | 14.75 | 36.43 | — | — | — | — | — |
| 18 | 319.7 | 131.3 | 244 | — | — | — | — | — |
| 19 | 144.4 | 42.61 | 147.7 | — | — | — | — | — |
| 20 | 89.21 | 75.06 | 154.7 | — | — | — | — | — |
| 21 | 80.99 | 50.15 | 98.59 | — | — | — | — | — |
| 22 | 247.7 | 193.1 | 365.4 | — | — | — | — | — |
| 23 | 218.8 | 121.9 | 264.4 | — | — | — | — | — |
| 24 | 207.2 | 212.9 | 266.2 | — | — | — | — | — |
| 25 | 78.94 | 51.05 | 103.6 | — | — | — | — | — |
| 26 | 142.2 | 38.28 | 126.2 | — | — | — | — | — |
| 27 | 195.2 | 176.8 | 318.6 | — | — | — | — | — |
| 28 | 236.9 | 66.36 | 175.9 | — | — | — | — | — |
| 29 | 240.2 | 60.74 | 173.8 | — | — | — | — | — |
| 30 | 239.5 | 63.58 | 177.0 | — | — | — | — | — |
| 31 | 45.01 | 13.01 | 28.39 | 9.43 | 4.58 | — | — | — |
| 32 | 54.52 | 15.72 | 26.87 | 10.24 | 4.73 | — | — | — |
| 33 | 49.51 | 15.01 | 25.73 | 10.08 | 5.87 | — | — | — |
| 34 | 598.5 | 53.82 | 406.1 | — | — | — | — | — |
| 35 | 146.1 | 106.2 | 105.1 | — | — | — | — | — |
| 36 | 454 | 170.1 | 324.6 | — | — | — | — | — |
| 37 | 900.8 | 542.5 | 669 | — | — | — | — | — |
| 38 | >3333 | 71.16 | >3333 | — | — | — | — | — |
| 39 | 963.3 | 309.2 | 455.3 | — | — | — | — | — |
| Osimertinib (AZD9291) | 305.0 | 118.6 | 307.1 | 33.54 | 11.58 | 33.53 | 31.68 | 69.91 |

Note:
"—" means not detected.

From the above test results, it is found that most of the above compounds have a small $IC_{50}$ value in the above cell proliferation test, most of which are significantly lower than the $IC_{50}$ value of Osimertinib (AZD9291), and the minimum is reduced by more than 10 times, indicating that the compounds herein can inhibit cell proliferation very well. Specifically, the compounds described in compounds 1, 2, 4, 5, 6, 10, 16, 17 and 18 all exhibited significant superior cell activity over Osimertinib (AZD9291) against EGFR exon 20 insertion mutations A763insFQEA, V769insASV, D770insSVD; compound 16 exhibited significantly superior cell activity over Osimertinib (AZD9291) against EGFR exon 20 insertion mutations N771insH, D770insNPQV774insHV; Compounds 16, 31, 32 and 33 demonstrated superior activity over Osimertinib (AZD9291) against EGFR S768I and EGFR L861Q mutations.

Test 21: HER2 Exon 20 Inserted A775insYVMA Cell Proliferation Test

The engineered cell line BaF3 (HER2/A775insYVMA) was constructed by the inventor himself (for the method of cell line construction, see Jingrui Jiang et al., Cancer Res. 2005 Oct. 1; 65 (19): 8964-74; Jacqulyne P. Robichaux et al., Nat Med. 2018 May; 24 (5): 638-646). BaF3 (HER2/A775insYVMA) was cultured in RPMI 1640 medium containing 10% fetal bovine serum and 2 mM glutamine, and the cells were grown at 37° C. in a humidified incubator with 5% $CO_2$.

The number of viable cells in the culture was measured according to the protocol described in Promega's Cell Titer-Glo Luminescent cell Viability Assay (Promega catalog number #G7570). 90 μl of cells (3,000 cells/well) were cultured in growth medium in a Corning black transparent bottom 96-well plate, and cultured in a 5% $CO_2$ humidified incubator at 37° C. overnight. The compound serially diluted in 100% DMSO was added to the cells using a pipette, and the cells were incubated for another 72 hours. 100 μl of the mixed Cell Titer-Glo reagent was added to the cells in the 96-well culture plate to lyse the cells and mix gently. Subsequently, the autofluorescence was detected on the Envision microplate detector to obtain the data of each compound. Finally, the data was input into a suitable software package (such as Prism) for curve fitting analysis. Based on this data and by calculating the compound concentration required to obtain a 50% inhibitory effect, the $IC_{50}$ value was determined.

Test 22: HER2 Exon 20 Inserted P780insGSP Cell Proliferation Test

The engineered cell line BaF3 (HER2/P780insGSP) was constructed by the inventor himself (for the method of cell line construction, see Jingrui Jiang et al., Cancer Res. 2005 Oct. 1; 65 (19): 8964-74; Jacqulyne P. Robichaux et al., Nat Med. 2018 May; 24 (5): 638-646). BaF3 (HER2/P780insGSP) was cultured in RPMI 1640 medium containing 10% fetal bovine serum and 2 mM glutamine, and the cells were grown at 37° C. in a humidified incubator with 5% $CO_2$.

The number of viable cells in the culture was measured according to the protocol described in Promega's Cell Titer-Glo Luminescent cell Viability Assay (Promega catalog number #G7570). 90 μl of cells (3,000 cells/well) were cultured in growth medium in a Corning black transparent bottom 96-well plate, and cultured in a 5% $CO_2$ humidified incubator at 37° C. overnight. The compound serially diluted in 100% DMSO was added to the cells using a pipette, and the cells were incubated for another 72 hours. 100 μl of the mixed Cell Titer-Glo reagent was added to the cells in the 96-well culture plate to lyse the cells and mix gently. Subsequently, the autofluorescence was detected on the Envision microplate detector to obtain the data of each compound. Finally, the data was input into a suitable software package (such as Prism) for curve fitting analysis. Based on this data and by calculating the compound concentration required to obtain a 50% inhibitory effect, the $IC_{50}$ value was determined.

Test 23: HER2 Exon 20 Inserted G776insVC Cell Proliferation Test

The engineered cell line BaF3 (HER2/G776insVC) was constructed by the inventor himself (for the method of cell line construction, see Jingrui Jiang et al., Cancer Res. 2005 Oct. 1; 65 (19): 8964-74; Jacqulyne P. Robichaux et al., Nat Med. 2018 May; 24 (5): 638-646). BaF3 (HER2/G776insVC) was cultured in RPMI 1640 medium containing 10% fetal bovine serum and 2 mM glutamine, and the cells were grown at 37° C. in a humidified incubator with 5% $CO_2$.

The number of viable cells in the culture was measured according to the protocol described in Promega's Cell Titer-Glo Luminescent cell Viability Assay (Promega catalog number #G7570). 90 μl of cells (3,000 cells/well) were cultured in growth medium in a Corning black transparent bottom 96-well plate, and cultured in a 5% $CO_2$ humidified incubator at 37° C. overnight. The compound serially diluted in 100% DMSO was added to the cells using a pipette, and the cells were incubated for another 72 hours. 100 μl of the mixed Cell Titer-Glo reagent was added to the cells in the 96-well culture plate to lyse the cells and mix gently. Subsequently, the autofluorescence was detected on the Envision microplate detector to obtain the data of each compound. Finally, the data was input into a suitable software package (such as Prism) for curve fitting analysis. Based on this data and by calculating the compound concentration required to obtain a 50% inhibitory effect, the $IC_{50}$ value was determined.

Table 14 below showed the $IC_{50}$ values of Compound 16 herein in the above cell proliferation tests 21-23.

TABLE 14

| Compound number | test 21 $IC_{50}$ (nM) | test 22 $IC_{50}$ (nM) | test 23 $IC_{50}$ (nM) |
| --- | --- | --- | --- |
| 16 | 7.67 | 1.64 | 12.05 |
| Osimertinib (AZD9291) | 32.15 | 21.53 | 61.19 |

From the above test results, it is found that the $IC_{50}$ value of Compound 16 is significantly lower than that of Osimertinib (AZD9291), which is reduced by 3-8 times, which shows that compound 1 can effectively inhibit the proliferation of HER2 exon 20 insertion mutation cells, showing superior cell activity over Osimertinib (AZD9291) against HER2 exon 20 insertion mutation.

Test 24: HER4 Kinase Inhibition Test

To determine the compound's inhibition against HER4 kinase activity, first 1× kinase buffer was formulated, which included 50 mM HEPES, pH 7.5, 0.0015% Brij-35, and reaction stop solution, including 100 mM HEPES, pH 7.5, 0.015% Brij-35, 0.2% Coating Reagent #3, 50 mM EDTA. Next, 100% DMSO was used to formulate the test compound into a solution of 50× at the final test concentration, and then sequentially diluted to 10 test concentrations; 100 μL of 100% DMSO was added to the blank control well as a negative control group without the compound and kinase. 10 μL of the above test compound (50×) was transferred to a new 96-well plate, and 90 μL of 1× kinase buffer was added to each well, and shaken for 10 minutes; then 5 μL of the mixture was transferred from the 96-well plate to a new 384-well plate, 10 μL of 1× kinase buffer was added and incubated at room temperature for 10 minutes. Finally, 10 μL of 2.5× peptide solution was added to the 384-well plate. After incubating at 25° C. for 10 minutes, 25 μL of reaction stop solution was added. Finally, the absorbance was detected on the Envision microplate detector to obtain the data of each compound. Finally, the data was input into a suitable software package (such as Prism) for curve fitting analysis. Based on this data and by calculating the compound concentration required to obtain a 50% inhibitory effect, the $IC_{50}$ value was determined.

Table 15 below showed the $IC_{50}$ value of Compound 16 herein in the above HER4 kinase inhibition test.

TABLE 15

| Compound number | Test 12 HER4 $IC_{50}$ (nM) |
| --- | --- |
| 16 | 29 |
| Osimertinib (AZD9291) | 47 |

From the above test results, it is found that the $IC_{50}$ value of compound 16 is significantly lower than that of Osimertinib (AZD9291), which is about 1 fold lower, which shows that compound 16 can effectively inhibit the activity of HER4 kinase, showing superior kinase inhibitory activity over Osimertinib (AZD9291) against HER4.

The invention claimed is:

1. A compound or a pharmaceutically acceptable salt thereof, wherein the compound is selected from:

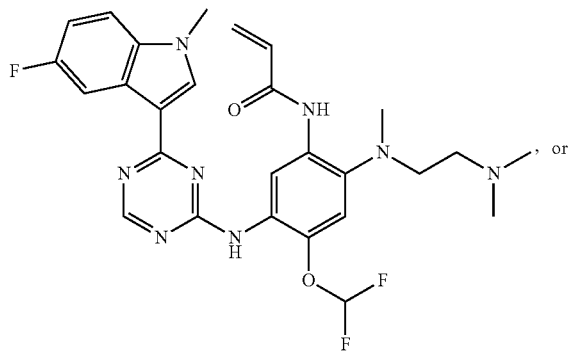

2. A pharmaceutical composition, comprising the compound or a pharmaceutically acceptable salt thereof according to claim 1 and a pharmaceutically acceptable diluent or carrier.

3. The composition according to claim 2 for use in the treatment of a cancer selected from: ovarian cancer, non-small cell lung cancer, small cell lung cancer, cervical cancer, colorectal cancer, breast cancer, pancreatic cancer, glioma, glioblastoma, melanoma, prostate cancer, leukemia, lymphoma, non-Hodgkin's lymphoma, gastric cancer, lung cancer, hepatocellular carcinoma, gastric cancer, gastrointestinal stromal tumor, thyroid cancer, cholangiocarcinoma, endometrial cancer, kidney cancer, anaplastic large cell lymphoma, acute myeloid leukemia, multiple myeloma, melanoma, and mesothelioma.

4. The composition according to claim 3, wherein the cancer is non-small cell lung cancer or small cell lung cancer or lung cancer with brain metastasis.

5. A method for treating cancer, comprising administrating the compound or a pharmaceutically acceptable salt thereof according to claim 1 to a subject.

6. The method according to claim 5, wherein the cancer is selected from: ovarian cancer, non-small cell lung cancer, small cell lung cancer, cervical cancer, colorectal cancer, breast cancer, pancreatic cancer, glioma, glioblastoma, melanoma, prostate cancer, leukemia, lymphoma, non-Hodgkin's lymphoma, gastric cancer, lung cancer, hepatocellular carcinoma, gastric cancer, gastrointestinal stromal tumor, thyroid cancer, cholangiocarcinoma, endometrial cancer, kidney cancer, anaplastic large cell lymphoma, acute myeloid leukemia, multiple myeloma, melanoma, and mesotheliom.

7. The method according to claim 5, wherein the cancer is non-small cell lung cancer or small cell lung cancer or lung cancer with brain metastasis.

8. The method according to claim 5, comprising administrating the compound or a pharmaceutically acceptable salt thereof and an additional antitumor substance for the simultaneous, independent or sequential treatment of cancer.

* * * * *